(12) United States Patent
Iversen

(10) Patent No.: US 9,394,323 B2
(45) Date of Patent: Jul. 19, 2016

(54) ANTISENSE ANTIVIRAL COMPOUND AND METHOD FOR TREATING INFLUENZA VIRAL INFECTION

(71) Applicant: Sarepta Therapeutics, Inc., Corvallis, OR (US)

(72) Inventor: Patrick L. Iversen, Corvallis, OR (US)

(73) Assignee: SAREPTA THERAPEUTICS, INC., Corvallis, OR (US)

( * ) Notice: Subject to any disclaimer, the term of this patent is extended or adjusted under 35 U.S.C. 154(b) by 0 days.

(21) Appl. No.: 14/251,124

(22) Filed: Apr. 11, 2014

(65) Prior Publication Data

US 2014/0303073 A1 Oct. 9, 2014

Related U.S. Application Data

(63) Continuation of application No. 12/945,081, filed on Nov. 12, 2010, now Pat. No. 8,697,858.

(60) Provisional application No. 61/261,278, filed on Nov. 13, 2009, provisional application No. 61/292,056, filed on Jan. 4, 2010, provisional application No. 61/377,382, filed on Aug. 26, 2010.

(51) Int. Cl.

| | | |
|---|---|---|
| *A61K 48/00* | (2006.01) | |
| *C07F 9/6561* | (2006.01) | |
| *C12N 15/113* | (2010.01) | |
| *A61K 31/165* | (2006.01) | |
| *A61K 31/43* | (2006.01) | |
| *A61K 31/5377* | (2006.01) | |
| *A61K 31/545* | (2006.01) | |
| *A61K 31/7056* | (2006.01) | |
| *A61K 38/08* | (2006.01) | |
| *A61K 38/10* | (2006.01) | |
| *C07K 7/06* | (2006.01) | |
| *C07K 7/08* | (2006.01) | |

(52) U.S. Cl.
CPC ............ *C07F 9/65616* (2013.01); *A61K 31/165* (2013.01); *A61K 31/43* (2013.01); *A61K 31/5377* (2013.01); *A61K 31/545* (2013.01); *A61K 31/7056* (2013.01); *A61K 38/08* (2013.01); *A61K 38/10* (2013.01); *C07K 7/06* (2013.01); *C07K 7/08* (2013.01); *C12N 15/113* (2013.01); *C12N 15/1131* (2013.01); *C12N 2310/11* (2013.01); *C12N 2310/315* (2013.01); *C12N 2310/3181* (2013.01); *C12N 2310/321* (2013.01); *C12N 2310/3231* (2013.01); *C12N 2310/3233* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 3,420,788 A | 1/1969 | Solms | 260/17.4 |
| 3,426,011 A | 2/1969 | Parmerter et al. | 260/209 |
| 3,453,257 A | 7/1969 | Parmerter et al. | 260/209 |
| 3,453,259 A | 7/1969 | Parmerter et al. | 260/209 |
| 3,459,731 A | 8/1969 | Gramera et al. | 260/209 |
| 3,687,808 A | 8/1972 | Merigan, Jr. et al. | 195/28 N |
| 4,235,871 A | 11/1980 | Papahadjopoulos et al. | 424/19 |
| 4,469,863 A | 9/1984 | Ts'o et al. | 536/27 |
| 4,476,301 A | 10/1984 | Imbach et al. | 536/27 |
| 4,737,323 A | 4/1988 | Martin et al. | 264/4.3 |
| 5,013,830 A | 5/1991 | Ohtsuka et al. | 536/27 |
| 5,023,243 A | 6/1991 | Tullis | 514/44 |
| 5,034,506 A | 7/1991 | Summerton et al. | 528/391 |
| 5,122,048 A | 6/1992 | Deeds | 425/174.8 E |
| 5,134,127 A | 7/1992 | Stella et al. | 514/58 |
| 5,134,172 A | 7/1992 | Bruyninckx et al. | 521/137 |
| 5,142,047 A | 8/1992 | Summerton et al. | 544/118 |
| 5,149,797 A | 9/1992 | Pederson et al. | 536/27 |
| 5,166,315 A | 11/1992 | Summerton et al. | 528/406 |
| 5,177,196 A | 1/1993 | Meyer, Jr. et al. | 536/22.1 |

(Continued)

FOREIGN PATENT DOCUMENTS

| | | |
|---|---|---|
| JP | 6-501843 A | 3/1994 |
| JP | 9-121867 A | 5/1997 |

(Continued)

OTHER PUBLICATIONS

Haasnoot et al., "RNA Interference Against Viruses: Strike and Counterstrike," *Nature Biotechnology* 25(12):1435-1443, Dec. 2007.
Rygiel et al., "Lack of CD200 Enhances Pathological T Cell Responses During Influenza Infection," *The Journal of Immunology* 183(3):1990-1996, Aug. 2009.
Vlasov et al., "In Vitro Suppression of Translation of the Influenza Virus M1 Protein mRNA With the Aid of Antisense Oligonucleotides," *Molekulyarnaya Biologia Journal* 25(5):1332-1337, 1991, with English Translation, 13 pages.

(Continued)

*Primary Examiner* — Kimberly Chong
(74) *Attorney, Agent, or Firm* — Seed IP Law Group PLLC

(57) ABSTRACT

The present invention relates to antisense antiviral compounds and methods of their use and production in inhibition of growth of viruses of the Orthomyxoviridae family and in the treatment of a viral infection. The compounds are particularly useful in the treatment of influenza virus infection in a mammal. Exemplary antisense antiviral compounds are substantially uncharged, or partially positively charged, morpholino oligonucleotides having 1) a nuclease resistant backbone, 2) 12-40 nucleotide bases, and 3) a targeting sequence of at least 12 bases in length that hybridizes to a target region selected from the following: a) the 5' or 3' terminal 25 bases of the negative sense viral RNA segment of Influenzavirus A, Influenzavirus B and Influenzavirus C; b) the terminal 30 bases of the 5' or 3' terminus of the positive sense vcRNA; c) the 45 bases surrounding the AUG start codon of an influenza viral mRNA and; d) 50 bases surrounding the splice donor or acceptor sites of influenza mRNAs subject to alternative splicing.

36 Claims, 24 Drawing Sheets

(56) References Cited

U.S. PATENT DOCUMENTS

| | | | |
|---|---|---|---|
| 5,185,444 A | 2/1993 | Summerton et al. | 544/81 |
| 5,188,897 A | 2/1993 | Suhadolnik et al. | 428/402.2 |
| 5,194,428 A | 3/1993 | Agrawal et al. | 514/44 |
| 5,214,134 A | 5/1993 | Weis et al. | 536/25.3 |
| 5,216,141 A | 6/1993 | Benner | 536/27.13 |
| 5,217,866 A | 6/1993 | Summerton et al. | 435/6 |
| 5,220,007 A | 6/1993 | Pederson et al. | 536/23.1 |
| 5,235,033 A | 8/1993 | Summerton et al. | 528/391 |
| 5,256,775 A | 10/1993 | Froehler | 536/25.6 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,276,019 A | 1/1994 | Cohen et al. | 514/44 |
| 5,278,302 A | 1/1994 | Caruthers et al. | 536/24.5 |
| 5,286,717 A | 2/1994 | Cohen et al. | 514/44 |
| 5,321,131 A | 6/1994 | Agrawal et al. | 536/25.34 |
| 5,366,878 A | 11/1994 | Pederson et al. | 435/91.3 |
| 5,399,676 A | 3/1995 | Froehler | 536/23.1 |
| 5,403,711 A | 4/1995 | Walder et al. | 435/6 |
| 5,405,938 A | 4/1995 | Summerton et al. | 528/406 |
| 5,405,939 A | 4/1995 | Suhadolnik et al. | 530/322 |
| 5,434,257 A | 7/1995 | Matteucci et al. | 536/24.3 |
| 5,453,496 A | 9/1995 | Caruthers et al. | 536/24.5 |
| 5,455,233 A | 10/1995 | Spielvogel et al. | 514/44 |
| 5,466,677 A | 11/1995 | Baxter et al. | 514/44 |
| 5,470,967 A | 11/1995 | Huie et al. | 536/24.3 |
| 5,476,925 A | 12/1995 | Letsinger et al. | 536/23.1 |
| 5,489,677 A | 2/1996 | Sanghvi et al. | 536/22.1 |
| 5,491,133 A | 2/1996 | Walder et al. | 514/44 |
| 5,495,006 A | 2/1996 | Climie et al. | 536/24.1 |
| 5,506,337 A | 4/1996 | Summerton et al. | 528/391 |
| 5,519,126 A | 5/1996 | Hecht | 536/24.3 |
| 5,521,063 A | 5/1996 | Summerton et al. | 435/6 |
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,543,508 A | 8/1996 | Haseloff et al. | 536/23.2 |
| 5,545,729 A | 8/1996 | Goodchild et al. | 536/24.5 |
| 5,550,111 A | 8/1996 | Suhadolnik et al. | 514/44 |
| 5,561,225 A | 10/1996 | Maddry et al. | 536/23.1 |
| 5,563,253 A | 10/1996 | Agrawal et al. | 536/22.1 |
| 5,565,350 A | 10/1996 | Kmiec | 435/172.3 |
| 5,571,799 A | 11/1996 | Tkachuk et al. | 514/47 |
| 5,576,302 A | 11/1996 | Cook et al. | 514/44 |
| 5,580,767 A | 12/1996 | Cowsert et al. | 435/172.3 |
| 5,587,361 A | 12/1996 | Cook et al. | 514/44 |
| 5,596,086 A | 1/1997 | Matteucci et al. | 536/22.1 |
| 5,602,240 A | 2/1997 | De Mesmaeker et al. | 536/22.1 |
| 5,608,046 A | 3/1997 | Cook et al. | 536/23.1 |
| 5,610,289 A | 3/1997 | Cook et al. | 536/25.34 |
| 5,618,704 A | 4/1997 | Sanghvi et al. | 435/91.5 |
| 5,623,065 A | 4/1997 | Cook et al. | 536/23.1 |
| 5,623,070 A | 4/1997 | Cook et al. | 536/27.6 |
| 5,625,050 A | 4/1997 | Beaton et al. | 536/24.1 |
| 5,633,360 A | 5/1997 | Bischofberger et al. | 536/22.1 |
| 5,637,573 A | 6/1997 | Agrawal et al. | 514/44 |
| 5,652,355 A | 7/1997 | Metelev et al. | 536/24.5 |
| 5,652,356 A | 7/1997 | Agrawal | 536/24.5 |
| 5,663,312 A | 9/1997 | Chaturvedula | 536/22.1 |
| 5,677,437 A | 10/1997 | Teng et al. | 536/23.1 |
| 5,677,439 A | 10/1997 | Weis et al. | 536/23.1 |
| 5,697,248 A | 12/1997 | Brown | 73/290 V |
| 5,698,685 A | 12/1997 | Summerton et al. | 536/24.3 |
| 5,698,695 A | 12/1997 | Appleton et al. | 544/330 |
| 5,700,922 A | 12/1997 | Cook | 536/23.1 |
| 5,702,891 A | 12/1997 | Kolberg et al. | 435/6 |
| 5,714,331 A | 2/1998 | Buchardt et al. | 435/6 |
| 5,719,262 A | 2/1998 | Buchardt et al. | 530/300 |
| 5,734,039 A | 3/1998 | Calabretta et al. | 536/24.5 |
| 5,738,985 A | 4/1998 | Miles et al. | 435/5 |
| 5,801,154 A | 9/1998 | Baracchini et al. | 514/44 |
| 5,892,023 A | 4/1999 | Pirotzky et al. | 536/24.5 |
| 5,955,318 A | 9/1999 | Simons et al. | 435/71.1 |
| 5,955,589 A | 9/1999 | Cook et al. | 536/23.1 |
| 5,989,904 A | 11/1999 | Das et al. | 435/320.1 |
| 6,060,456 A | 5/2000 | Arnold, Jr. et al. | 514/44 |
| 6,133,246 A | 10/2000 | McKay et al. | 514/44 |
| 6,174,868 B1 | 1/2001 | Anderson et al. | 514/44 |
| 6,214,555 B1 | 4/2001 | Leushner et al. | 435/6 |
| 6,228,579 B1 | 5/2001 | Zyskind et al. | 435/6 |
| 6,239,265 B1 | 5/2001 | Cook | 536/23.1 |
| 6,245,747 B1 | 6/2001 | Porter et al. | 514/44 |
| 6,258,570 B1 | 7/2001 | Glustein et al. | 435/91.2 |
| 6,306,993 B1 | 10/2001 | Rothbard et al. | 526/304 |
| 6,365,351 B1 | 4/2002 | Iversen | 435/6 |
| 6,365,577 B1 | 4/2002 | Iversen | 514/44 |
| 6,391,542 B1 | 5/2002 | Anderson et al. | 435/6 |
| 6,495,663 B1 | 12/2002 | Rothbard et al. | 530/329 |
| 6,669,951 B2 | 12/2003 | Rothbard et al. | 424/436 |
| 6,670,461 B1 | 12/2003 | Wengel et al. | 536/23.1 |
| 6,677,153 B2 | 1/2004 | Iversen | 435/375 |
| 6,692,911 B2 | 2/2004 | Pack et al. | 435/6 |
| 6,784,291 B2 | 8/2004 | Iversen et al. | 536/24.5 |
| 6,794,499 B2 | 9/2004 | Wengel et al. | 536/23.1 |
| 6,828,105 B2 | 12/2004 | Stein et al. | 435/6 |
| 6,841,542 B2 | 1/2005 | Bartelmez et al. | 514/44 |
| 6,881,825 B1 | 4/2005 | Robbins et al. | 530/327 |
| 6,969,766 B2 | 11/2005 | Kim et al. | 544/277 |
| 7,022,851 B2 | 4/2006 | Kim et al. | 544/276 |
| 7,034,133 B2 | 4/2006 | Wengel et al. | 536/23.1 |
| 7,049,431 B2 | 5/2006 | Iversen | 536/24.5 |
| 7,053,207 B2 | 5/2006 | Wengel | 536/25.3 |
| 7,060,809 B2 | 6/2006 | Wengel et al. | 536/23.1 |
| 7,070,807 B2 | 7/2006 | Mixson | 424/484 |
| 7,084,125 B2 | 8/2006 | Wengel | 514/44 |
| 7,094,765 B1 | 8/2006 | Iversen et al. | 514/44 |
| 7,115,374 B2 | 10/2006 | Linnen | 435/6 |
| 7,125,994 B2 | 10/2006 | Kim et al. | 544/277 |
| 7,145,006 B2 | 12/2006 | Kim et al. | 544/276 |
| 7,163,695 B2 | 1/2007 | Mixson | 424/486 |
| 7,179,896 B2 | 2/2007 | Kim et al. | 536/23.1 |
| 7,211,668 B2 | 5/2007 | Kim et al. | 544/276 |
| 7,468,418 B2 | 12/2008 | Iversen et al. | 530/300 |
| 7,507,196 B2 | 3/2009 | Stein et al. | 514/44 |
| 7,524,829 B2 | 4/2009 | Stein et al. | 514/44 |
| 7,569,575 B2 | 8/2009 | Sørensen et al. | 514/263.23 |
| 7,572,582 B2 | 8/2009 | Wengel et al. | 435/6 |
| 7,582,615 B2 | 9/2009 | Neuman et al. | 514/44 |
| 7,807,801 B2 | 10/2010 | Iversen et al. | 536/22.1 |
| 7,855,283 B2 | 12/2010 | Iversen | 536/24.5 |
| 7,943,762 B2 | 5/2011 | Weller et al. | 536/31 |
| 8,030,291 B2 | 10/2011 | Stein et al. | 514/44 |
| 8,030,292 B2 | 10/2011 | Stein et al. | 514/44 |
| 2003/0087851 A1 | 5/2003 | Takaku et al. | 514/44 |
| 2003/0166588 A1 | 9/2003 | Iversen et al. | 514/44 |
| 2003/0171311 A1 | 9/2003 | Blatt et al. | 514/44 |
| 2003/0171335 A1 | 9/2003 | Stein et al. | 514/81 |
| 2003/0224353 A1 | 12/2003 | Stein et al. | 435/5 |
| 2004/0072239 A1 | 4/2004 | Renaud et al. | 435/7.1 |
| 2004/0110296 A1 | 6/2004 | Vargeese et al. | 435/458 |
| 2004/0259108 A1 | 12/2004 | Linnen et al. | 435/6 |
| 2004/0265879 A1 | 12/2004 | Iversen et al. | 435/6 |
| 2005/0171044 A1 | 8/2005 | Stein et al. | 514/44 |
| 2005/0176661 A1 | 8/2005 | Vaillant et al. | 514/44 |
| 2006/0008822 A1 | 1/2006 | Manoharan et al. | 435/6 |
| 2006/0035254 A1 | 2/2006 | Manoharan et al. | 435/6 |
| 2006/0063150 A1 | 3/2006 | Iversen et al. | 435/5 |
| 2006/0148747 A1 | 7/2006 | Stein et al. | 514/44 |
| 2006/0149046 A1 | 7/2006 | Arar | 536/23.2 |
| 2006/0269911 A1 | 11/2006 | Iversen et al. | 435/5 |
| 2006/0287260 A1 | 12/2006 | Manoharan et al. | 514/44 |
| 2007/0004661 A1 | 1/2007 | Stein et al. | 514/44 |
| 2007/0011435 A1 | 1/2007 | Lee | 712/15 |
| 2007/0037763 A1 | 2/2007 | Stein et al. | 514/44 |
| 2007/0054279 A1 | 3/2007 | Manoharan et al. | 435/6 |
| 2007/0066556 A1 | 3/2007 | Stein et al. | 514/44 |
| 2007/0129323 A1 | 6/2007 | Stein et al. | 514/44 |
| 2007/0197460 A1 | 8/2007 | Fougerolles et al. | 514/44 |
| 2007/0265214 A1 | 11/2007 | Stein et al. | 514/44 |
| 2007/0275465 A1 | 11/2007 | Woppmann et al. | 435/440 |
| 2008/0012804 A1 | 1/2008 | Kim et al. | 345/82 |
| 2008/0311556 A1 | 12/2008 | Iversen | 435/5 |
| 2009/0012280 A1 | 1/2009 | Stein et al. | 536/23.1 |

(56) References Cited

U.S. PATENT DOCUMENTS

| | | | |
|---|---|---|---|
| 2009/0082547 A1 | 3/2009 | Iversen et al. | 530/322 |
| 2009/0099066 A1 | 4/2009 | Moulton et al. | 514/7 |
| 2009/0186849 A1 | 7/2009 | Stein et al. | 514/44 |
| 2010/0016215 A1 | 1/2010 | Moulton et al. | 514/7 |
| 2010/0292189 A1 | 11/2010 | Iversen et al. | 514/81 |

FOREIGN PATENT DOCUMENTS

| | | |
|---|---|---|
| JP | 11-137260 A | 5/1999 |
| WO | WO 92/03454 A1 | 3/1992 |
| WO | WO 92/05305 A1 | 4/1992 |
| WO | WO 93/01286 A2 | 1/1993 |
| WO | WO 94/02595 A1 | 2/1994 |
| WO | WO 96/10390 A1 | 4/1996 |
| WO | WO 96/10391 A1 | 4/1996 |
| WO | WO 96/10392 A1 | 4/1996 |
| WO | WO 96/14057 A1 | 5/1996 |
| WO | WO 98/12312 A1 | 3/1998 |
| WO | WO 01/49775 A2 | 7/2001 |
| WO | WO 02/26968 A2 | 4/2002 |
| WO | WO 02/068637 A2 | 9/2002 |
| WO | WO 03/033657 A2 | 4/2003 |
| WO | WO 2005/007805 A2 | 1/2005 |
| WO | WO 2005/013905 A2 | 2/2005 |
| WO | WO 2005/030800 A2 | 4/2005 |
| WO | WO 2005/065268 A2 | 7/2005 |
| WO | WO 2006/033933 A2 | 3/2006 |
| WO | WO 2006/047683 A2 | 5/2006 |
| WO | WO 2006/050414 A2 | 5/2006 |
| WO | WO 2007/030576 A2 | 3/2007 |
| WO | WO 2007/030691 A2 | 3/2007 |
| WO | WO 2007/084359 A2 | 7/2007 |
| WO | WO 2007/103529 A2 | 9/2007 |
| WO | WO 2008/036127 A2 | 3/2008 |
| WO | WO 2009/005793 A2 | 1/2009 |
| WO | WO 2009/064471 A1 | 5/2009 |
| WO | WO 2011/060320 A1 | 5/2011 |

OTHER PUBLICATIONS

Abe et al., "Specific inhibition of influenza virus RNA polymerase and nucleoprotein gene expression by liposomally encapsulated antisense phosphorothioate oligonucleotides in MDCK cells," *Antiviral Chemistry & Chemotherapy* 9:253-262, 1998.

Abe et al., "Inhibition of Influenza Virus Replication by Phosphorothioate and Liposomally Endocapsulated Oligonucleotides," *Nucleosides & Nucleotides* 17(1-3):471-478, 1998.

Abe et al., "Antisense therapy of influenza," *European Journal of Pharmaceutical Sciences* 13:61-69, 2001.

Abes et al., "Delivery of steric block morpholino oligomers by (R-X-R)$_4$ peptides: structure-activity studies," *Nucleic Acids Research* 36(20):6343-6354, Sep. 16, 2008.

Agrawal et al., "Antisense therapeutics: is it as simple as complementary base recognition?," *Molecular Medicine Today* 6:72-81, Feb. 2000.

Agrawal et al., "Oligodeoxynucleoside phosphoramidates and phosphorothioates as inhibitors of human immunodeficiency virus," *Proc. Natl. Acad. Sci. USA* 85:7079-7083, Oct. 1988.

Agrawal et al., "Site-specific excision from RNA by RNase H and mixed-phosphate-backbone oligodeoxynucleotides," *Proc. Natl. Acad. Sci. USA* 87:1401-1405, Feb. 1990.

Akhtar et al., "Cellular uptake and intracellular fate of antisense oligonucleotides," *Trends in Cell Biology* 2:139-144, May 1992.

Altschul et al., "Gapped BLAST and PSI-BLAST: a new generation of protein database search programs," *Nucleic Acids Research* 25(17):3389-3402, 1997.

Anderson et al., Inhibition of Human Cytomegalovirus Immediate-Early Gene Expression by an Antisense Oligonucleotide Complementary to Immediate-Early RNA, *Antimicrobial Agents and Chemotherapy* 40(9):2004-2011, Sep. 1996.

Arora et al., "Redirection of drug metabolism using antisense technology," *Current Opinion in Molecular Therapeutics* 3(3):249-257, 2001.

Bailey et al., "Cationic oligonucleotides can mediate specific inhibition of gene expression in *Xenopus* oocytes," *Nucleic Acids Research* 26(21):4860-4867, 1998.

Banerjee et al., "Interaction of picornavirus 2C polypeptide with the viral negative-strand RNA," *Journal of General Virology* 82:2621-2627, 2001.

Banerjee et al., "Specific Interaction of Hepatitis C Virus Protease/Helicase NS3 with the 3'-Terminal Sequences of Viral Positive- and Negative-Strand RNA," *Journal of Virology* 75(4):1708-1721, Feb. 2001.

Banerjee et al., "Poliovirus-Encoded 2C Polypeptide Specifically Binds to the 3'-Terminal Sequences of Viral Negative-Strand RNA," *Journal of Virology* 71(12):9570-9578, Dec. 1997.

Banerjee et al., "Interaction of Poliovirus-Encoded 2C/2BC Polypeptides with the 3' Terminus Negative-Strand Cloverleaf Requires an Intact Stem-Loop b," *Virology* 280:41-51, 2001.

Bao et al., "The Influenza Virus Resource at the National Center for Biotechnology Information," *Journal of Virology* 82(2):596-601, Jan. 2008.

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras," *Proc. Natl. Acad. Sci. USA* 95:11047-11052, Sep. 1998.

Basler et al., "The Ebola virus VP35 protein functions as a type I IFN antagonist," *Proc. Natl. Acad. Sci. USA* 97(22):12289-12294, Oct. 24, 2000.

Berge et al., "Pharmaceutical Salts," *Journal of Pharmaceutical Sciences* 66(1):1-18, Jan. 1977.

Bernstein et al., "Role for a bidentate ribonuclease in the initiation step of RNA interference," *Nature* 409:363-366, Jan. 18, 2001.

Blommers et al., "An approach to the structure determination of nucleic acid analogues hybridized to RNA. NMR studies of a duplex between 2'-OMe RNA and an oligonucleotide containing a single amide backbone modification," *Nucleic Acids Research* 22(20):4187-4194, 1994.

Bonham et al., "An assessment of the antisense properties of RNase H-competent and steric-blocking oligomers," *Nucleic Acids Research* 23(7):1197-1203, 1995.

Borio et al., "Hemorrhagic Fever Viruses as Biological Weapons—Medical and Public Health Management," *JAMA* 287(18):2391-2405, May 8, 2002.

Boudvillain et al., "Transplatin-Modified Oligo(2'-*O*-methyl ribonucleotide)s: A New Tool for Selective Modulation of Gene Expression," *Biochemistry* 36:2925-2931, 1997.

Branch, "A good antisense molecule is hard to find," *Trends Biochem. Sci.* 23:45-50, Feb. 1998.

Brasey et al., "The Leader of Human Immunodeficiency Virus Type 1 Genomic RNA Harbors an Internal Ribosome Entry Segment That Is Active during the $G_2$/M Phase of the Cell Cycle," *Journal of Virology* 77(7):3939-3949, Apr. 2003.

Bray et al., "A Mouse Model for Evaluation of Prophylaxis and Therapy of Ebola Hemorrhagic Fever," *The Journal of Infectious Diseases* 178:651-661, Sep. 1998.

Burgin et al., "Chemically Modified Hammerhead Ribozymes with Improved Catalytic Rates," *Biochemistry* 35:14090-14097, 1996.

Burnett et al., "The Evolving Field of Biodefence: Therapeutic Developments and Diagnostics," *Nature Reviews* 4:281-297, Apr. 2005.

Buzayan et al., "Satellite tobacco ringspot virus RNA: A subset of the RNA sequence is sufficient for autolytic processing," *Proc. Natl. Acad. Sci. USA* 83:8859-8862, Dec. 1986.

Callahan et al., "Molecular cloning and complete sequence determination of RNA genome of human rhinovirus type 14," *Proc. Natl. Acad. Sci. USA* 82:732-736, Feb. 1985.

Chirila et al., "The use of synthetic polymers for delivery of therapeutic antisense oligodeoxynucleotides," *Biomaterials* 23:321-342, 2002.

Clarke et al., "Organization and Expression of Calicivirus Genes," *The Journal of Infectious Diseases* 181(Suppl. 2):S309-S316, 2000.

Connolly et al., "Pathogenesis of Experimental Ebola Virus Infection in Guinea Pigs," *The Journal of Infectious Diseases* 179(Suppl. 1):S203-S217, 1999.

(56) References Cited

OTHER PUBLICATIONS

Corey et al., "Morpholino antisense oligonucleotides: tools for investigating vertebrate development," *Genome Biology* 2(5):1015.1-1015.3, Apr. 26, 2001.
Cox et al., "Influenza," *The Lancet* 354:1277-1282, Oct. 9, 1999.
Cox et al., "Global Epidemiology of Influenza: Past and Present," *Annu. Rev. Med.* 51:407-421, 2000.
Crooke et al., "In Vitro Toxicological Evaluation of ISIS 1082, a Phosphorothioate Oligonucleotide Inhibitor of Herpes Simplex Virus," *Antimicrobial Agents and Chemotherapy* 36(3):527-532, Mar. 1992.
Crooke, "Basic Principles of Antisense Therapeutics," in Stanley T. Crooke (ed.), *Antisense Research and Application*, Springer-Verlag, Berlin, Germany, 1998, pp. 1-50.
Crooke et al., "Pharmacokinetic Properties of Several Novel Oligonucleotide Analogs in mice," *The Journal of Pharmacology and Experimental Therapeutics* 277(2):923-937, 1996.
Cross et al., "Solution Structure of an RNA-DNA Hybrid Duplex Containing a 3'-Thioformacetal Linker and an RNA A-Tract," *Biochemistry* 36:4096-4107, 1997.
Dagle et al., "Targeted elimination of zygotic messages in *Xenopus laevis* embryos by modified oligonucleotides possessing terminal cationic linkages," *Nucleic Acids Research* 28(10):2153-2157, 2000.
Database WPI, Week 199942, Thomson Scientific, London, GB, Accession No. 1999-494850, 1 page.
Deas et al, "Inhibition of Flavivirus Infections by Antisense Oligomers Specifically Suppressing Viral Translation and RNA Replication," *Journal of Virology* 79(8):4599-4609, Apr. 2005.
Devereux et al., "A comprehensive set of sequence analysis programs for the VAX," *Nucleic Acids Research* 12(1):387-395, 1984.
Ding et al., "An oligodeoxyribonucleotide N3'→P5' phosphoramidate duplex forms an A-type helix in solution," *Nucleic Acids Research* 24(2):354-360, 1996.
Dordunoo et al., "Preformulation studies on solid dispersions containing triamterene or temazepam in polyethylene glycols or gelucire 44/14 for liquid filling of hard gelatin capsules," *Drug Development and Industrial Pharmacy* 17(12):1685-1713, 1991.
Egholm et al., "PNA hybridizes to complementary oligonucleotides obeying the Watson-Crick hydrogen-bonding rules," *Nature* 365:566-568, Oct. 7, 1993.
Emerich et al., "Biocompatibility of Poly (DL-Lactide-*co*-Glycolide) Microspheres Implanted Into the Brain," *Cell Transplantation* 8:47-58, 1999.
Extended European Search Report, for European Application No. 05796604.6, dated Jan. 13, 2009, 7 pages.
Extended European Search Report, for European Application No. 05824730.5, dated Jul. 30, 2010, 24 pages.
Faria et al., "Phosphoramidate oligonucleotides as potent antisense molecules in cells and in vivo," *Nature Biotechnology* 19:40-44, Jan. 2001.
Feldmann et al., "Molecular biology and evolution of filoviruses," *Arch Virol* 7(Suppl.):81-100, 1993.
Feldmann et al., "Classification, Structure, and Replication of Filovirus," *Curr. Top. Micorbiol. Immunol.* 235:1-21, 1999.
Feldmann et al., "Ebola virus: from discovery to vaccine," *Nature Reviews* 3:677-685, Aug. 2003.
Felgner et al., "Lipofection: A highly efficient, lipid-mediated DNA-transfection procedure," *Proc. Natl. Acad. Sci. USA* 84:7413-7417, Nov. 1987.
Finlay et al., "Anti-Immunology: Evasion of the Host Immune System by Bacterial and Viral Pathogens," *Cell* 124: 767-782, Feb. 24, 2006.
Fischer, "Cellular Uptake Mechanisms and Potential Therapeutic Utility of Peptidic Cell Delivery Vectors: Progress 2001-2006," *Medical Research Reviews* 27:755-795, 2007.
Forster et al., "Self-Cleavage of Virusoid RNA Is Performed by the Proposed 55-Nucleotide Active Site," *Cell* 50:9-16, Jul. 3, 1987.

Freier, "Methods of Selecting Sites in RNA for Antisense Targeting," in Stanley T. Crooke (ed.), *Antisense Drug Technology: Principles, Strategies, and Applications*, Marcel Dekker, Inc., New York, 2001, pp. 107-118.
Gabriel et al., "Morpholino oligomers targeting the PB1 and NP genes enhance the survival of mice infected with highly pathogenic influenza A H7N7 virus," *Journal of General Virology* 89:939-948, 2008.
Gait et al., "Synthetic Analogues of Polynucleotides. Part XII. Syntheis of Thymidine Derivatices containing an Oxyacetamido- or an Oxyformamido-linkage instead of a Phosphodiester Group," *J. Chem. Soc. Perkin I 0*(14):1684-1686, 1974.
Ge et al., "Inhibition of Multiple Subtypes of Influenza A Virus in Cell Cultures with Morpholino Oligomers," *Antimicrobial Agents and Chemotherapy 50*(11):3724-3733, Nov. 2006.
Gee et al., "Assessment of High-Affinity Hybridization, RNase H Cleavage, and Covalent Linkage in Translation Arrest by Antisense Oligonucleotides," *Antisense & Nucleic Acid Drug Development 8*:103-111, 1998.
Geisbert et al., "Treatment of Ebola virus infection with a recombinant inhibitor of factor VIIa/tissue factor: a study in rhesus monkeys," *The Lancet 362*:1953-1958, Dec. 13, 2003.
Geisbert et al., "Ebola virus: new insights into disease aetiopathology and possible therapeutic interventions," *Expert Reviews in Molecular Medicine 6*(20):1-24, Sep. 21, 2004.
Gilbert et al., "Sieve analysis: methods for assessing from vaccine trial data how vaccine efficacy varies with genotypic and phenotypic pathogen variation," *Journal of Clinical Epidemiology 54*:68-85, 2001.
Green et al., "Antisense Oligonucleotides: An Evolving Technology for the Modulation of Gene Expression in Human Disease," *Journal of the American College of Surgeons 191*(1):93-105, 2000.
Hames et al., *Nucleic acid hybridisation: a practical approach*, IRL Press, Oxford, England, 1985, pp. 107-108, 12 pages.
Hanecak et al., "Antisense Oligonucleotide Inhibition of Hepatitis C Virus Gene Expression in Transformed Hepatocytes," *Journal of Virology 70*(8):5203-5212, Aug. 1996.
Hanson, "Oligonucleotide Analogues Having Modified Intersubunit Linkages," U.S. Appl. No. 61/349,783, filed May 28, 2010, 85 pages.
Hanson, "Oligonucleotide Analogues Having Modified Terminal Groups," U.S. Appl. No. 61/361,878, filed Jul. 6, 2010, 82 pages.
Hatherley et al., "The CD200 and CD200 receptor cell surface proteins interact through their N-terminal immunoglobulin-like domains," *Eur. J. Immunol. 34*:1688-1694, 2004.
Holland, "Replication Error, Quasispecies Populations, and Extreme Evolution Rates of RNA Viruses," in Stephen S. Morse (ed.), *Emerging Viruses*, Oxford University Press, New York, 1993, pp. 203-218, 18 pages.
Hudziak et al., "Resistance of Morpholino Phosphorodiamidate Oligomers to Enzymatic Degradation," *Antisense & Nucleic Acid Drug Development 6*:267-272, 1996.
Huffman et al., "Influenza Virus-Inhibitory Activity of a Series of Antisense Oligonucleotides," *Antiviral Research 20*(Suppl. 1):152, Abstract No. 201, 1993.
International Search Report, for International Application No. PCT/US2005/038780, mailed Jul. 12, 2006, 5 pages.
International Search Report, for International Application No. PCT/US2007/011435, mailed Sep. 29, 2008, 5 pages.
International Search Report, for International Application No. PCT/US2010/056613, mailed Apr. 21, 2011, 6 pages.
Ishiwata et al., "Physical-Chemistry Characteristics and Biodistribution of Poly(ethylene glycol)-Coated Liposomes Using Poly(oxyethylene) Cholesteryl Ether," *Chem. Pharm. Bull. 43*(6):1005-1011, 1995.
Iversen et al., "Antisense Antiviral Compounds and Methods for Treating a Filovirus Infection," U.S. Appl. No. 12/853,180, filed Aug. 9, 2010, 108 pages.
Iversen, "Antisense Antiviral Compound and Method for Treating Influenza Viral Infection," U.S. Appl. No. 61/261,278, filed Nov. 13, 2009, 115 pages.
Iversen, "Antisense Antiviral Compound and Method for Treating Influenza Viral Infection," U.S. Appl. No. 61/292,056, filed Jan. 4, 2010, 125 pages.

(56) References Cited

OTHER PUBLICATIONS

Iversen, "Antisense Antiviral Compund and Method for Treating Influenza Viral Infection," U.S. Appl. No. 61/377,382, filed Aug. 26, 2010, 137 pages.

Iversen et al., "Antisense Antiviral Compounds and Methods for Treating a Filovirus Infection," International Application No. PCT/US2010/046234, filed Aug. 20, 2010, 113 pages.

Jaeger et al., "Improved predictions of secondary structures for RNA," *Proc. Natl. Acad. Sci. USA* 86:7706-7710, Oct. 1989.

Jahrling et al., "Evaluation of Immune Globulin and Recombinant Interferon-α2b for Treatment of Experimental Ebola Virus Infections," *The Journal of Infectious Diseases* 179(Suppl. 1):S224-S234, 1999.

Jain et al., "Hospitalized Patients with 2009 H1N1 Influenza in the United States, Apr.-Jun. 2009," *The New England Journal of Medicine* 361:1935-1944, Apr.-Jun. 2009.

Jamieson et al., "Influenza Virus-Induced Glucocorticoids Compromise Innate Host Defense against a Secondary Bacterial Infection," *Cell Host & Microbe* 7:103-114, Feb. 18, 2010.

Jean et al., "Invasive Group a Streptococcal Infection Concurrent with 2009 H1N1 Influenza," *Clinical Infectious Diseases* 50(10):e59-e62, May 15, 2010.

Jearawiriyapaisarn et al., "Sustained Dystrophin Expression Induced by Peptide-conjugated Morpholino Oligomers in the muscles of *mdx* Mice," *Mol. Ther.* 16(9):1624-1629, Sep. 2008.

Jen et al., "Suppression of Gene Expression by Targeted Disruption of Messenger RNA: Available Options and Current Strategies," *Stem Cells* 18:307-319, 2000.

Johannes et al., "Identification of eukaryotic mRNAs that are translated at reduced cap binding complex eIF4F concentrations using a cDNA microarray," *Proc. Natl. Acad. Sci. USA* 96(23):13118-13123, Nov. 9, 1999.

Jubin et al., "Hepatitis C Virus Internal Ribosome Entry Site (IRES) Stem Loop IIId Contains a Phylogenetically Conserved GGG Triplet Essential for Translation and IRES Folding," *Journal of Virology* 74(22):10430-10437, Nov. 2000.

Kabanov et al., "A new class of antivirals: antisense oligonucleotides combined with a hydrophobic substituent effectively inhibit influenza virus reproduction and synthesis of virus-specific proteins in MDCK cells," *FEBS Lett.* 259(2):327-330, Jan. 1990.

Kinney et al, "Inhibition of Dengue Virus Serotypes 1 to 4 in Vero Cell Cultures with Morpholino Oligomers," *Journal of Virology* 79(8):5116-5128, Apr. 2005.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* 54:3607-3630, 1998.

Lappalainen et al., "Cationic liposomes mediated delivery of antisense oligonucleotides targeted to HPV 16 E7 mRNA in CaSki cells," *Antiviral Research* 23:119-130, 1994.

Lasic et al., "Liposomes Revisited," *Science* 267:1275-1276, Mar. 3, 1995.

Lasic et al., "The "Stealth"Liposome: A Prototypical Biomaterial," *Chemical Reviews* 95(8):2601-2628, Dec. 1995.

Lee et al., "Complete Sequence of the RNA Genome of Human Rhinovirus 16, a clinically Useful Common Cold Virus Belonging to the ICAM-1 Receptor Group," *Virus Genes* 9(2):177-181, 1994.

Lee et al., "The C. elegans Heterochronic Gene *lin-4* Encodes Small RNAs with Antisense Complementarity to *lin-14*," *Cell* 75:843-854, Dec. 3, 1993.

Lesnikowski et al., "Octa(thymidine methanephosphonates) of partially defined stereochemistry: synthesis and effect of chirality at phosphorus on binding to pentadecadeoxyriboacdenylic acid," *Nucleic Acids Research* 18(8):2109-2115, 1990.

Letsinger et al., "Cholesteryl-conjugated oligonucleotides: Synthesis, properties, and activity as inhibitors of replication of human immunodeficiency virus in cell culture," *Proc. Natl. Acad. Sci. USA* 86:6553-6556, Sep. 1989.

Linkletter et al., "Solid-phase Synthesis of Positively Charged Deoxynucleic Guanidine (DNG) Modified Oligonucleotides Containing Neutral Urea Linkages: Effect of Charge Deletions on Binding and Fidelity," *Bioorganic & Medicinal Chemistry* 8:1893-1901, 2000.

Liu et al., "Cationic Liposome-mediated Intravenous Gene Delivery," *The Journal of Biological Chemistry* 270(42):24864-24870, Oct. 20, 1995.

Liu et al., "Structural and Functional Analysis of the 5' Untranslated Region of Coxsackievirus B3 RNA: In Vivo Translational and Infectivity Studies of Full-Length Mutants," *Virology* 265:206-217, 1999.

López de Quinto et al., "Involvement of the Aphthovirus RNA Region Located between the Two Functional AUGs in Start Codon Selection," *Virology* 255:324-336, 1999.

Manoharan et al., "Chemical Modifications to Improve Uptake and Bioavailability of Antisense Oligonucleotides," *Annals of the New York Academy of Sciences* 660:306-309, 1992.

Manoharan et al., "Cholic Acid-Oligonucleotide Conjugates for Antisense Applications," *Bioorganic & Medicinal Chemistry Letters* 4(8):1053-1060, 1994.

Manoharan et al., "Introduction of a Lipophilic Thioether Tether in the Minor Groove of Nucleic Acids for Antisense Applications," *Bioorganic & Medicinal Chemistry Letters* 3(12):2765-2770, 1993.

Manoharan et al., "Lipidic Nucleic Acids," *Tetrahedron Letters* 36(21):3651-3654, 1995.

Manoharan et al., "Oligonucleotide Conjugates: Alteration of the Pharmacokinetic Properties of Antisense Agents," *Nucleosides & Nucleotides* 14(3-5):969-973, 1995.

Markoff, "5'- and 3'-Noncoding Regions in Flavivirus RNA," *Advances in Virus Research* 59:177-228, 2003.

Marshall et al., "Arginine-rich cell-penetrating peptides facilitate delivery of antisense oligomers into murine leukocytes and alter pre-mRNA splicing," *Journal of Immunological Methods* 325:114-126, 2007.

McCaffrey et al., "A Potent and Specific Morpholino Antisense Inhibitor of Hepatitis C Translation in Mice," *Hepatology* 38:503-508, Aug. 2003.

Mertes et al., "Synthesis of Carbonate Analogs of Dinucleosides. 3'-Thymidinyl 5'Thymidinyl Carbonate, 3'-Thymidinyl 5'-(5-Fluoro-2'-deoxyuridinyl) Carbonate, and 3'-(5-Fluoro-2'-deoxyuridinyl) 5'-Thymidinyl Carbonate," *J. Med. Chem.* 12(1):154-157, 1969.

Micklefield, "Backbone Modification of Nucleic Acids: Synthesis, Structure and Therapeutic Applications," *Current Medicinal Chemistry* 8:1157-1179, 2001.

Miranda et al., "Differential activation of apoptosis regulatory pathways during monocytic vs granulocytic differentiation: a requirement of Bcl-$X_L$ and XIAP in the prolonged survival of monocytic cells," *Leukemia* 17:390-400, 2003.

Mishra et al., "Improved leishmanicidal effect of phosphorotioate antisense oligonucleotides by LDL-mediated delivery," *Biochimica et Biophysica Acta* 1264:229-237, 1995.

Miyada et al., "[6] Oligonucleotide Hybridization Techniques," *Methods in Enzymology* 154:94-107, 1987.

Mizuta et al., "Antisense oligonucleotides directed against the viral RNA polymerase gene enhance survival of mice infected with influenza A," *Nature Biotechnology* 17:583-587, Jun. 1999.

Moulton et al., "Cellular Uptake of Antisense Morpholino Oligomers Conjugated to Arginine-Rich Peptides," *Bioconjugate Chem.* 15:290-299, 2004.

Moulton et al., "Compound and Method for Treating Myotonic Dystrophy," U.S. Appl. No. 13/219,401, filed Aug. 26, 2011, 98 pages.

Moulton et al., "Delivery of Antisense Phosphorodiamidate Morpholino Oligomers by Arginine-Rich Peptides," 226th ACE National Meeting, American Chemical Society, Abstracts of Papers Part 1, Abstract No. 75, New York, NY, Sep. 7-11, 2003, 2 pages.

Moulton et al., "HIV Tat Peptide Enhances Cellular Delivery of Antisense Morpholino Oligomers," *Antisense and Nucleic Acid Drug Development* 13:31-43, 2003.

Moulton et al., "Peptide-assisted delivery of steric-blocking antisense oligomers," *Current Opinion in Molecular Therapeutics* 5(2):123-132, 2003.

Munster et al., "Pathogenesis and Transmission of Swine-Origin 2009 A(H1N1) Influenza Virus in Ferrets," *Science* 325:481-483, Jul. 24, 2009.

(56) References Cited

OTHER PUBLICATIONS

NCBI Database Accession No. AF029248, retrieved Jul. 25, 2007, from http://www.ncbi.nlm.nih.gov/entrez/viewer.fcgi?db=nuccore&id=2641127, 7 pages.
NCBI Database Accession No. AF091736, retrieved May 19, 2009, from http://www.ncbi.nlm.nih.gov/nuccore/3661574, 5 pages.
NCBI Database Accession No. AF169005, retrieved May 19, 2009, from http://www.ncbi.nlm.nih.gov/nuccore/6707285?ordinalpos=1&itool=EntrezSystem2.PEntr . . . , 5 pages.
NCBI Database Accession No. AF304460, retrieved Jul. 25, 2007, from http://www.ncbi.nlm.nih.gov/entrez/viewer.fcgi?db=nuccore&id=12082738, 14 pages.
NCBI Database Accession No. AY274119, retrieved Jul. 25, 2007, from http://www.ncbi.nlm.nih.gob/entrez/viewer.fcgi?db=nuccore&id=30248028, 14 pages.
NCBI Database Accession No. NC_002645, retrieved Jul. 25, 2007, from http://www.ncbi.nlm.nih.gob/entrez/viewer.fcgi?db=nuccore&id=12175745, 16 pages.
Nelson et al., "Arginine-Rich Peptide Conjugation to Morpholino Oligomers: Effects on Antisense Activity and Specificity," *Bionconjugate Chem.* 16:959-966, 2005.
Neuman et al., "Antisense Morpholino-Oligomers Directed against the 5' End of the Genome Inhibit Coronavirus Proliferation and Growth," *Journal of Virology* 78(11):5891-5899, Jun. 2004.
Nielsen et al., "Sequence-Selective Recognition of DNA by Strand Displacement with a Thymine-Substituted Polyamide," *Science* 254:1497-1500, Dec. 6, 1991.
O'Ryan et al., "Rotavirus, Enteric Adenoviruses, Norwalk Virus, and Other Gastroenteritis Tract Viruses," in Steven Specter et al. (eds.), *Clinical Virology Manual*, Second Edition, Elsevier, New York, 1992, pp. 361-396.
Oberhauser et al., "Effective incorporation of 2'-O-methyl-oligonucleotides into liposomes and enhanced cell association through modification with thiocholesterol," *Nucleic Acids Research* 20(3):533-538, 1992.
Obika et al., "Stability and structural features of the duplexes containing nucleoside analogues with a fixed N-type conformation, 2'-O,4'-C-methyleneribonucleosides," *Tetrahedron Letters* 39:5401-5404, 1998.
Obika et al., "Synthesis and properties of 3'-amino-2',4'-BNA, a bridged nucleic acid with a N3'→P5' phosphoramidate linkage," *Bioorganic & Medicinal Chemistry* 16:9230-9237, 2008.
Obika et al., "Synthesis of 2'-O,4'-C-Methyleneuridine and -cytidine. Novel Bicyclic Nucleosides Having a Fixed $C_3$-endo Sugar Puckering," *Tetrahedron Letters* 38(50):8735-8738, 1997.
Oku et al, "Real-time analysis of liposomal trafficking in tumor-bearing mice by use of positron emission tomography," *Biochimica et Biophysica Acta* 1238:86-90, 1995.
Orr et al., "Patent review: Therapeutic applications for antisense oligonucleotides 1999-2000," *Current Opinion in Molecular Therapeutics* 2(3):325-331, 2000.
Palù et al., "In pursuit of new developments for gene therapy of human diseases," *Journal of Biotechnology* 68:1-13, 1999.
Pardigon et al., "Cellular Proteins Bind to the 3' End of Sindbis Virus Minus-Strand RNA," *Journal of Virology* 66(2):1007-1015, 1992.
Pardigon et al., "Multiple Binding Sites for Cellular Proteins in the 3' End of the Sindbis Alphavirus Minus-Sense RNA," *Journal of Virology* 67(8):5003-5011, 1993.
Pari et al., "Potent Antiviral Activity of an Antisense Oligonucleotide Complementary to the Intron-Exon Boundary of Human Cytomegalovirus Genes UL36 and UL37," *Antimicrobial Agents and Chemotherapy* 39(5):1157-1161, 1995.
Partridge et al., "A Simple Method for Delivering Morpholino Antisense Oligos into the Cyctoplasm of Cells," *Antisense & Nucleic Acid Drug Development* 6:169-175, 1996.
Paul, "Possible Unifying Mechanism of Picornavirus Genome Replication," in B.L. Semler et al. (eds.), *Molecular Biology of Picornaviruses*, ASM Press, Washington D.C., 2002, pp. 227-246.
Peters et al., "An Introduction to Ebola: The Virus and the Disease," *The Journal of Infectious Diseases* 179(Suppl. 1):ix-xvi, 1999.

Raviprakash et al., "Inhibition of Dengue Virus by Novel, Modified Antisense Oligonucleotides," *Journal of Virology* 69(1):69-74, 1995.
Reinhart et al., "The 21-nucleotide *let*-7 RNA regulates developmental timing in *Caenorhabditis elegans*," *Nature* 403:901-906, Feb. 24, 2000.
Robaczewska et al., "Inhibition of hepadnaviral replication by polyethylenimine-based intravenous delivery of antisense phosphodiester oligodeoxynucleotides to the liver," *Gene Therapy* 8:874-881, 2001.
Roehl et al., "Poliovirus Infection Enhances the Formation of Two Ribonucleoprotein Complexes at the 3' End of Viral Negative-Strand RNA," *Journal of Virology* 69(5):2954-2961, 1995.
Roehl et al., "Processing of a Cellular Polypeptide by 3CD Proteinase Is Required for Poliovirus Ribonucleoprotein Complex Formation," *Journal of Virology* 71(1):578-585, 1997.
Rothbard et al., "Arginine-Rich Molecular Transporters for Drug Delivery: Role of Backbone Spacing in Cellular Uptake," *J. Med. Chem.* 45:3612-3618, 2002.
Ruvkun, "Glimpses of a Tiny RNA World," *Science* 294:797-799, 2001.
Saison-Behmoaras et al., "Short modified antisense oligonucleotides directed against Ha-*ras* point mutation induce selective cleavage of the mRNA and inhibit T24 cells proliferation," *The EMBO Journal* 10(5):1111-1118, 1991.
Sanchez et al., "Sequence analysis of the Ebola virus genome: organization, genetic elements, and comparison with the genome of Marburg virus," *Virus Research* 29:215-240, 1993.
Sankar et al., "Antisense oligonucleotide inhibition of encephalomyocarditis virus RNA translation," *Eur. J. Biochem.* 184:39-45, 1989.
Scanlon, "Anti-Genes: siRNA, Ribozymes and Antisense," *Current Pharmaceutical Biotechnology* 5:415-420, 2004.
Schroeder et al., "Diffusion enhancement of drugs by loaded nanoparticles in vitro," *Prog. Neuro-Psychopharmacol. & Biol. Psychiat.* 23:941-949, 1999.
Shabbits et al., "Tumor Chemosensitization Strategies Based on Apoptosis Manipulations," *Molecular Cancer Therapeutics* 2:805-813, 2003.
Shea et al., "Synthesis, hybridization properties and antiviral activity of lipid-oligodeoxynucleotide conjugates," *Nucleic Acids Research* 18(13):3777-3783, 1990.
Sheen et al., "Bioavailability of a Poorly Water-Soluble Drug from Tablet and Solid Dispersion in Humans," *Journal of Pharmaceutical Sciences* 80(7):712-714, 1991.
Shengqi et al., "Synthesis of Antisense Phosphothioate Oligodeoxynucleotides of Dengue Fever Virus and Their Anti-viral Activity," *Progress of Biochemistry and Biophysics* 24(1):64-68, 1997. (with English Translation).
Singh et al., "LNA (locked nucleic acids): synthesis and high-affinity nucleic acid recognition," *Chem. Commun.*:455-456, 1998.
Siprashvili et al., "Gene Transfer via Reversible Plasmid Condensation with Cysteine-Flanked, Internally Spaced Arginine-Rich Peptides," *Human Gene Therapy* 14:1225-1233, 2003.
Smith et al., "Antisense treatment of *Caliciviridae*: An emerging disease agent of animals and humans," *Current Opinion in Molecular Therapeutics* 4(2):177-184, 2002.
Smith et al., "Calicivirus Emergence from Ocean Reservoirs: Zoonotic and Interspecies Movements," *Emerging Infectious Diseases* 4(1):13-20, 1998.
Smith et al., "Secondary structure and hybridization accessibility of the hepatitis C virus negative strand RNA 5'-terminus," *Journal of Viral Hepatitis* 11:115-123, 2004.
Sosnovtsev et al., "RNA Transcripts Derived from a Cloned Full-Length Copy of the Feline Calicivirus Genome Do Not Require VpG for Infectivity," *Virology* 210:383-390, 1995.
Stein et al., "Antisense Antiviral Compound and Method for Treating Influenza Viral Infection," U.S. Appl. No. 60/622,077, filed Oct. 26, 2004, 50 pages.
Stein et al., "A Specificity Comparison of Four Antisense Types: Morpholino, 2'-O-Methyl RNA, DNA, and Phosphorothioate DNA," *Antisense & Nucleic Acid Drug Delivery* 7:151-157, 1997.

(56) References Cited

OTHER PUBLICATIONS

Stein et al., "Efficient gene silencing by delivery of locked nucleic acid antisense oligonucleotides, unassisted by transfection reagents," *Nucleic Acids Research* 38(1):e3, 2010. (8 pages).

Stein et al., "Inhibition of Vesivirus Infections in Mammalian Tissue Culture with Antisense Morpholino Oligomers," *Antisense & Nucleic Acid Drug Development* 11:317-325, 2001.

Sui et al., "Small Interfering RNA Targeting M2 Gene Induces Effective and Long Term Inhibition of Influenza A Virus Replication," *PLoS One* 4(5):e5671, 2009. (7 pages).

Summerton et al., "Morpholino and Phosphorothioate Antisense Oligomers Compared in Cell-Free and In-Cell Systems," *Antisense & Nucleic Acid Drug Development* 7:63-70, 1997.

Summerton et al., "Morpholino Antisense Oligomers: Design, Preparation, and Properties," *Antisense & Nucleic Acid Drug Development* 7:187-195, 1997.

Summerton et al., "Morpholino antisense oligomers: the case for an RNase H-independent structural type," *Biochimica et Biophysica Acta* 1489:141-158, 1999.

Svinarchuk et al., "Inhibition of HIV proliferation in MT-4 cells by antisense oligonucleotide conjugated to lipophilic groups," *Biochimie* 75:49-54, 1993.

Swenson et al., "Chemical Modifications of Antisense Morpholino Oligomers Enhance Their Efficacy against Ebola Virus Infection," *Antimicrob Agents Chemother* 53(5): 2089-2099, May 2009.

Taylor et al., "Antisense oligonucleotides: a systematic high-throughput approach to target validation and gene function determination," *Drug Discovery Today* 4(12):562-567, 1999.

Thiel et al., "Infectious RNA transcribed in vitro from a cDNA copy of the human coronavirus genome cloned in vaccinia virus," *Journal of General Virology* 82:1273-1281, 2001.

Toulmé et al., "Targeting RNA structures by antisense oligonucleotides," *Biochimie* 78:663-673, 1996.

Uhlmann et al., "Antisense Oligonucleotides: A New Therapeutic Principle," *Chemical Reviews* 90(4):543-584, 1990.

Vlassov et al., "Inhibition of the Influenza Virus M Protein mRNA Translation in vitro with Complementary Oligonucleotides," *Nucleosides & Nucleotides* 10(1-3):649-650, 1991.

Wages, Jr. et al., "Affinity Purification of RNA: Sequence-Specific Capture by Nonionic Morpholino Probes," *BioTechniques* 23(6):1116-1121, 1997.

Wang et al., "Specific Inhibition of Coxsackievirus B3 Translation and Replication by Phosphorothioate Antisense Oligodeoxynucleotides," *Antimicrobial Agents and Chemotherapy* 45(4):1043-1052, 2001.

Warfield et al., "Role of Natural Killer Cells in Innate Protection against Lethal Ebola Virus Infection," *The Journal of Experimental Medicine* 200(2):169-179, 2004.

Wei et al., "Human immunodeficiency virus type-1 reverse transcription can be inhibited in vitro by oligonucleotides that target both natural and synthetic tRNA primers," *Nucleic Acids Research* 28(16):3065-3074, 2000.

Weller et al., "Oligonucleotide Analogs Having Cationic Intersubunit Linkages," U.S. Appl. No. 13/049,770, filed Mar. 16, 2011, 174 pages.

Wengel, "Synthesis of 3'-C- and 4'-C-Branched Oligodeoxynucleotides and the Development of Locked Nucleic Acid (LNA)," *Acc. Chem. Res.* 32(4):301-310, 1999.

Wenz, "Cyclodextrins as Building Blocks for Supramolecular Structures and Functional Units," *Angew. Chem. Int. Ed. Engl.* 33:803-822, 1994.

Williams et al., "A Single Intra-Articular Injection of Liposomally Conjugated Methotrexate Suppresses Joint Inflammation in Rat Antigen-Induced Arthritis," *British Journal of Rheumatology* 35:719-724, 1996.

Williams et al., "Cationic lipids reduce time and dose of c-myc antisense oligodeoxynucleotides required to specifically inhibit Burkitt's lymphoma cell growth," *Leukemia* 10:1980-1989, 1996.

Wilson et al., "Naturally Occurring Dicistronic Cricket Paralysis Virus RNA Is Regulated by Two Internal Ribosome Entry Sites," *Molecular and Cellular Biology* 20(14):4990-4999, 2000.

Winter et al., "Nucleotide sequence of human influenza A/PR/8/34 segment 2," *Nucleic Acids Research* 10(6):2135-2143, 1982.

Written Opinion for International Application No. PCT/US2005/038780, mailed Jul. 12, 2006, 4 pages.

Written Opinion for International Application No. PCT/US2007/011435, mailed Sep. 29, 2008, 5 pages.

Written Opinion for International Application No. PCT/US2010/056613, mailed Apr. 21, 2011, 9 pages.

Wu et al., "Effective rescue of dystrophin improves cardiac function in dystrophin-deficient mice by a modified morpholino oligomer," *Proc. Natl. Acad. Sci. USA* 105(39):14814-14819, 2008.

Wu et al., "Receptor-mediated in Vitro Gene Transformation by a Soluble DNA Carrier System," *The Journal of Biological Chemistry* 262(10):4429-4432, 1987.

Wu et al., "Specific Inhibition of Hepatitis B Viral Gene Expression in Vitro by Targeted Antisense Oligonucleotides," *The Journal of Biological Chemistry* 267(18):12436-12439, 1992.

Xu et al., "Viral haemorrhagic disease of rabbits in the People's Republic of China: epidemiology and virus characterisation," *Rev. sci. tech. Off. Int. Epiz.* 10(2):393-408, 1991.

Yuan et al., "A phosphorothioate antisense oligodeoxynucleotide specifically inhibits coxsackievirus B3 replication in cardiomyocytes and mouse hearts," *Laboratory Investigation* 84:703-714, 2004.

Zhang et al., "Antisense Oligonucleotide Inhibition of Hepatitis C Virus (HCV) Gene Expression in Livers of Mice Infected with an HCV-Vaccinia Virus Recombinant," *Antimicrobial Agents and Chemotherapy* 43(2):347-353, 1999.

Zhou et al., "Effective small interfering RNAs targeting matrix and nucleocapsid protein gene influenza A virue replication in cells and mice," *Antiviral Research* 76:186-193, 2007.

Zollinger et al., "Meningococcal vaccines—present and future," *Transactions of the Royal Society of Tropical Medicine and Hygiene* 85(Suppl. 1):37-43, 1991.

Zuker, "Mfold web server for nucleic acid folding and hybridization prediction," *Nucleic Acids Research* 31(13):3406-3415, 2003.

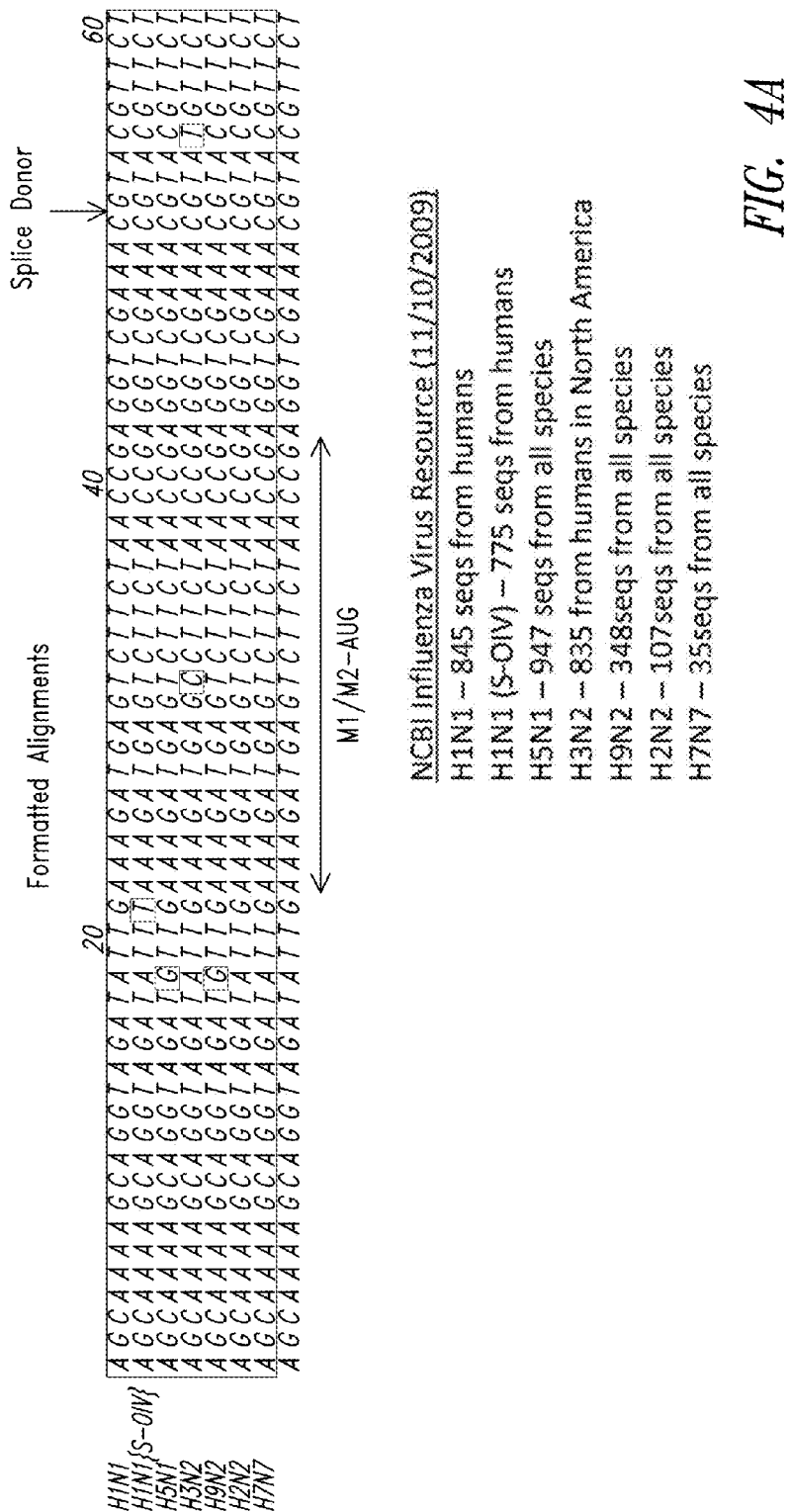

M1/M2 Dose-Dependent reduction in viral titer

H3N2 Mouse Model

- M1/M2 (SEQ ID NOs:12 & 13)
- PB1-AUG 15 (SEQ ID NOs:34 & 35)
- NP-v3' (SEQ ID NOs:32 & 33)
- Dengue

FIG. 6

2'O M2 viral load

FIG. 10A

ANTISENSE ANTIVIRAL COMPOUND AND METHOD FOR TREATING INFLUENZA VIRAL INFECTION

CROSS REFERENCE TO RELATED APPLICATIONS

This application is a continuation of U.S. application Ser. No. 12/945,081, filed Nov. 12, 2010 (allowed); which claims the benefit under 35 U.S.C. §119(e) of U.S. Provisional Patent Application No. 61/261,278, filed Nov. 13, 2009; U.S. Provisional Patent Application No. 61/292,056, filed Jan. 4, 2010; and U.S. Provisional Patent Application No. 61/377,382, filed Aug. 26, 2010, each of which is incorporated by reference in its entirety.

STATEMENT OF GOVERNMENT INTEREST

The invention was made with Government support under HDTRA1-09-C-0046 and HDTRA1-C-10-0079 awarded by Department of Defense. The Government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_456C1_SEQUENCE_LISTING.txt. The text file is 33 KB, was created on Feb. 28, 2014, and is being submitted electronically via EFS-Web.

FIELD OF THE INVENTION

The invention relates to antisense oligonucleotides for use in treating an influenza virus infection and antiviral treatment methods employing the oligonucleotides.

BACKGROUND OF THE INVENTION

Influenza viruses have been a major cause of human mortality and morbidity throughout recorded history. Influenza A virus infection causes millions of cases of severe illness and as many as 500,000 deaths each year worldwide. Epidemics vary widely in severity but occur at regular intervals and always cause significant mortality and morbidity, most frequently in the elderly population. Although vaccines against matched influenza strains can prevent illness in 60-80% of healthy adults, the rate of protection is much lower in high-risk groups. Furthermore, vaccination does not provide protection against unexpected strains, such as the H5 and H7 avian influenza outbreaks in Hong Kong in 1997 and Europe and Southeast Asia in 2003 and 2004. Current anti-influenza drugs are limited in their capacity to provide protection and therapeutic effect (Cox and Subbarao 1999; Cox and Subbarao 2000).

Influenza A is a segmented RNA virus of negative-polarity. Genome segments are replicated by a complex of 4 proteins: the 3 polymerase polypeptides (PA, PB1 and PB2) and NP (Nucleoprotein). The 5' and 3' terminal sequence regions of all 8 genome segments are highly conserved within a genotype (Strauss and Strauss 2002).

Influenza A viruses can be subtyped according to the antigenic and genetic nature of their surface glycoproteins; 15 hemagglutinin (HA) and 9 neuraminidase (NA) subtypes have been identified to date. Viruses bearing all known HA and NA subtypes have been isolated from avian hosts, but only viruses of the H1N1 (1918), H2N2 (1957/58), and H3N2 (1968) subtypes have been associated with widespread epidemics in humans (Strauss and Strauss 2002).

Since 1997, when H5N1 influenza virus was transmitted to humans and killed 6 of 18 infected persons, there have been multiple transmissions of avian influenza viruses to mammals. Either the whole virus is transmitted directly or gene segments from the avian influenza virus are acquired by mammalian strains. Widespread infections of poultry with H5N1 viruses in Asia have caused increasing concern that this subtype may achieve human-to-human spread and establish interspecies transmission. The species which different types of influenza viruses are able to infect are determined by different forms of the virus glycoproteins (HA, NA). This provides a considerable species barrier between birds and humans which is not easily overcome. Pigs, however, provide a "mixing pot"—able to be infected by both types of virus and thereby allowing the passage of avian viruses to humans. When an individual pig cell is co-infected with both avian and human influenza viruses, recombinant forms can emerge that carry an avian HA genotype but readily infect humans. Avian HA can infect pigs, but not humans. In pigs, during genome segment packaging, it is possible to create a virus with several Avian segments and Human HA and/or NA segments (Cox and Subbarao 2000).

Influenza viruses infect humans and animals (e.g., pigs, birds, horses) and may cause acute respiratory disease. There have been numerous attempts to produce vaccines effective against influenza virus. None, however, have been completely successful, particularly on a long-term basis. This may be due, at least in part, to the segmented characteristic of the influenza virus genome, which makes it possible, through re-assortment of the segments, for numerous forms to exist. For example, it has been suggested that there could be an interchange of RNA segments between animal and human influenza viruses, which would result in the introduction of new antigenic subtypes into both populations. Thus, a long-term vaccination approach has failed, due to the emergence of new subtypes (antigenic "shift"). In addition, the surface proteins of the virus, hemagglutinin and neuraminidase, constantly undergo minor antigenic changes (antigenic "drift"). This high degree of variation explains why specific immunity developed against a particular influenza virus does not establish protection against new variants. Hence, alternative antiviral strategies are needed. Although influenza B and C viruses cause less clinical disease than the A types, new antiviral drugs should also be helpful in curbing infections caused by these agents.

Influenza viruses that occur naturally among birds are called avian influenza (bird flu). The birds carry the viruses in their intestines but do not generally get sick from the infection. However, migratory birds can carry the bird flu to infect domestic chickens, ducks and turkeys causing illness and even death. Avian flu does not easily infect humans but when human exposure is more frequent, such as contact with domestic birds, human infections occur. A dangerous bird flu (H5N1) was first identified in terms in South Africa in 1961 and was identified as a potentially deadly form of flu. Outbreaks of H5N1 occurred in eight Asian countries in late 2003 and 2004. At that time more than 100 million birds in these countries either died or were killed in order to control the outbreak. Beginning in June of 2004 new deadly outbreaks of H5N1 were reported in Asia which are currently ongoing. Human infections of H5N1 have been observed in Thailand, Vietnam and Cambodia with a death rate of about 50 percent.

These infections have mostly occurred from human contact with infected poultry but a few cases of human-to-human spread of H5N1 have occurred.

A triple-reassortant influenza A (H1) virus has been circulating since 1998 with segments from pigs (HA, NP, NA, M and NS), humans (PB1), and birds (PB2 and PA). The newly described and novel swine-origin influenza A (2009H1N1) virus (S-OIV), which is responsible for an ongoing international disease outbreak, is a triple reassortant virus that includes genetic elements of this preexisting virus that have reassorted with the neuraminidase (NA) and matrix (M) segments of a Eurasian swine virus (S-OIV Investigation Team, 2009). The previous influenza A (H1) triple-reassortant virus was occasionally transmitted to humans but not spread efficiently from human-to-human but the new S-OIV is very efficient in human-to-human transmission. Recently, 3440 laboratory confirmed cases of S-OIV infection have been reported from 29 countries. The outbreak began in Mexico, where a total of 1364 cases have been documented, resulting in 45 deaths (case-fatality rate of 3.3%). Outside of Mexico, there have been only three reported deaths (case-fatality rate of 0.1%). The reason for this geographic imbalance in death rate is not clear at this time.

While the S-OIV is currently sensitive to the neuraminidase inhibitors oseltamivir and zanamivir, seasonal influenza has previously been documented to evolve mutations that confer neuraminidase inhibitor resistance. Will S-OIV replace the human H1 as the seasonal influenza virus or will S-OIV reassort with yet another strain of influenza to create another new variant? Will it evolve to become more lethal? These uncertainties are compounded by the time interval from the identification of a new virus to the manufacture and distribution of a new vaccine. Further, a sufficiently novel viral hemagglutinin antigen may necessitate the use of large doses of immunogen and a prime boost schedule, posing practical difficulties for mass vaccination campaigns that must promptly elicit protective immunity. In view of these considerations, there exists an urgent need to create novel forms of prophylaxis and therapy for S-OIV in particular, ideally with broad activity against various influenza viral strains, subtypes and types.

An urgent need exists for new forms of treatment for influenza A based on (a) the known propensity of this virus to undergo both continuous low-level antigenic drift and less frequent but unpredictable major antigenic shift leading to pandemic disease, (b) the clear failure of vaccination, even when strains are reasonably matched, to prevent influenza-related illness in a significant proportion of vaccine recipients, and (c) the increased frequency of resistance to approved forms of therapy for influenza (e.g., the adamantane derivatives and, more recently, the neuraminidase inhibitor, oseltamivir).

In view of the severity of the diseases caused by influenza viruses there is an immediate need for new therapies to treat influenza infection. Given the lack of effective prevention or therapies, it is therefore an object of the present invention to provide therapeutic compounds and methods for treating a host infected with an influenza virus.

BRIEF SUMMARY

Embodiments of the present invention include, in one aspect, an anti-viral compound effective in inhibiting replication within a host cell of an RNA virus having a single-stranded, negative sense genome and selected from the Orthomyxoviridae family including the Influenzavirus A, Influenzavirus B and Influenzavirus C genera. The compound may target viral RNA sequences within a region selected from the following: 1) the 5' or 3' terminal 25 bases of the negative sense viral RNA segments; 2) the terminal 25 bases of the 5' or 3' terminus of the positive sense cRNA; 3) 45 bases surrounding the AUG start codons of influenza viral mRNAs and; 4) 50 bases surrounding the splice donor or acceptor sites of influenza mRNAs subject to alternative splicing.

In certain embodiments, the antiviral compound may include an oligonucleotide characterized by: a) a nuclease-resistant backbone, b) 12-40 nucleotide bases, and c) a targeting sequence of at least 10 bases in length, that hybridizes to a target region selected from the following: i) the 5' or 3' terminal 25 bases of a negative sense viral RNA segment of Influenzavirus A, Influenzavirus B and Influenzavirus C, such as a segment that comprises M1 or M2, ii) the terminal 25 bases of the 5' or 3' terminus of a positive sense cRNA of Influenzavirus A, Influenzavirus B and Influenzavirus C, iii) the 45 bases surrounding the AUG start codon of an influenza viral mRNA, such as an M1 or M2 mRNA, and iv) 50 bases surrounding the splice donor or acceptor sites of Influenzavirus A, Influenzavirus B and Influenzavirus C mRNAs subject to alternative splicing, such as an M1 or M2 mRNA.

An oligonucleotide may also be characterized by: a) the capability of being actively taken up by mammalian host cells, and/or b) the ability to form a heteroduplex structure with the viral target region, wherein said heteroduplex structure is: i) composed of the positive or negative sense strand of the virus and the oligonucleotide compound, and ii) characterized by a Tm of dissociation of at least 45° C.

Embodiments of the present invention include, in another aspect, an antiviral compound that inhibits, in a mammalian host cell, replication of an infecting influenza virus having a single-stranded, segmented, negative-sense genome and selected from the Orthomyxoviridae family. The compound may be administered to the infected host cells as an oligonucleotide characterized by the elements described above. The compound may be administered to a mammalian subject infected with the influenza virus, or at risk of infection with the influenza virus.

The compound may be composed of morpholino subunits linked by uncharged, phosphorus-containing intersubunit linkages, joining a morpholino nitrogen of one subunit to a 5' exocyclic carbon of an adjacent subunit. In one embodiment, the intersubunit linkages are phosphorodiamidate linkages, such as those having the structure:

$$Z=\overset{|}{\underset{|}{P}}-X$$

where $Y_1$=O, Z=O, Pj is a purine or pyrimidine or an equivalent base-pairing moiety effective to bind, by base-specific hydrogen bonding, to a base in a polynucleotide, and X is alkyl, alkoxy, thioalkoxy, or alkyl amino, e.g., wherein X=$NR_2$, where each R is independently hydrogen or methyl.

The compound may be composed of morpholino subunits linked with the uncharged linkages described above interspersed with linkages that are positively charged. The total number of positively charged linkages is between 2 and no more than half of the total number of linkages. The positively charged linkages have the structure above, where X is 1-piperazine.

The compound may include a covalent conjugate of an oligonucleotide analog moiety capable of forming such a heteroduplex structure with the positive or negative sense RNA strand of the virus, and an arginine-rich polypeptide effective to enhance the uptake of the compound into host cells. Exemplary polypeptides comprise one of the sequences identified as SEQ ID NOs:115-128.

In a related aspect, embodiments of the present invention include a heteroduplex complex formed between:
(a) the 5' or 3' terminal 25 bases of the negative sense viral RNA and/or;
(b) the terminal 25 bases of the 5' or 3' terminus of the positive sense mRNA and/or;
(c) 45 bases surrounding the AUG start codon of viral mRNA and/or;
(d) 50 bases surrounding the splice donor or acceptor sites of influenza mRNAs subject to alternative splicing and;
(e) an oligonucleotide characterized by:
(i) a nuclease-resistant backbone,
(ii) capable of uptake by mammalian host cells,
(iii) containing between 12-40 nucleotide bases,
where said heteroduplex complex has a Tm of dissociation of at least 45° C.

In certain embodiments, an exemplary oligonucleotide may be composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

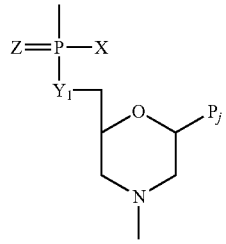

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X=$NR_2$, where each R is independently hydrogen or methyl. The compound may also be composed of morpholino subunits linked with the uncharged linkages described above interspersed with linkages that are positively charged. The total number of positively charged linkages is between 2 and no more than half of the total number of linkages. The positively charged linkages have the structure above, where X is 1-piperazine.

The compound may be the oligonucleotide alone or a conjugate of the oligonucleotide and an arginine-rich polypeptide capable of enhancing the uptake of the compound into host cells. Exemplary polypeptides have one of the sequences identified as SEQ ID NOs:115-128.

In still another aspect, embodiments of the present invention include an antisense oligonucleotide and related methods inhibiting replication in mammalian host cells of an influenza virus having a single-stranded, segmented, negative-sense RNA genome and selected from the Orthomyxoviridae family. The compound may be characterized by the viral RNA elements described herein. In certain embodiments, the cell is in a subject, typically a subject having an influenza-virus infection.

In some embodiments, the subject has a secondary bacterial infection, and the method further comprises administering a bacterial antibiotic, separately or concurrently with the antiviral antisense oligonucleotide. In specific embodiments, the secondary bacterial infection is a Streptococcal pneumonia infection (e.g., *Streptococcus pneuomoniae*). In certain embodiments, the antibiotic is a beta-lactam. In specific embodiments, the antibiotic is selected from penicillin, amoxicillin, cephalosporins, chloramphenicol, and clindamycin.

Also included are methods of reducing replication of an influenza virus, comprising administering an antisense oligonucleotide targeted against an RNA molecule encoding CD200 or the CD200 receptor, separately or concurrently with one or more antiviral antisense oligonucleotides described herein.

A pharmaceutical composition comprising an antiviral antisense oligonucleotide described herein, and a pharmaceutically acceptable carrier. In some embodiments, the pharmaceutical composition further comprises a bacterial antibiotic, such as penicillin, amoxicillin, cephalosporins, chloramphenicol, or clindamycin. In preferred embodiments, the bacterial antibiotic is bacteriostatic. In some embodiments, the pharmaceutical composition further comprises an antisense oligonucleotide targeted against an RNA molecule encoding CD200 or the CD200 receptor.

For treatment of Influenza virus, such as Influenza A virus, the targeting sequence may hybridize to a region associated with one of the group of sequences identified as SEQ ID NOs:1-11. Preferred targeting sequences are those complementary to either the minus strand target of SEQ ID NO:4 or the positive-strand target of SEQ ID NO:2. Exemplary antisense phosphorodiamidate morpholino oligomers ("PMOs") that target these two regions are listed as SEQ ID NOs:23 and 12, respectively.

BRIEF DESCRIPTION OF THE FIGURES

FIG. 4A shows the sequence conservation of the 5' terminal 60 nucleotides of the M1/M2 segment from important serotypes of influenza: H1N1, H1N1(S-OIV), H5N1, H3N2, H9N2 and H7N7.

FIG. 4B shows the percentage of isolates having the indicated base as the subscript number after each base for the M1/M2-AUG target (SEQ ID NO:12)

FIG. 6 shows a dose dependent reduction in viral titer using the M1/M2-AUG targeting compounds of the invention (SEQ ID NOs:12 and 13) in a H3N2 murine model system.

FIGS. 10A-B show the effect of antisense 2' OMe oligomers targeted to the M1/M2 AUG start codon and splice acceptor site on viral HA RNA and M2 protein expression.

DETAILED DESCRIPTION

Definitions

Figure 1A:
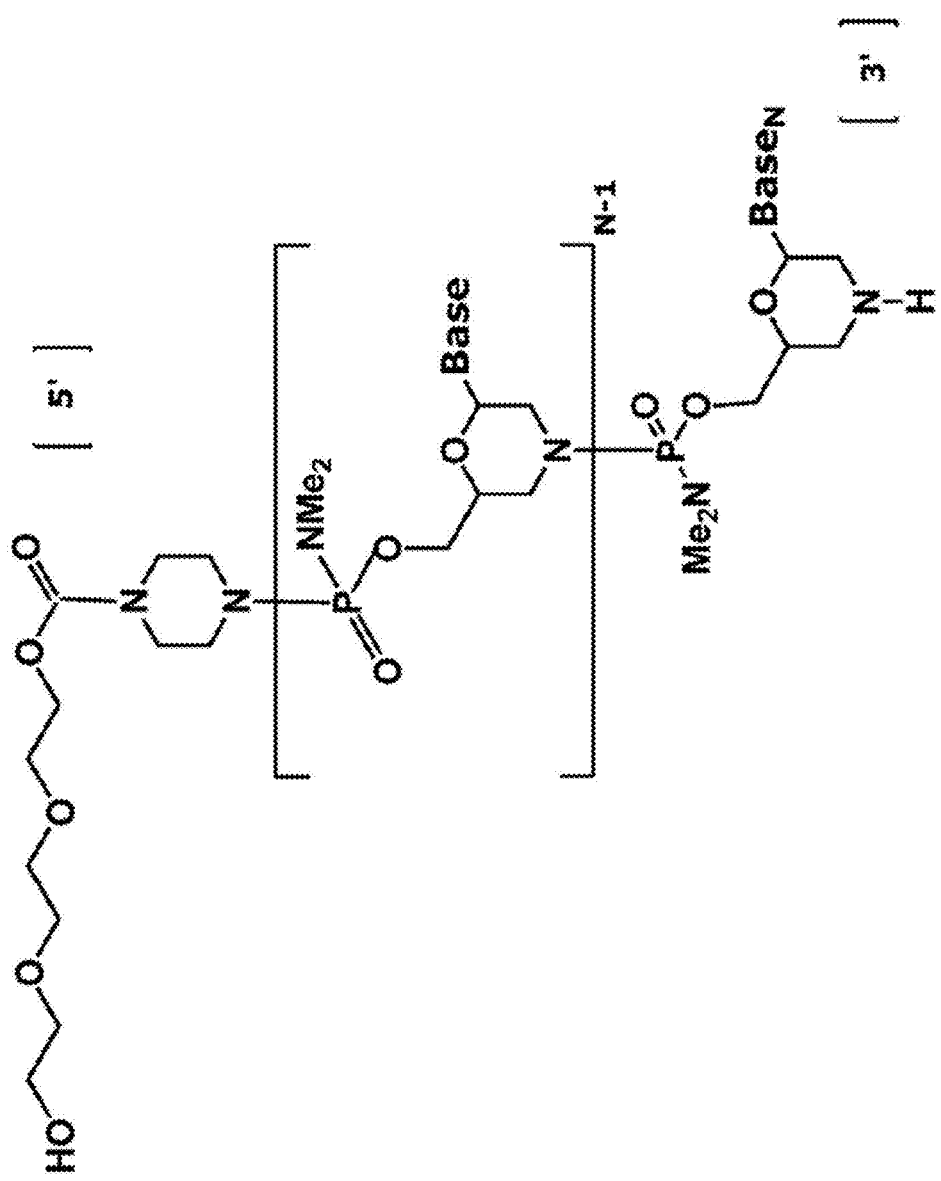
FIG. 1A shows an exemplary morpholino oligomer structure with a phosphorodiamidate linkage.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), 2'-O-Methyl oligonucleotides and RNA interference agents (siRNA agents), and other antisense agents known in the art.

Such an antisense oligomer can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence includes a region including an AUG start codon of an mRNA, a 3' or 5' splice site of a pre-processed mRNA, a branch point. The target sequence may be within an exon or within an intron. The target sequence for a splice site may include an mRNA sequence having its 5' end 1 to about 25 base pairs downstream of a normal splice acceptor junction in a preprocessed mRNA. A preferred splice site target sequence is any region of a pre-processed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

Included are antisense oligonucleotides that comprise, consist essentially of, or consist of one or more of SEQ ID NOS:12-114. Also included are variants of these antisense oligomers, including variant oligomers having 80%, 85%, 90%, 95%, 97%, 98%, or 99% (including all integers in between) sequence identity or sequence homology to any one of SEQ ID NOS: 12-114, and/or variants that differ from these sequences by about 1, 2, 3, 4, 5, 6, 7, 8, 9, or 10 nucleotides, preferably those variants that inhibit influenza replication in a cell. Also included are oligonucleotides of any one or more of SEQ ID NOS: 12-114, which comprise a suitable number of charged linkages, as described herein, e.g., up to about 1 per every 2-5 uncharged linkages, such as about 4-5 per every 10 uncharged linkages, and/or which comprise an Arg-rich peptide attached thereto, as also described herein.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide. See, for example, the structure in FIG. 1A, which shows a preferred phosphorodiamidate linkage type. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. Nos. PCT/US07/11435 (cationic linkages) and PCT Application No. US2008/012804 (improved synthesis), all of which are incorporated herein by reference.

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, typically at least 60% to 100% or 75% or 80% of its linkages, are uncharged or substantially uncharged, and contain a single phosphorous atom. Antisense oligonucleotides and oligonucleotide analogs may contain between about 8 and 40 subunits, typically about 8-25 subunits, and preferably about 12 to 25 subunits. In certain embodiments, oligonucleotides may have exact sequence complementarity to the target sequence or near complementarity, as defined below.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage, as shown in FIG. 1B).

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequence Listing).

An "amino acid subunit" or "amino acid residue" can refer to an α-amino acid residue (—CO—CHR—NH—) or a β- or other amino acid residue (e.g., —CO—(CH$_2$)$_n$CHR—NH—), where R is a side chain (which may include hydrogen) and n is 1 to 7, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (β-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment.

An "effective amount" or "therapeutically effective amount" refers to an amount of therapeutic compound, such as an antisense oligomer or RNA interference agent (e.g., siRNA), administered to a mammalian subject, either as a single dose or as part of a series of doses, which is effective to produce a desired therapeutic effect. For an antisense oligomer, this effect is typically brought about by inhibiting translation or natural splice-processing of a selected target sequence. An "effective amount," targeted against an infecting influenza virus, also relates to an amount effective to reduce the rate of replication of the infecting virus, and/or viral load, and/or symptoms associated with the viral infection.

By "enhance" or "enhancing," or "increase" or "increasing," or "stimulate" or "stimulating," refers generally to the ability of one or antisense or RNAi compounds or compositions to produce or cause a greater physiological response (i.e., downstream effects) in a cell or a subject, as compared to the response caused by either no antisense compound or a control compound. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7. 1.8, etc.) the amount produced by no antisense compound (the absence of an agent) or a control compound.

The term "reduce" or "inhibit" may relate generally to the ability of one or more antisense or RNAi compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of influenza infection, or reductions in viral replication or viral load. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "target sequence" refers to a portion of the target RNA against which the oligonucleotide or antisense agent is directed, that is, the sequence to which the oligonucleotide will hybridize by Watson-Crick base pairing of a complementary sequence. In certain embodiments, the target sequence may be a contiguous region of the viral negative-strand RNA or viral mRNA, or may be composed of regions of the 5' and 3' terminal sequences of the viral genomic or viral complementary RNA.

The term "targeting sequence" or "antisense targeting sequence" refers to the sequence in an oligonucleotide or other antisense agent that is complementary (meaning, in addition, substantially complementary) to the target sequence in the RNA genome. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

The target and targeting sequences may be selected such that binding of the antisense compound is to a region within; 1) the 5' or 3' terminal 25 bases of the negative sense viral RNA; 2) the terminal 30 bases of the 5' or 3' terminus of the positive sense mRNA; 3) 45 bases surrounding the AUG start codons of viral mRNA and/or; 4) 50 bases surrounding the splice donor or acceptor sites of viral mRNAs subject to alternative splicing. In certain embodiments, the target region may include 1) the 5' or 3' terminal 25 bases of the M1 or M2 region of the negative sense viral RNA; 2) the terminal 30 bases of the 5' or 3' terminus of the positive sense M1 or M2 mRNA; 3) 45 bases surrounding the AUG start codons of the M1 or M2 mRNA and/or; 4) 50 bases surrounding the splice donor or acceptor sites of M1 or M2 viral mRNAs. In certain embodiments, the target region may comprise both the AUG codon and the bases surrounding or contributing to the splice donor site of the viral RNA (e.g., M1 or M2 mRNA), such as a polypyrimidine tract or lariat-forming sequence. In certain embodiments, using a single antisense oligomer or RNAi agent to target both the AUG start codon and the proximal splice donor sequences (e.g., polypyrimidine tract) of the M1/M2 RNA may provide synergistic effects with regard to reducing target protein expression, reducing viral replication, or both.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence homology, and preferably at least 95% sequence homology, with the exemplary antisense targeting sequences described herein.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nuci. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an antisense oligonucleotide and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNaseH, which are capable of cutting double-stranded RNA/RNA or RNA/DNA complexes.

A "base-specific intracellular binding event involving a target RNA" refers to the specific binding of an antisense oligonucleotide to a target RNA sequence inside a cell. The base specificity of such binding is sequence dependent. For example, a single-stranded polynucleotide can specifically bind to a single-stranded polynucleotide that is complementary in sequence.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of a disease or pathology in the individual or cell. Treatment includes, but is not limited to, administration of, e.g., a pharmaceutical composition, and may be performed either prophylactically, or subsequent to the initiation of a pathologic event or contact with an etiologic agent. Treatment includes any desirable effect on the symptoms or pathology of a disease or condition associated with influenza virus infection. The related term "improved therapeutic outcome" relative to a patient diagnosed as infected with a particular virus, may refer to a slowing or diminution in the growth of virus, or viral load, or detectable symptoms associated with infection by that particular virus.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

An agent is "actively taken up by mammalian cells" when the agent can enter the cell by a mechanism other than passive diffusion across the cell membrane. The agent may be transported, for example, by "active transport," referring to transport of agents across a mammalian cell membrane by e.g., an ATP-dependent transport mechanism, or by "facilitated transport," referring to transport of antisense agents across the cell membrane by a transport mechanism that requires binding of the agent to a transport protein, which then facilitates passage of the bound agent across the membrane. For both active and facilitated transport, oligonucleotide analogs preferably have a substantially uncharged backbone, as defined below.

Alternatively, the antisense compound may be formulated in a complexed form, such as an agent having an anionic backbone complexed with cationic lipids or liposomes, which can be taken into cells by an endocytic mechanism. The antisense oligonucleotide may also be conjugated, e.g., at its 5' or 3' end, to an arginine-rich peptide, such as a portion of the HIV TAT protein, polyarginine, or to combinations of arginine and other amino acids including the non-natural amino acids 6-aminohexanoic acid (Ahx) and beta-alanine (Ala). Exemplary arginine-rich delivery peptides are listed as SEQ ID NOs:115-128. These exemplary arginine-rich delivery peptides facilitate transport into the target host cell as described (Moulton, Nelson et al. 2004).

Hence, included are methods of treating an influenza virus infection, by administering one or more antisense oligomers of the present invention (e.g., SEQ ID NOS:12-114, and variants thereof), optionally as part of a pharmaceutical formulation or dosage form, to a subject in need thereof. A "subject," as used herein, may include any animal that exhibits a symptom, or is at risk for exhibiting a symptom, which can be treated with an antisense compound of the invention, such as a subject that has or is at risk for having an influenza virus infection. Suitable subjects (patients) include laboratory animals (such as mouse, rat, rabbit, or guinea pig), farm animals, and domestic animals or pets (such as a cat or dog). Non-human primates and, preferably, human patients, are included.

Also contemplated are alternate methods of RNA interference (RNAi), such as those involving double stranded RNA-molecules, or dsRNA. The term "double-stranded" means two separate nucleic acid strands comprising a region in which at least a portion of the strands are sufficiently complementary to hydrogen bond and form a duplex structure. The term "duplex" or "duplex structure" refers to the region of a double stranded molecule wherein the two separate strands are substantially complementary, and thus hybridize to each other.

"dsRNA" refers to a ribonucleic acid molecule having a duplex structure comprising two complementary and anti-parallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides. The term "dsRNA" also includes "siRNA" or short interfering RNA.

It will be understood that the term "ribonucleotide" or "nucleotide" can, in the case of a modified RNA or nucleotide surrogate, also refer to a modified nucleotide, or surrogate replacement moiety at one or more positions. Thus, the dsRNA is or includes a region which is at least partially complementary to the target RNA. In certain embodiments, the dsRNA is fully complementary to the target RNA. It is not necessary that there be perfect complementarity between the dsRNA and the target, but the correspondence must be sufficient to enable the dsRNA, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be substantially complementary with the antisense strand to maintain the overall double-strand character of the molecule.

As used herein, "modified dsRNA" refers to a dsRNA molecule that comprises at least one alteration that renders it more resistant to nucleases (e.g., protein kinase) than an identical dsRNA molecule that recognizes the same target RNA. Modified dsRNAs may include a single-stranded nucleotide overhang and/or at least one substituted nucleotide.

As used herein, a "nucleotide overhang" refers to the unpaired nucleotide or nucleotides that protrude from the duplex structure when a 3'-end of one RNA strand extends beyond the 5'-end of the other complementary strand, or vice versa. "Blunt" or "blunt end" means that there are no unpaired nucleotides at that end of the dsRNA, i.e., no nucleotide overhang. A "blunt ended" dsRNA is a dsRNA that is double stranded over its entire length, i.e., no nucleotide overhang at either end of the molecule.

The term "terminal base pair," as used herein, refers to the last nucleotide base pair on one end of the duplex region of a double-stranded molecule. For example, if a dsRNA or other molecule is blunt ended (i.e., has no nucleotide overhangs), the last nucleotide base pairs at both ends of the molecule are terminal base pairs. Where a dsRNA or other molecule has a nucleotide overhang at one or both ends of the duplex structure, the last nucleotide base pair(s) immediately adjacent the nucleotide overhang(s) is the terminal base pair at that end(s) of the molecule.

Also included are vector delivery systems that are capable of expressing the oligomeric, influenza virus-targeting sequences of the present invention, such as vectors that express a polynucleotide sequence comprising any one or more of SEQ ID NOS:12-114, or variants thereof, as described herein, or that express a polynucleotide sequence that is complementary to any or more of the target sequences of SEQ ID NOS:1-11. Included are vectors that express siRNA or other duplex-forming RNA interference molecules.

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

A vector or nucleic acid construct system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector or nucleic acid construct is preferably one which is operably functional in a mammalian cell, such as a muscle cell. The vector can also include a selection marker such as an antibiotic or drug resistance gene, or a reporter gene (i.e., green fluorescent protein, luciferase), that can be used for selection or identification of suitable transformants or transfectants. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

The term "operably linked" as used herein means placing an oligomer-encoding sequence under the regulatory control of a promoter, which then controls the transcription of the oligomer.

A wild-type gene or gene product is that which is most frequently observed in a population and is thus arbitrarily designed the "normal" or "wild-type" form of the gene.

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl."

"Alkynyl" refers to an unsaturated straight or branched chain hydrocarbon radical containing from 2 to 18 carbons comprising at least one carbon to carbon triple bond. Examples include without limitation ethynyl, propynyl, iso-propynyl, butyryl, iso-butyryl, tert-butynyl, pentynyl and hexynyl. The term "lower alkynyl" refers to an alkynyl group, as defined herein, containing between 2 and 8 carbons.

"Cycloalkyl" refers to a mono- or poly-cyclic alkyl radical. Examples include without limitation cyclobutyl, cyclopentyl, cyclohexyl, cycloheptyl and cyclooctyl.

"Aryl" refers to a substituted or unsubstituted monovalent aromatic radical, generally having a single ring (e.g., phenyl) or two condensed rings (e.g., naphthyl). This term includes heteroaryl groups, which are aromatic ring groups having one or more nitrogen, oxygen, or sulfur atoms in the ring, such as furyl, pyrrolyl, pyridyl, and indolyl. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl. Preferred substituents include halogen, methyl, ethyl, and methoxy. Generally preferred are aryl groups having a single ring.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

"Thioalkoxy" refers to a radical of the formula —SRc where Rc is an alkyl radical as defined herein. The term "lower thioalkoxy" refers to an alkoxy group, as defined herein, containing between 1 and 8 carbons.

"Alkoxy" refers to a radical of the formula —ORda where Rd is an alkyl radical as defined herein. The term "lower alkoxy" refers to an alkoxy group, as defined herein, containing between 1 and 8 carbons. Examples of alkoxy groups include, without limitation, methoxy and ethoxy.

"Alkoxyalkyl" refers to an alkyl group substituted with an alkoxy group.

"Carbonyl" refers to the —C(=O)— radical.

"Guanidynyl" refers to the $H_2N(C=NH_2)$—NH— radical.

"Amidinyl" refers to the $H_2N(C=NH_2)CH$— radical.

"Amino" refers to the —$NH_2$ radical.

"Alkylamino" refers to a radical of the formula —NHRd or —NRdRd where each Rd is, independently, an alkyl radical as defined herein. The term "lower alkylamino" refers to an alkylamino group, as defined herein, containing between 1 and 8 carbons.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Preferably, the ring atoms include 3 to 6 carbon atoms. Such heterocycles include, for example, pyrrolidine, piperidine, piperazine, and morpholine.

Heterocycles include heteroaryls as defined below. Thus, in addition to the heteroaryls listed below, heterocycles also include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

In certain embodiments, the terms "optionally substituted alkyl", "optionally substituted alkenyl", "optionally substituted alkoxy", "optionally substituted thioalkoxy", "optionally substituted alkyl amino", "optionally substituted lower alkyl", "optionally substituted lower alkenyl", "optionally substituted lower alkoxy", "optionally substituted lower thioalkoxy", "optionally substituted lower alkyl amino" and "optionally substituted heterocyclyl" mean that, when substituted, at least one hydrogen atom is replaced with a substituent. In the case of an oxo substituent (=O) two hydrogen atoms are replaced. In this regard, substituents include: deuterium, optionally substituted alkyl, optionally substituted alkenyl, optionally substituted alkynyl, optionally substituted aryl, optionally substituted heterocycle, optionally substituted cycloalkyl, oxo, halogen, —CN, —ORx, NRxRy, NRxC(=O)Ry, NRxSO2Ry, —NRxC(=O)NRxRy, C(=O)Rx, C(=O)ORx, C(=O)NRxRy, —SOmRx and —SOmNRxRy, wherein m is 0, 1 or 2, Rx and Ry are the same or different and independently hydrogen, optionally substituted alkyl, optionally substituted alkenyl, optionally substituted alkynyl, optionally substituted aryl, optionally substituted heterocycle or optionally substituted cycloalkyl and each of said optionally substituted alkyl, optionally substituted alkenyl, optionally substituted alkynyl, optionally substituted aryl, optionally substituted heterocycle and optionally substituted cycloalkyl substituents may be further substituted with one or more of oxo, halogen, —CN, —ORx, NRxRy, NRxC(=O)Ry, NRxSO2Ry, —NRxC(=O) NRxRy, C(=O)Rx, C(=O)ORx, C(=O)NRxRy, —SOmRx and —SOmNRxRy.

The selection of targeting sequences capable of inhibiting replication of the influenza viral genome are discussed below.

Targeted Viruses

Embodiments of the present invention are based, in part, on the discovery that effective inhibition of single-stranded, segmented, negative-sense RNA viruses can be achieved by exposing animals infected with influenza virus to antisense oligonucleotide compounds (i) that target 1) the 5' or 3' terminal 25 bases of the negative sense viral RNA; 2) the terminal 30 bases of the 5' or 3' terminus of the positive sense mRNA; 3) 45 bases surrounding the AUG start codons of viral mRNA and/or; 4) 50 bases surrounding the splice donor or acceptor sites of influenza mRNAs subject to alternative splicing and (ii) having physical and pharmacokinetic features which allow effective interaction between the antisense compound and the virus within host cells. In certain embodiments, the oligomers can be used in treating a mammalian subject infected with influenza virus.

Figure 3:
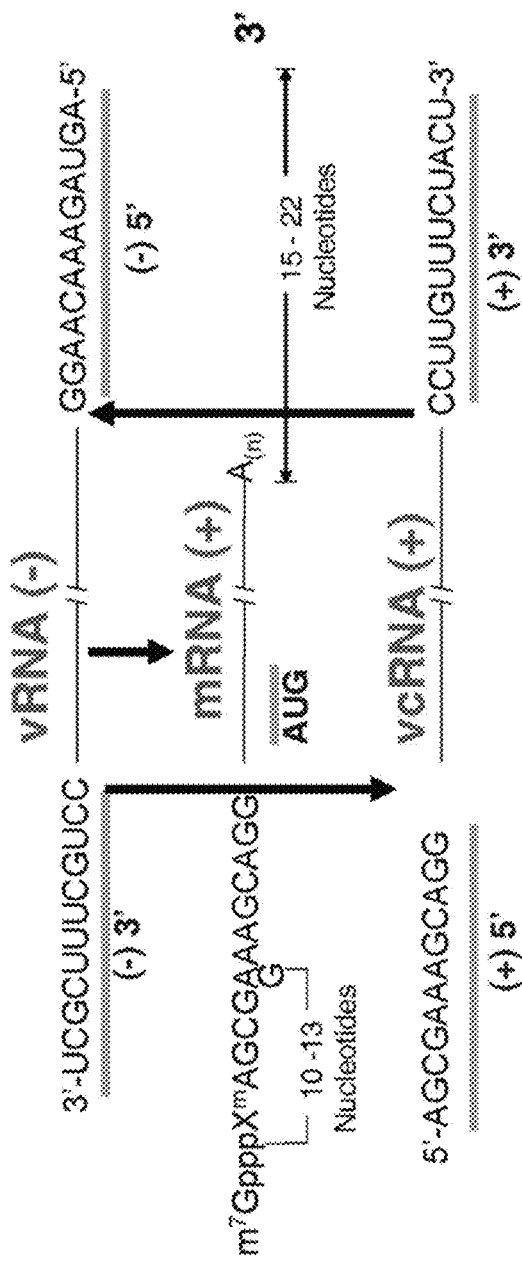
FIG. 3 shows the three different species of influenza virus RNA present in infected cells, vRNA, mRNA and vcRNA, and the target location of targeting PMO described herein.
Figure 5A:
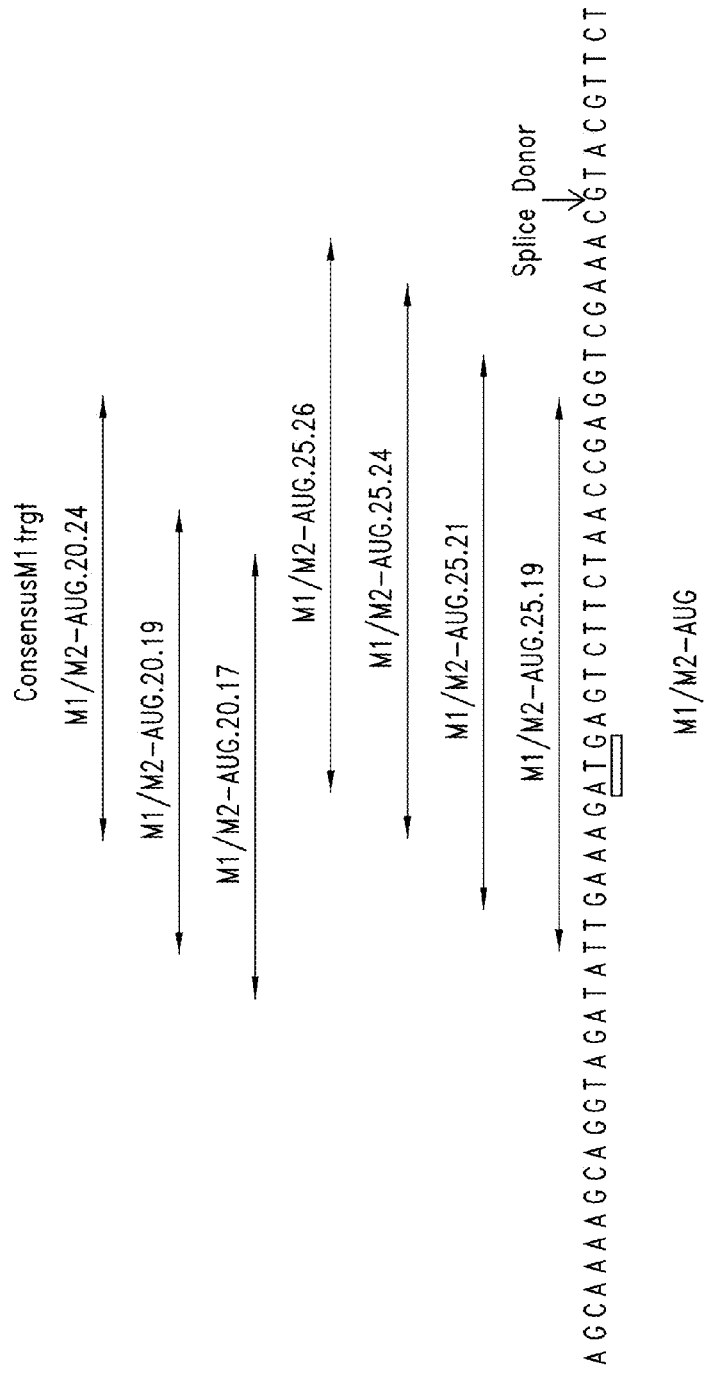
FIGS. 5A-5B show the location of targeting sequences of the invention relative to the AUG start codon and the 5' terminus of the vcRNA, respectively.
Figure 5B:
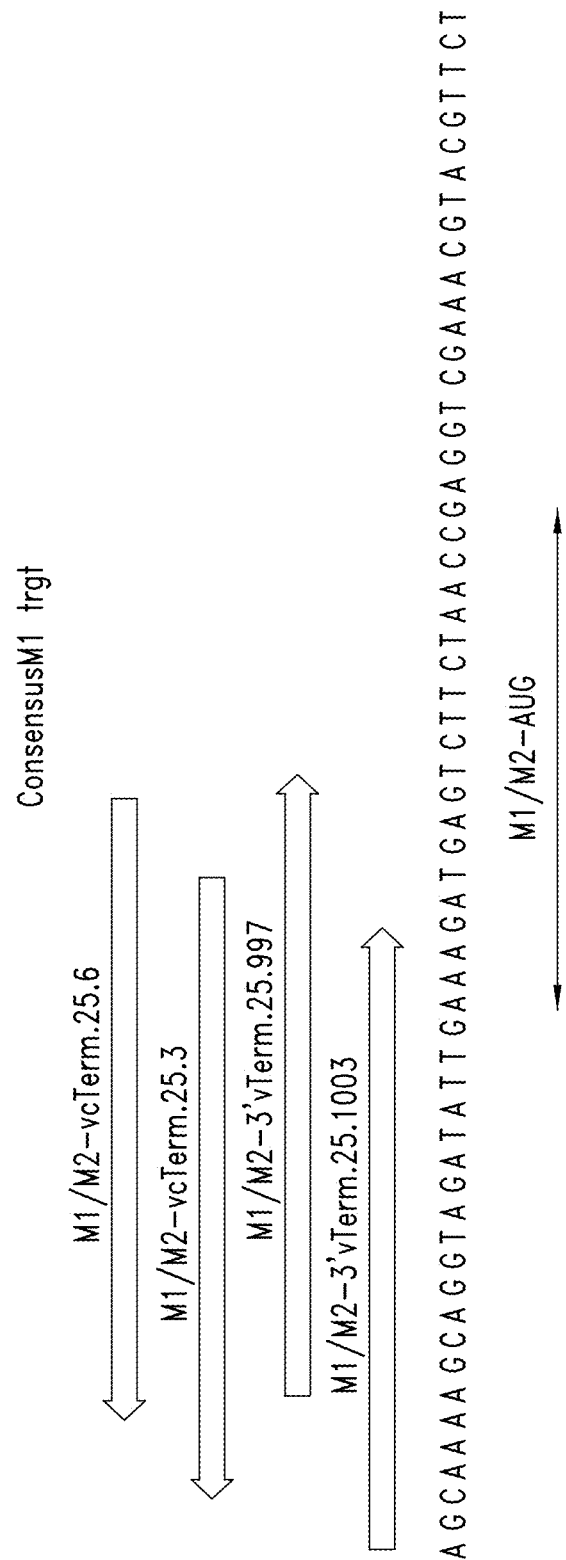

Certain embodiments target RNA viruses having genomes that are: (i) single stranded, (ii) segmented and (iii) negative polarity. The targeted viruses also synthesize two different versions of a genomic complement of the negative sense virion RNA (vRNA) with positive polarity: 1) cRNA that is used as a template for replication of negative sense virion RNA, and 2) a complementary positive sense RNA (mRNA) that is used for translation of viral proteins. FIG. 3 is an exemplary schematic that shows these different RNA species and the target location of antisense PMO described in the present invention.

Targeted viral families include members of the Orthomyxoviridae family including the Influenzavirus A, Influenzavirus B and Influenzavirus C genera. Various physical, morphological, and biological characteristics of members of the Orthomyxoviridae family can be found, for example, in Textbook of Human Virology, R. Belshe, ed., $2^{nd}$ Edition, Mosby, 1991, at the Universal Virus Database of the International Committee on Taxonomy of Viruses (www.ncbi.nlm.nih.gov/ICTVdb/index.htm) and in human virology textbooks (see, for example (Strauss and Strauss 2002)). Some of the key biological characteristics of the Orthomxyoviridae family of viruses are described below.

Influenza A, influenza B and influenza C viruses are the only members of the Influenzavirus A, Influenzavirus B and Influenzavirus C genera, respectively. These viruses are membrane-enclosed viruses whose genomes are segmented negative-sense (i.e. minus) strands of RNA ((−)RNA). The ten influenza virus genes are present on eight segments of the single-stranded RNA of strains A and B, and on seven segments of strain C. The segments vary in size (from 890 to 2341 nucleotides in length) and each is a template for synthesis of different mRNAs. The influenza virus virion contains virus-specific RNA polymerases necessary for mRNA synthesis from these templates and, in the absence of such specific polymerases, the minus strand of influenza virus RNA is not infectious. Initiation of transcription of the mRNAs occurs when the influenza virus mRNA polymerase takes 12 to 15 nucleotides from the 5' end of a cellular mRNA or mRNA precursor and uses the borrowed oligonucleotide as a primer. This process has been termed "cap-snatching" because it places a 5' cap structure on the viral mRNA. Generally, the mRNAs made through this process encode only one protein. The M gene and NS gene viral RNA segments also code for spliced mRNAs, which results in production of two different proteins for each of these two segments.

Replication of influenza viral RNA occurs in the nucleus and involves the synthesis of three different species of RNA. A schematic of this process is shown in FIG. 3. After infection of a naïve cell, the minus strand virion RNA (vRNA) is transported to the nucleus where RNA destined for translation (mRNA) is synthesized using 5'-terminal 10-13 nucleotide primers cleaved by viral-encoded enzymes from capped cellular pre-mRNA molecules (i.e. cap-snatching). Synthesis of each mRNA continues to near the end of the genome segment where an oligo(U) stretch is encountered and a poly(A) tail is added. The dedicated viral mRNAs are transported to the cytoplasm for translation and after sufficient viral proteins are transported back into the nucleus, synthesis of vRNA destined for nascent virions is initiated. An exact antigenomic copy of vRNA is synthesized (termed cRNA) which is a perfect complement of the genomic vRNA and serves as a template for production of new vRNA. The different RNAs synthesized during influenza virus replication are shown schematically in FIG. 3.

GenBank references for exemplary viral nucleic acid target sequences representing influenza A genomic segments are listed in Table 1 below. The nucleotide sequence numbers in Table 1 are derived from the Genbank reference for the positive-strand RNA. It will be appreciated that these sequences are only illustrative of other sequences in the Orthomyxoviridae family, as may be available from available gene-sequence databases of literature or patent resources. The sequences below, identified as SEQ ID NOs:1-11, are also listed in the Sequence Listing at the end of the specification.

Table 1 lists the targets for the influenza A viral genes, M1 and M2 encoded by genomic segment 7. The target sequences in Table 1 represent; 1) the 3' terminal 25 bases of the negative sense viral RNA (SEQ ID NO:4); 2) the terminal 25 bases of the 5' terminus of the positive sense mRNA (SEQ ID NO:3); 3) 45 bases surrounding the AUG start codon of the indicated influenza virus genes (SEQ ID NO:2). The sequences shown are the positive-strand (i.e., antigenomic or mRNA) sequence in the 5' to 3' orientation except for SEQ ID NO: 4 which is the sequence of the minus-strand (i.e., genomic or virion RNA). It will be apparent that when the target is the minus-strand vRNA the targeted sequence is the complement of the sequence listed in Table 1 unless otherwise noted, e.g., SEQ ID NO:4.

The M1 and M2 proteins are components of the viral matrix protein and ion channel activity, respectively. The two proteins are produced from alternative splice forms of the segment 7 vcRNA that utilize the same AUG start site. The M2 protein is the target of two current anti-influenza therapeutics, amantadine and rimantadine. An exemplary target sequence for the AUG start codon region (−20 to +25 relative to the AUG start codon) of the M1/M2 genes is represented as SEQ ID NO: 2 which is a subsequence of the terminal 60 nucleotide region listed as SEQ ID NO:1. The 3' terminal target sequence (25 nucleotides) of the M1/M2 segment is represented by SEQ ID NO:3 which is also a subsequence of the terminal 60 nucleotide region and can be targeted on both the positive strand (vcRNA) and the negative strand (vRNA) of the segment. The 5' terminal sequence (SEQ ID NO:3) can be successfully targeted on the minus strand shown below as SEQ ID NO:4. SEQ ID NOs: 1-4 are from the 2009H1N1virus (S-OIV) and derived from an exemplary isolate of the virus found in the GenBank database under accession number GQ332646. 5' terminal 60 nucleotide regions of other reference influenza A subtypes are listed in Table 1 as SEQ ID NOs: 5, 6, 7, 8 for H1N1, H5N1, H3N2 and $H_2N_2$, respectively. Corresponding AUG and terminal target regions can be derived from these viral sequences using the guidance described above.

It is also possible to target the splice donor and acceptor regions of the M1/M2 segment. The splice donor and splice acceptor sites are at nucleotides 51 and 740, respectively. Targeting of either splice junction using antisense compounds of the invention is contemplated. Furthermore, it is possible to block both the AUG start site and the splice donor site using an appropriately designed antisense compounds (e.g., SEQ ID NOs:12-16 and 19-22). The splice acceptor target region is shown below for the 2009H1N1 (S-OIV) subtype as SEQ ID NO: 10. The corresponding region for the H5N1 subtype is listed in Table 1 as SEQ ID NO: 9.

Furthermore, it is contemplated that any translation-sensitive, splice-sensitive or replication-sensitive region of the M1/M2 segment can be targeted using compounds of the invention. The reference M1/M2 (segment 7) sequence for the prototypic H1N1 subtype (Puerto Rico/8/34) is shown in Table 1 as SEQ ID NO:11 and can be found in the GenBank Reference Sequence database under NC_002016. Corresponding M1/M2 segment sequences can be obtained from publicly available sequence databases. It is contemplated that antisense compounds of the invention can be targeted to other regions of this segment with the expectation that additional translation-, splice- and/or replication-sensitive target regions can be identified.

TABLE 1

Exemplary Influenza Viral Nucleic Acid Target Sequences

| Name | NCBI No. | Nct Region | Sequence (5' to 3') | SEQ ID NO |
|---|---|---|---|---|
| M1/M2-trgt 2009H1N1 | GQ332 646 | 1-60 | AGCAAAAGCAGGUAGAUAUUUAA AGAUGAGUCUUCUAACCGAGGUC GAAAC/GUACGUUCU | 1 |
| M1/M2-AUG | GQ332 646 | 6-50 | AAGCAGGUAGAUAUUUAAAGAUG AGUCUUCUAACCGAGGUCGAAA | 2 |
| M1/M2-vc5'trm | GQ332 646 | 1-25 | AGCAAAAGCAGGUAGAUAUUUAA AG | 3 |
| M1/M2-v3'trm | GQ332 646 | 1072-1097 | CUUUAAAUAUCUACCUGCUUUUG CU | 4 |
| M1/M2-trgt H1N1con | NC_00 2016 | 1-60 | AGCGAAAGCAGGUAGAUAUUGAA AGAUGAGUCUUCUAACCGAGGUC GAAAC/GUACGUUCU | 5 |
| M1/M2-trgt H5N1con | NC_00 7363 | 1-60 | AGCAAAAGCAGGUAGAUAUUGAA AGAUGAGUCUUCUAACCGAGGUC GAAAC/GUACGUUCU | 6 |
| M1/M2-trgt H3N2con | NC_00 7367 | 1-60 | AGCAAAAGCAGGUAGAUAUUGAA AGAUGAGCCUUCUAACCGAGGUC GAAAC/GUAUGUUCU | 7 |
| M1/M2-trgt H2N2con | NC_00 7377 | 1-60 | AGCAAAAGCAGGUAGAUAUUGAA AGAUGAGUCUUCUAACCGAGGUC GAAAC/GUACGUUCU | 8 |
| M1/M2-SA H5N1 | NC_00 7363 | 730-780 | AAAUUUGCAG/GCCUACCAGAAA CGAAUGGGAGUGCAGAUGCAGCG AUUCAA | 9 |
| M1/M2-SA 2009H1N1 | GQ332 646 | 730-780 | AAAUUUGCAG/GCCUACCAGAAG CGAAUGGGAGUGCAGAUGCAGCG AUUCAA | 10 |
| M1/M2 H1N1 segment 7 | NC_00 2016 | 1-1027 | AGCGAAAGCAGGTAGATATTGAA AGATGAGTCTTCTAACCGAGGTC GAAACGTACGTTCTCTCTATCAT CCCGTCAGGCCCCCTCAAAGCCG AGATCGCACAGAGACTTGAAGAT GTCTTTGCAGGGAAGAACACCGA TCTTGAGGTTCTCATGGAATGGC TAAAGACAAGACCAATCCTGTCA CCTCTGACTAAGGGGATTTTAGG ATTTGTGTTCACGCTCACCGTGC CCAGTGAGCGAGGACTGCAGCGT AGACGCTTTGTCCAAAATGCCCT TAATGGGAACGGGGATCCAAATA | 11 |

TABLE 1-continued

Exemplary Influenza Viral Nucleic Acid Target Sequences

| Name | NCBI No. | Nct Region | Sequence (5' to 3') | SEQ ID NO |
|---|---|---|---|---|
| | | | ACATGGACAAAGCAGTTAAACTG TATAGGAAGCTCAAGAGGGAGAT AACATTCCATGGGGCCAAAGAAA TCTCACTCAGTTATTCTGCTGGT GCACTTGCCAGTTGTATGGGCCT CATATACAACAGGATGGGGGCTG TGACCACTGAAGTGGCATTTGGC CTGGTATGTGCAACCTGTGAACA GATTGCTGACTCCCAGCATCGGT CTCATAGGCAAATGGTGACAACA ACCAACCCACTAATCAGACATGA GAACAGAATGGTTTTAGCCAGCA CTACAGCTAAGGCTATGGAGCAA ATGGCTGGATCGAGTGAGCAAGC AGCAGAGGCCATGGAGGTTGCTA GTCAGGCTAGGCAAATGGTGCAA GCGATGAGAACCATTGGGACTCA TCCTAGCTCCAGTGCTGGTCTGA AAAATGATCTTCTTGAAAATTTG CAGGCCTATCAGAAACGAATGGG GGTGCAGATGCAACGGTTCAAGT GATCCTCTCGCTATTGCCGCAAA TATCATTGGGATCTTGCACTTGA TATTGTGGATTCTTGATCGTCTT TTTTTCAAATGCATTTACCGTCG CTTTAAATACGGACTGAAAGGAG GGCCTTCTACGGAAGGAGTGCCA AAGTCTATGAGGGAAGAATATCG AAAGGAACAGCAGAGTGCTGTGG ATGCTGACGATGGTCATTTTGTC AGCATAGAGCTGGAGTAAAAAAC TACCTTGTTTCTACT | |

FIG. 4A shows the conservation of the 5' terminal 60 nucleotides of the M1/M2 segment from important subtypes of influenza A: H1N1, H1N1(S-OIV), H5N1, H3N2, H9N2 and H7N7. FIG. 4B shows conservation of target sequences in one important serotype of influenza, H1N1 (2009), also known as swine-origin influenza A (S-OIV), for each base of a preferred PMO (M1/M2-AUG; SEQ ID NO: 12) based on the NCBI influenza database of genome sequences (Bao Y., P. Bolotov, D. Dernovoy, B. Kiryutin, L. Zaslaysky, T. Tatusova, J. Ostell, and D. Lipman. The Influenza Virus Resource at the National Center for Biotechnology Information. J. Virol. 2008 January; 82(2):596-601). The capital letter indicates the target base and the subscript number next to the base indicates the percent conservation for that base for the H1N1 (2009) isolates in the database as indicated above the sequence. These data indicate no base position shows any significant variation for the M1/M2-AUG target for H1N1 (2009).

In certain embodiments, antisense targeting sequences are designed to hybridize to a region of one or more of the target sequences listed in Table 1. Selected antisense targeting sequences can be made shorter, e.g., about 12 bases, or longer, e.g., about 40 bases, and include a small number of mismatches, as long as the sequence is sufficiently complementary to effect translational, splice and/or replication inhibition upon hybridization with the target, and forms with the viral RNA, a heteroduplex having a Tm of 45° C. or greater.

In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, or 12-25 bases, including all integers in between these ranges. An antisense oligomer of about 14-15 bases is generally long enough to have a unique complementary sequence in the viral genome. In certain embodiments, a minimum length of complementary bases may be required to achieve the requisite binding Tm, as discussed below.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths less than about 30. For PMO oligomers, described further below, an optimum balance of binding stability and uptake generally occurs at lengths of 18-25 bases. Included are antisense oligomers (e.g., PNAs, LNAs, 2'-OMe) and PMO oligomers that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to the target sequences of SEQ ID NOS:1-11, or variants thereof.

In certain embodiments, antisense oligomers may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between an oligomer and a target sequence is a function of the binding Tm and the susceptibility of the duplex to cellular enzymatic cleavage. The Tm of an antisense compound with respect to complementary-sequence RNA may be measured by conventional methods, such as those described by Hames et al., *Nucleic Acid Hybridization*, IRL Press, 1985, pp. 107-108 or as described in Miyada C. G. and Wallace R. B., 1987, Oligonucleotide Hybridization Techniques, *Methods Enzymol.* Vol. 154 pp. 94-107. In certain embodiments, antisense oligomer may have a binding Tm, with respect to a complementary-sequence RNA, of greater than body temperature and preferably greater than about 45° C. or 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

In certain embodiments, such as PMO oligomers, the antisense activity of an oligomer may be enhanced by using a mixture of uncharged and cationic phosphorodiamidate linkages, as exemplified in FIG. 1B. The total number of cationic linkages in the oligomer can vary from 1 to 10 (including all integers in between), and be interspersed throughout the oligomer. Preferably the number of charged linkages is at least 2 and no more than half the total backbone linkages, e.g., between 2, 3, 4, 5, 6, 7, or 8 positively charged linkages, and preferably each charged linkages is separated along the backbone by at least 1, 2, 3, 4, or 5 uncharged linkages. The antisense activity of various oligomers can be measured in vitro by fusing the oligomer target region to the 5' end a reporter gene (e.g., firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays. A preferred antisense oligomer of the invention (M1/M2-AUG) in a form that contains three cationic linkages, as illustrated in FIG. 1B and FIG. 2, interspersed throughout the oligomer is shown as SEQ ID NO: 13 in Table 2 below. A series of exemplary antisense oligomers that target the M1/M2 AUG and contain three interspersed cationic linkages is shown in SEQ ID NOs: 34-47.

Table 2 below shows exemplary targeting sequences, in a 5'-to-3' orientation, that are complementary to influenza A virus. The sequences listed provide a collection of targeting sequences from which targeting sequences may be selected, according to the general class rules discussed above. Although the listed targeting sequences could be used for any antisense analog oligonucleotide chemistry (e.g., PNA, LNA or 2'-OMe) the sequences in Table 2 are preferred for use as PMO antisense oligomers. SEQ ID NOs:12-22, 25-29 and 34-47 are antisense to the positive strand (mRNA or vcRNA) of the virus whereas SEQ ID NOs:23 and 24 are antisense to the minus strand (vRNA). Thus, for example, in selecting a target against the 3' terminus of the minus strand of the M1/M2 encoding segment (segment 7 of influenza A) SEQ ID NO: 4, or a portion of the sequence effective to block the function of the 3' terminus of the minus strand can be selected. SEQ ID NOs: 12-29 and 34-47 target the M1/M2 segment of Influenza A subtype H1N1 (S-OIV) whereas SEQ ID NOs: 30-33 target the PB1 or NP segments as indicated.

TABLE 2

Exemplary Antisense Targeting Sequences

| PMO Name | Target Ncts. | Antisense Oligomer (5' to 3') | SEQ. ID NO. |
|---|---|---|---|
| M1/M2-AUG | 22-41 | CGGTTAGAAGACTCATCTTT | 12 |
| M1/M2-AUGplus | 22-41 | CGGT+TAGAAGAC+TCATC+TTT | 13 |
| M1/M2-AUG.20.17 | 17-36 | AGAAGACTCATCTTTCAATA | 14 |
| M1/M2-AUG.20.19 | 19-38 | TTAGAAGACTCATCTTTCAA | 15 |
| M1/M2-AUG.20.24 | 24-43 | CTCGGTTAGAAGACTCATCT | 16 |
| M1/M2-vcTerm.25.3 | 3-27 | ATCTTTCAATATCTACCTGCTTT | 17 |
| M1/M2-vcTerm.25.6 | 6-30 | CTCATCTTTCAATATCTACCTGCTT | 18 |
| M1/M2-AUG.25.19 | 19-43 | CTCGGTTAGAAGACTCATCTTT | 19 |
| M1/M2-AUG.25.21 | 21-45 | ACCTCGGTTAGAAGACTCATCT | 20 |

TABLE 2-continued

Exemplary Antisense Targeting Sequences

| PMO Name | Target Ncts. | Antisense Oligomer (5' to 3') | SEQ. ID NO. |
|---|---|---|---|
| M1/M2-AUG.25.24 | 24-48 | TCGACCTCGGTTAGAAGACTCA | 21 |
| M1/M2-AUG.25.26 | 26-50 | TTTCGACCTCGGTTAGAAGACT | 22 |
| M1/M2-3'vTerm.25.1003 | 1003-1027 | AGCAAAAGCAGGTAGATATTGA | 23 |
| M1/M2-3'vTerm.25.997 | 997-1021 | AGCAGGTAGATATTGAAAAATC | 24 |
| M1/M2-SA.24.738 | 738-761 | CTCCCATTCGCTTCTGGTAGGC | 25 |
| M1/M2-SA.24.740 | 740-762 | CACTCCCATTCGCTTCTGGTAG | 26 |
| M1/M2-SA.24.742 | 742-764 | TGCACTCCCATTCGCTTCTGGTA | 27 |
| M1/M2-SA.24.744 | 744-766 | TCTGCACTCCCATTCGCTTCTGG | 28 |
| M1/M2-SA.24.746 | 746-768 | CATCTGCACTCCCATTCGCTTCT | 29 |
| NP-v3' |  | AGCAAAAGCAGIGTAGATAATC | 30 |
| NP-v3'plus |  | AGCAAAAGCAGIG+TAGA+TAA+TC | 31 |
| PB1-AUG+15 |  | CGGATTGACATCCATTCAAATG | 32 |
| PB1-AUG+15plus |  | CGGAT+TGACA+TCCAT+TCAA ATG | 33 |
| M1/M2-AUG.20.6+ | 6-25 | CTT+TCAA+TATCTACC+TG CTT | 34 |
| M1/M2-AUG.20.11+ | 11-30 | C+TCA+TCTTTCAA+TATCTACC | 35 |
| M1/M2-AUG.20.12+ | 12-31 | AC+TCA+TCTTTCAA+TATCTAC | 36 |
| M1/M2-AUG.20.13+ | 13-32 | GAC+TCA+TCTTTCAA+TATCTA | 37 |
| M1/M2-AUG.20.14+ | 14-33 | AGAC+TCA+TCTTTCAA+TATCT | 38 |
| M1/M2-AUG.20.15+ | 15-34 | AAGAC+TCA+TCTTTCAA+TATC | 39 |
| M1/M2-AUG.20.16+ | 16-35 | GAAGAC+TCA+TCTTTCAA+TAT | 40 |
| M1/M2-AUG.20.17+ | 17-36 | AGAAGAC+TCA+TCTTTCAA+TA | 41 |
| M1/M2-AUG.20.18+ | 18-37 | TAGAAGAC+TCA+TCTTTCAA+T | 42 |
| M1/M2-AUG.20.19+ | 19-38 | T+TAGAAGAC+TCA+TCTTTCAA | 43 |
| M1/M2-AUG.20.20+ | 20-39 | GT+TAGAAGAC+TCA+TCTTTCA | 44 |
| M1/M2-AUG.20.23+ | 23-42 | TCGGT+TAGAAGAC+TCA+TCTT | 45 |
| M1/M2-AUG.20.25+ | 25-44 | CCTCGGT+TAGAAGAC+TCA+TC | 46 |
| M1/M2-AUG.20.27+ | 27-46 | GACC+TCGGT+TAGAAGAC+TCA | 47 |

Antisense Oligonucleotide Compounds

As detailed above, the antisense oligonucleotide (the term "antisense" indicates that the compound is targeted against either the virus' positive-sense strand RNA or negative-sense or minus-strand) typically comprises a base sequence targeting a region that includes one or more of the following; 1) the 5' or 3' terminal 25 bases of the negative sense viral RNA; 2) the terminal 30 bases of the 5' or 3' terminus of the positive sense vcRNA; 3) 45 bases surrounding the AUG start codons of viral mRNA and/or; 4) 50 bases surrounding the splice donor or acceptor sites of influenza mRNAs subject to alternative splicing. In addition, the oligomer is able to effectively target infecting viruses, when administered to a host cell, e.g., in an infected mammalian subject, such as by reducing target protein expression (e.g., M1 or M2 or both), by reducing viral replication, or both. This requirement is typically met when the oligomer compound (a) has the ability to be actively taken up by mammalian cells, and (b) once taken up, form a duplex with the target RNA with a Tm greater than about 45'C.

In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Exemplary antisense oligomer targeting sequences of the invention using the PMO backbone chemistry are listed above in Table 2. Targeting sequences using alternative chemistries are listed below in Tables 3 and 4 for PNA and LNA chemistries, respectively. In general, PNA and LNA chemistries utilize shorter targeting oligomers due to their relatively high target binding strength compared to PMO and 2'O-Me oligomers.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

PNAs can be produced synthetically using any technique known in the art. A PNA is a DNA analog in which a polyamide backbone replaces the traditional phosphate ribose ring of DNA, as illustrated below.

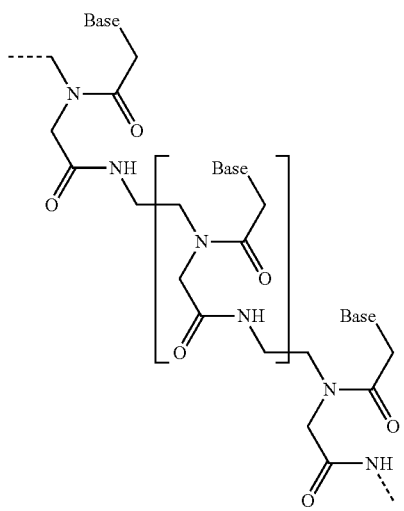

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. Exemplary patents to this technology include U.S. Pat. Nos. 6,969,766, 7,211,668, 7,022,851, 7,125,994, 7,145,006 and 7,179,896. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 254:1497-1500, 1991.

Exemplary PNA compounds for practicing the invention are listed below in Table 3. These oligonucleotides can be prepared essentially according to the procedures set forth in the references cited herein.

TABLE 3

Exemplary PNA Antisense Targeting Sequences

| PNA Name | Target Ncts. | Antisense Oligomer (5' to 3') | SEQ. ID NO. |
| --- | --- | --- | --- |
| PNA-M1-AUG.20.22 | 22-41 | CGGTTAGAAGACTCATCTTT | 48 |
| PNA-M1-AUG.18.24 | 24-41 | CGGTTAGAAGACTCATCT | 49 |
| PNA-M1-AUG.16.26 | 16-41 | CGGTTAGAAGACTCAT | 50 |
| PNA-M1-AUG.20.17 | 17-36 | AGAAGACTCATCTTTCAATA | 51 |
| PNA-M1-AUG.20.19 | 19-38 | TTAGAAGACTCATCTTTCAA | 52 |

TABLE 3-continued

Exemplary PNA Antisense Targeting Sequences

| PNA Name | Target Ncts. | Antisense Oligomer (5' to 3') | SEQ. ID NO. |
| --- | --- | --- | --- |
| PNA-M1-AUG.20.24 | 24-43 | CTCGGTTAGAAGACTCATCT | 53 |
| PNA-M1-vcTerm.20.3 | 3-22 | TCAATATCTACCTGCTTTTG | 54 |
| PNA-M1-vcTerm.20.6 | 6-25 | CTTTCAATATCTACCTGCTT | 55 |
| PNA-M1-3'vTrm.20.1008 | 1003-1027 | AGCAAAAGCAGGTAGATATT | 56 |
| PNA-M1-3'vTrm.20.1002 | 1002-1021 | AGCAGGTAGATATTGAAAAA | 57 |
| M1-SA.20.738 | 738-757 | CATTCGCTTCTGGTAGGCCT | 58 |
| M1/M2-SA.24.740 | 740-759 | CCCATTCGCTTCTGGTAGGC | 59 |
| M1/M2-SA.24.742 | 742-761 | CTCCCATTCGCTTCTGGTAG | 60 |
| M1/M2-SA.24.744 | 744-763 | CACTCCCATTCGCTTCTGGT | 61 |
| M1/M2-SA.24.746 | 746-765 | TGCACTCCCATTCGCTTCTG | 62 |

Oligonucleotide compounds of the present invention may also contain "locked nucleic acid" subunits (LNAs). The structures of LNAs can be found, for example, in Wengel, et al., Chemical Communications (1998) 455; *Tetrahedron* (1998) 54:3607, and Accounts of Chem. Research (1999) 32:301); Obika, et al., *Tetrahedron Letters* (1997) 38:8735; (1998) 39:5401, and *Bioorganic Medicinal Chemistry* (2008) 16:9230. Non-limiting, exemplary LNA structures are illustrated below:

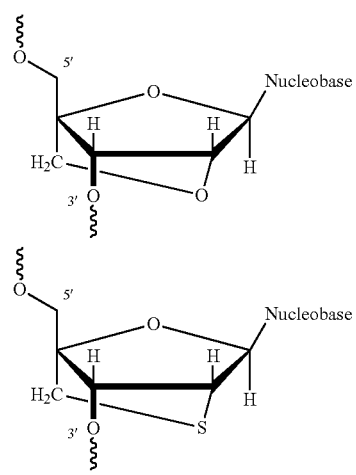

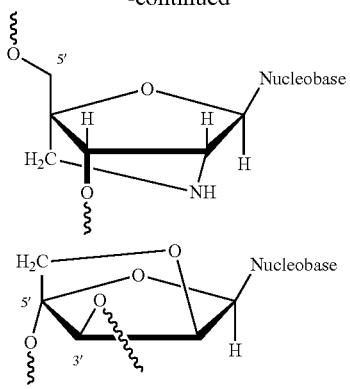

Compounds of the invention may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582, 7,569,575, 7,084,125, 7,060,809, 7,053,207, 7,034,133, 6,794,499, and 6,670,461. Typical intersubunit linkers include phosphodiester and phosphorothioate moieties; alternatively, non-phosphorous containing linkers may be employed. A preferred embodiment is an LNA containing compound where each LNA subunit is separated by a DNA subunit. Further preferred compounds are composed of alternating LNA and DNA subunits where the intersubunit linker is phosphorothioate.

The following compounds are prepared essentially according to the procedures set forth in the references cited above. Exemplary compounds containing LNA subunits (LNAs are capitalized, DNAs are in lower case, and the sequences are read from 5' to 3') are shown below in Table 4.

TABLE 4

Exemplary LNA Antisense Targeting Sequences

| LNA Name | Sequence (5'-3') | SEQ ID NO |
|---|---|---|
| LNA-AUG1 | CgGtTaGaAgAcTcAtCtTt | 63 |
| LNA-AUG2 | GaAgAcTcAt | 64 |
| LNA-AUG3 | GAaGaCtCAT | 65 |
| LNA-AUG4 | GAAGACTCAT | 66 |
| LNA-AUG5 | AGAAGACTCA | 67 |
| LNA-AUG6 | TAGAAGACTC | 68 |
| LNA-AUG7 | TTAGAAGACT | 69 |
| LNA-AUG8 | AAGACTCATC | 70 |
| LNA-AUG9 | AGACTCATCT | 71 |
| LNA-AUG10 | gAcTcAtCtT | 72 |
| LNA-AUG11 | ACTCATCTTT | 73 |
| LNA-AUG12 | CgGtTaGaAgAcTcAt | 74 |
| LNA-AUG13 | GtTaGaAgAcTcAt | 75 |
| LNA-AUG14 | GTTAGAAGACT | 76 |
| LNA-AUG15 | CATCTTTAAAT | 77 |

TABLE 4-continued

Exemplary LNA Antisense Targeting Sequences

| LNA Name | Sequence (5'-3') | SEQ ID NO |
|---|---|---|
| LNA-AUG16 | CaTcTtTaAaTaTcTaC | 78 |
| LNA-AUG17 | CGGTTAGAAGACTCAT | 79 |
| LNA-AUG18 | GGTTAGAAGACTCATC | 80 |
| LNA-AUG19 | GTTAGAAGACTCATCT | 81 |
| LNA-AUG20 | TTAGAAGACTCATCTT | 82 |
| LNA-AUG21 | TAGAAGACTCATCTTT | 83 |
| LNA-AUG22 | AGAAGACTCATCTTTA | 84 |
| LNA-AUG23 | GAAGACTCATCTTTAA | 85 |
| LNA-AUG24 | AAGACTCATCTTTAAA | 86 |
| LNA-AUG25 | AGACTCATCTTTAAAT | 87 |
| LNA-AUG26 | GACTCATCTTTAAATA | 88 |
| LNA-AUG27 | ACTCATCTTTAAATAT | 89 |
| LNA-AUG28 | CTCATCTTTAAATATC | 90 |
| LNA-AUG29 | TCATCTTTAAATATCT | 91 |
| LNA-AUG30 | CATCTTTAAATATCTA | 92 |
| LNA-AUG31 | ATCTTTAAATATCTAC | 93 |
| LNA-AUG32 | TCTTTAAATATCTACC | 94 |
| LNA-AUG33 | CTTTAAATATCTACCA | 95 |
| LNA-AUG34 | TTTAAATATCTACCAG | 96 |
| LNA-AUG35 | CgGgTaGaAgAcTcAt | 97 |
| LNA-AUG36 | GgTtAgAaGaCtCaTc | 98 |
| LNA-AUG37 | GtTaGaAgAcTcAtCt | 99 |
| LNA-AUG38 | TtAgAaGaCtCaTcTt | 100 |
| LNA-AUG39 | TaGaAgAcTcAtCtTt | 101 |
| LNA-AUG40 | AgAaGaCtCaTcTtTa | 102 |
| LNA-AUG41 | GaAgAcTcAtCtTtAa | 103 |
| LNA-AUG42 | AaGaCtCaTcTtTaAa | 104 |
| LNA-AUG43 | AgAcTcAtCtTtAaAt | 105 |
| LNA-AUG44 | GaCtCaTcTtTaAaTa | 106 |
| LNA-AUG45 | AcTcAtCtTtAaAtAt | 107 |
| LNA-AUG46 | CtCaTcTaTaAaTaTc | 108 |
| LNA-AUG47 | TcAtCtTtAaAtAtCt | 109 |
| LNA-AUG48 | CaTcTtTaAaTaTcTa | 110 |
| LNA-AUG49 | AtCtTtAaAtAtCtAc | 111 |
| LNA-AUG50 | TcTtTaAaTaTcTaCc | 112 |
| LNA-AUG51 | CtTtAaAtAtCtAcCa | 113 |
| LNA-AUG52 | TtTaAaTaTcTaCcAg | 114 |

A preferred oligomer structure employs morpholino-based subunits bearing base-pairing moieties, joined by uncharged linkages, as described above. Especially preferred is a substantially uncharged phosphorodiamidate-linked morpholino oligomer. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, and in PCT application No. US2008/012804, all of which are expressly incorporated by reference.

Certain properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNase degradation.

Figure 1B:
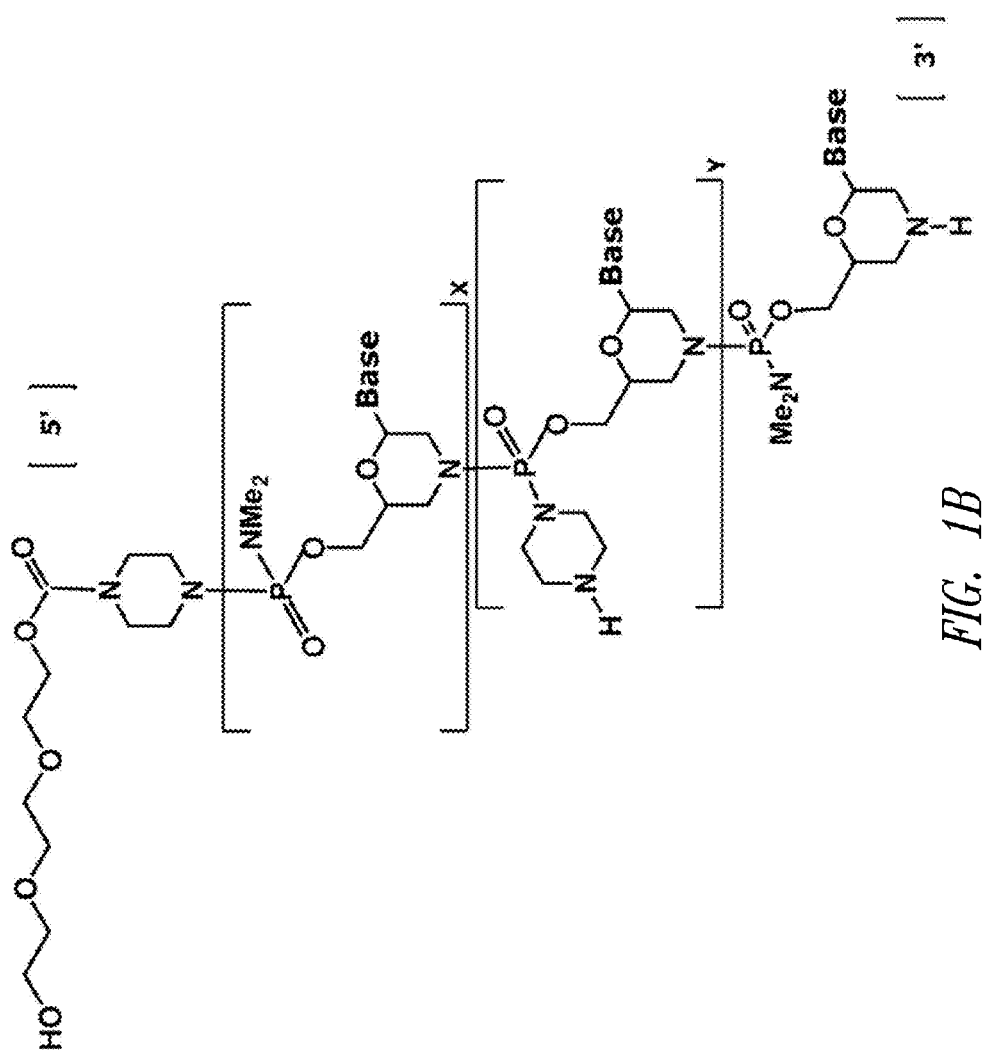
FIG. 1B shows a morpholino oligomer as in FIG. 1A, but where the backbone linkages contain one positively charged group in the form of a (piperazino) phosphorodiamidate linkage.
Figure 1C:
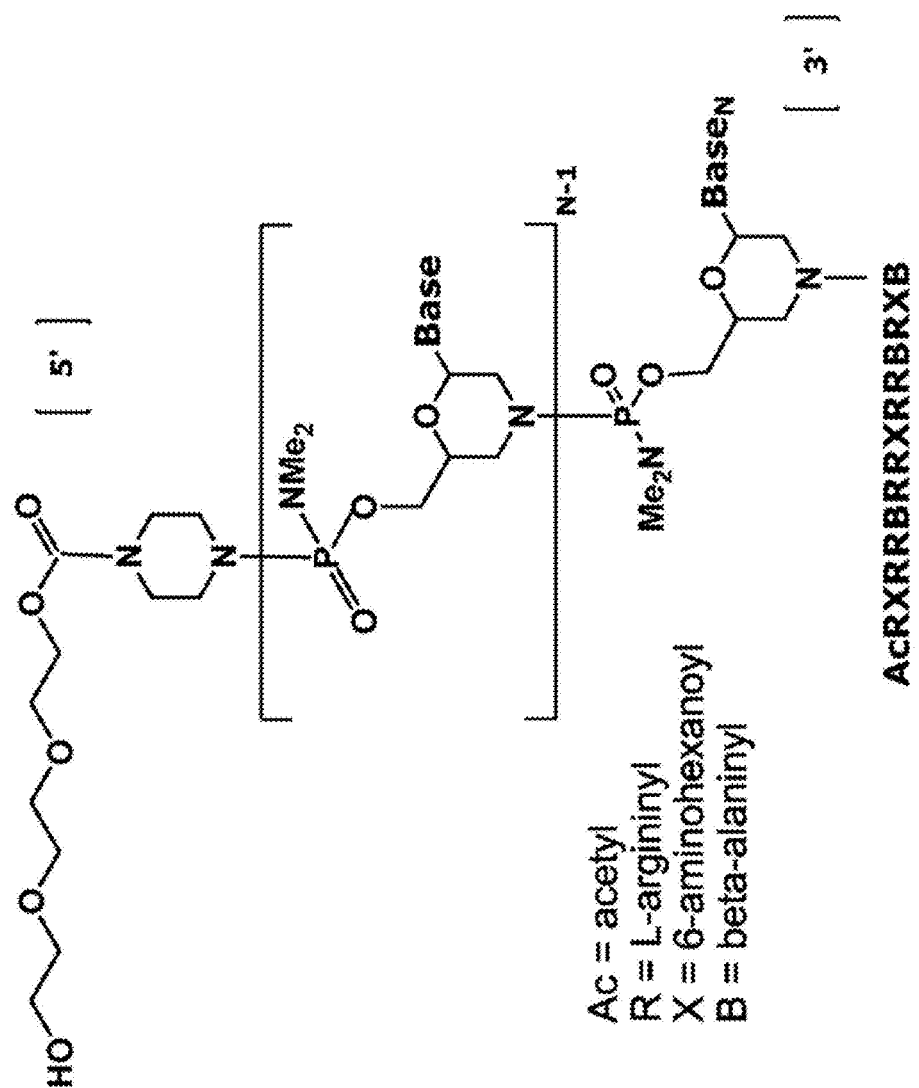
FIG. 1C shows a conjugate of an arginine-rich peptide and an antisense oligomer, in accordance with one embodiment of the invention.
Figure 2:
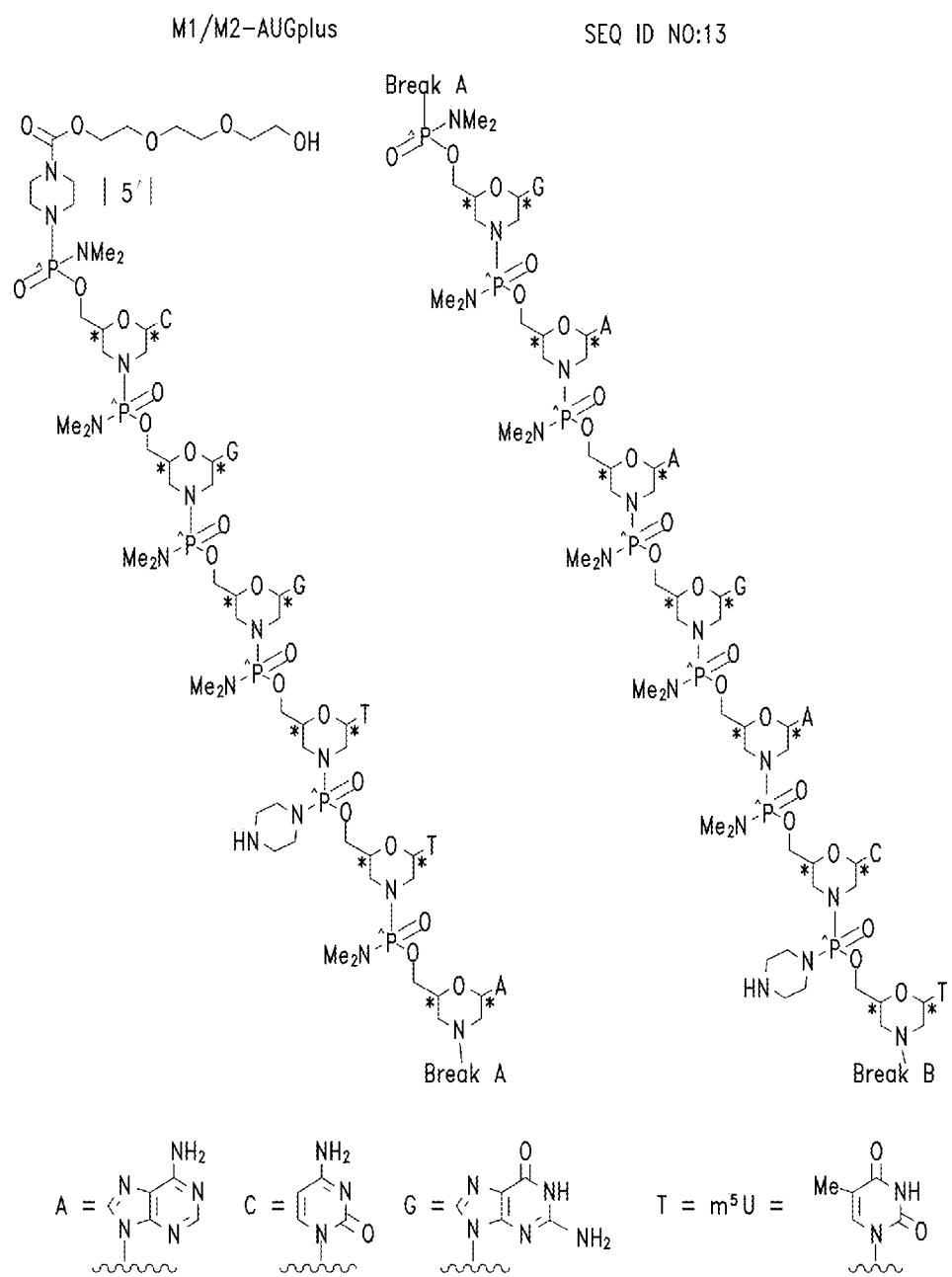
FIG. 2 shows the structure of a preferred exemplary antisense compound of the invention in a PMOplus™ form (M1/M2-AUGplus; SEQ ID NO: 13). The three (piperazino) phosphorodiamidate (pip-PDA) linkages impart a net positive charge, hence the term PMOplus™.
Figure 2:
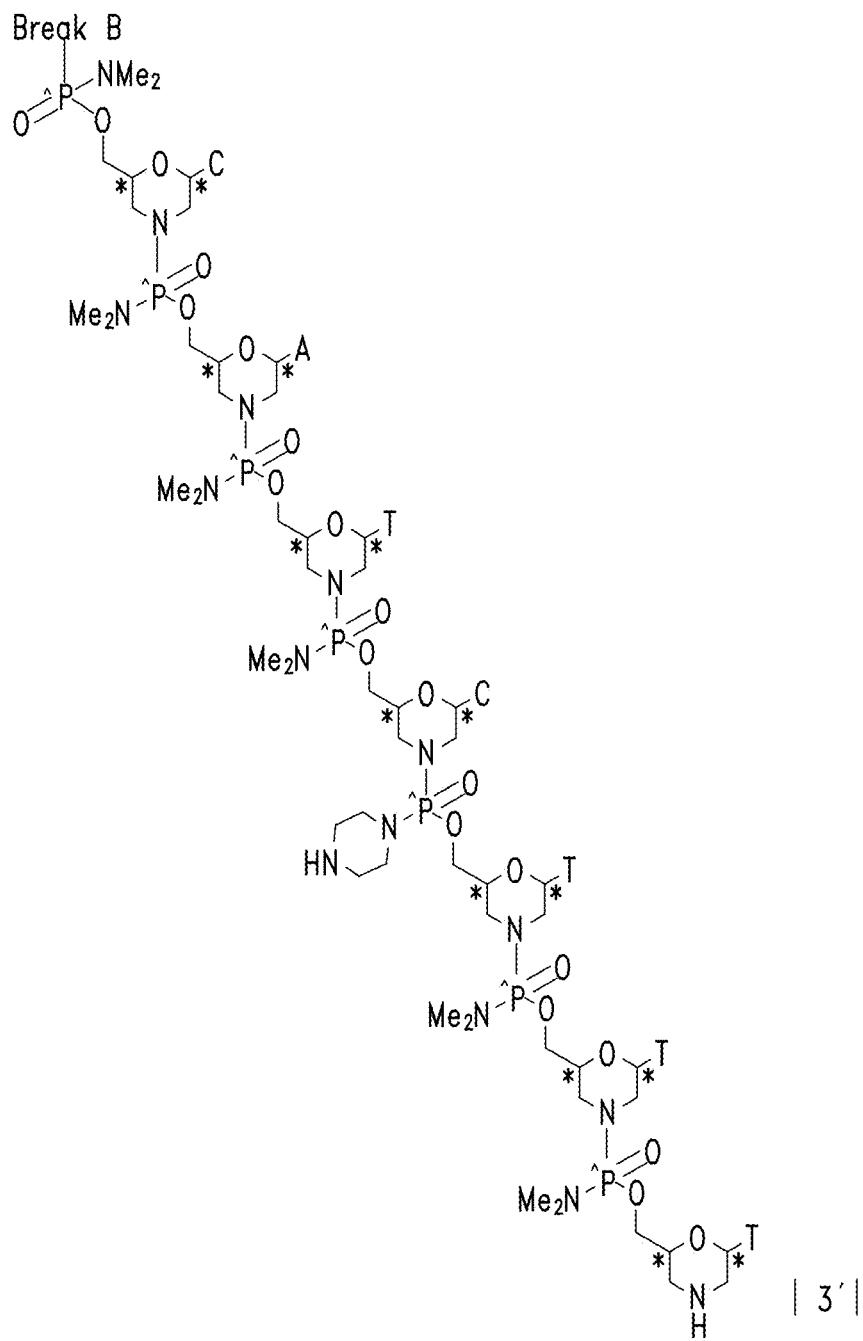

Examples of morpholino oligonucleotides having phosphorus-containing backbone linkages are illustrated in FIGS. 1A-1C. Especially preferred is a phosphorodiamidate-linked morpholino oligonucleotide, as shown in FIG. 1B, which is modified, in accordance with one aspect of the present invention, to contain positively charged groups at preferably 10%-50% of its backbone linkages. Morpholino oligonucleotides with uncharged backbone linkages, including antisense oligonucleotides, are detailed, for example, in (Summerton and Weller, 1997) and in co-owned U.S. Pat. Nos. 5,698,685, 5,217,866, 5,142,047, 5,034,506, 5,166,315, 5,185,444, 5,521,063, and 5,506,337, and in PCT application No. US2008/012804, all of which are incorporated by reference. Exemplary morpholino oligonucleotides with charged backbone linkages and/or modified terminal groups, including antisense oligonucleotides, are detailed in PCT application No. US2007/011435; co-pending U.S. Provisional Application No. 61/349,783; and co-pending U.S. Provisional Application No. 61/361,878, each of which is incorporated by reference in its entirety.

Properties of the morpholino-based subunits include: 1) the ability to be linked in a oligomeric form by stable, uncharged or positively charged backbone linkages; 2) the ability to support a nucleotide base (e.g., adenine, cytosine, guanine, thymidine, uracil and hypoxanthine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNase and RNaseH degradation, respectively.

Figure 1D:
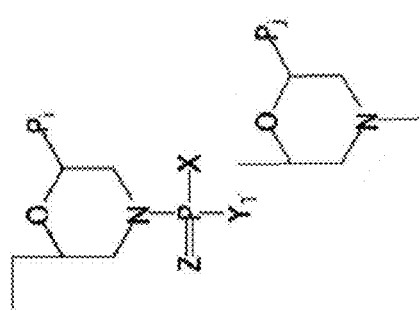
FIGS. 1D-G show the repeating subunit segment of exemplary morpholino oligonucleotides, designated D through G.
Figure 1E:
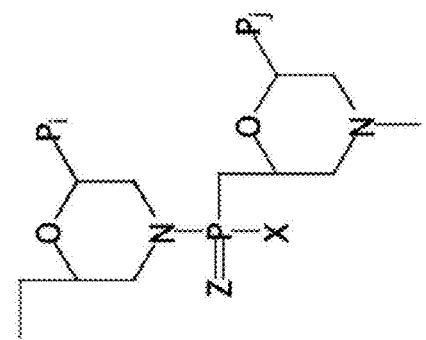

Exemplary backbone structures for antisense oligonucleotides of the claimed subject matter include the morpholino subunit types shown in FIGS. 1D-1G, each linked by an uncharged or positively charged, phosphorus-containing subunit linkage. FIG. 1D shows a phosphorus-containing linkage which forms the five atom repeating-unit backbone, where the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
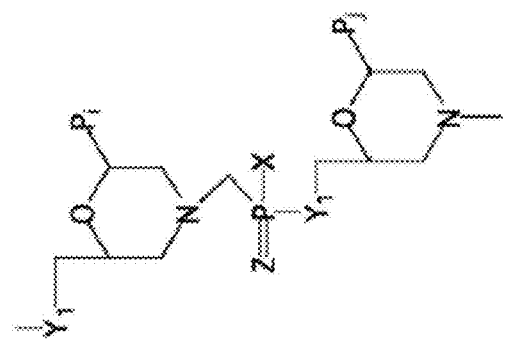
Figure 1G:
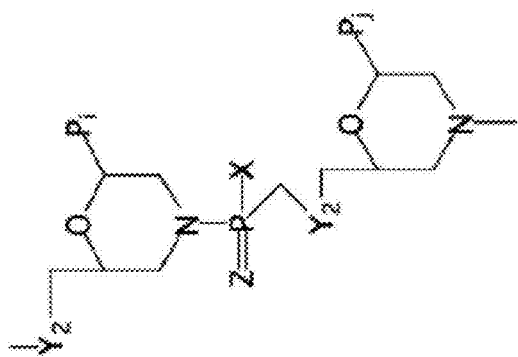

The linkages shown in FIGS. 1F and 1G are designed for 7-atom unit-length backbones. In structure 1F, the X moiety is as in Structure 1E, and the Y moiety may be methylene, sulfur, or, preferably, oxygen. In Structure 1G, the X and Y moieties are as in Structure 1E. Particularly preferred morpholino oligonucleotides include those composed of morpholino subunit structures of the form shown in FIG. 1E, where $X=NH_2$, $N(CH_3)_2$, or 1-piperazine or other charged group, $Y=O$, and $Z=O$.

As noted above, the substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

Additional experiments conducted in support of the present invention indicate that the enhancement seen with added cationic backbone charges may, in some cases, be further enhanced by distributing the bulk of the charges close of the "center-region" backbone linkages of the antisense oligonucleotide, e.g., in a 20-mer oligonucleotide with 8 cationic backbone linkages, having at least 70% of these charged linkages localized in the 10 centermost linkages.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds can be constructed to contain a selected number of cationic linkages interspersed with uncharged linkages of the type described above. The intersubunit linkages, both uncharged and cationic, preferably are phosphorus-containing linkages, having the structure:

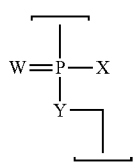

where
W is S or O, and is preferably O,
$X = NR^1R^2$ or $OR^6$,
$Y = O$ or $NR^7$, and each said linkage in the oligomer is selected from:

(a) uncharged linkage (a), where each of $R^1$, $R^2$, $R^6$ and $R^7$ is independently selected from hydrogen and lower alkyl;

(b1) cationic linkage (b1), where $X = NR'R^2$ and $Y = O$, and $NR'R^2$ represents an optionally substituted piperazino group, such that $R'R^2 = —CHRCHRN(R^3)(R^4)CHRCHR—$, where each R is independently H or $CH_3$, $R^4$ is H, $CH_3$, or an electron pair, and $R^3$ is selected from H, lower alkyl, e.g., $CH_3$, $C(=NH)NH_2$, $Z-L-NHC(=NH)NH_2$, and $[C(O)CHR'NH]_mH$, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where $X = NR'R^2$ and $Y = O$, $R' = H$ or $CH_3$, and $R^2 = LNR^3R^4R^5$, where L, $R^3$, and $R^4$ are as defined above, and $R^5$ is H, lower alkyl, or lower (alkoxy) alkyl; and (b3) cationic linkage (b3), where $Y = NR^7$ and $X = OR^6$, and $R^7 = LNR^3R^4R^5$, where L, $R^3$, $R^4$ and $R^5$ are as defined above, and $R^6$ is H or lower alkyl;

and at least one said linkage is selected from cationic linkages (b1), (b2), and (b3).

In certain embodiments, an oligomer may include at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g., $CH_3$, $C(=NH)NH_2$, and $C(O)-L-NHC(=NH)NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g., $—CH_2—CH_2—$), alkoxy ($—C—O—$), and alkylamino (e.g., $—CH_2—NH—$), with the proviso that the terminal atoms in L (e.g., those adjacent to carbonyl or nitrogen) are carbon atoms. Although branched linkages (e.g., $—CH_2—CHCH_3—$) are possible, the linker is preferably unbranched. In one embodiment, the linker is a hydrocarbon linker. Such a linker may have the structure $—(CH_2)_n—$, where n is 1-12, preferably 2-8, and more preferably 2-6.

The morpholino subunits have the structure:

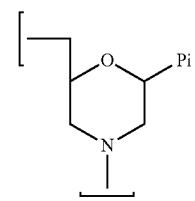

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

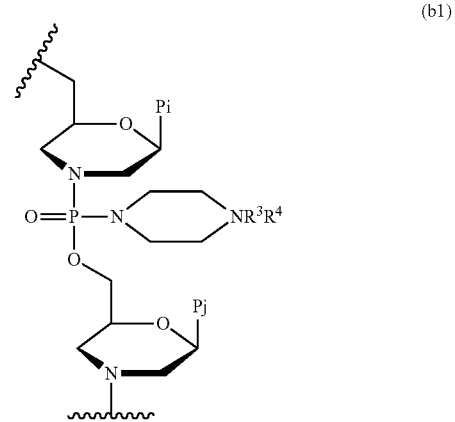

(b1)

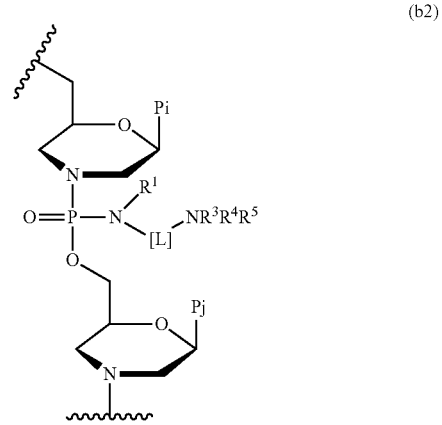

(b2)

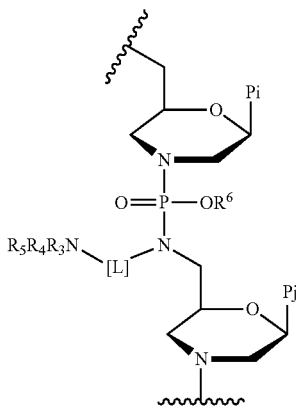
(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1") is referred to herein as a "Pip" linkage and (b1") is referred to herein as a "GuX" linkage:

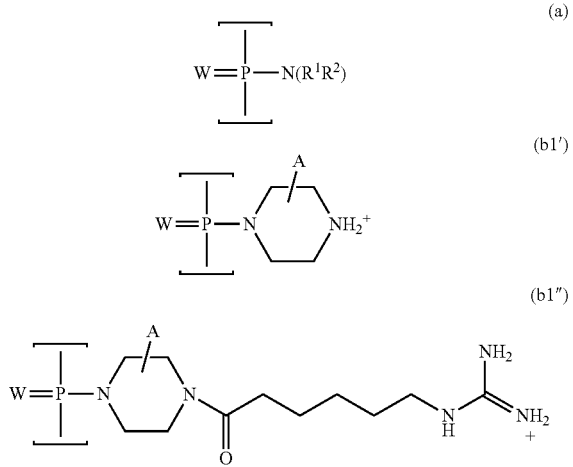

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted. In further embodiments, at least 10% of the linkages are of type (b1') or (b1"); for example, 10%-60% and preferably 20% to 50%, of the linkages may be of type (b1') or (b1").

In certain embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5' nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

Peptide Transporters

In certain embodiments, the antisense compounds of the invention may include an oligonucleotide moiety conjugated to an arginine-rich peptide transport moiety effective to enhance transport of the compound into cells. The transport moiety may be attached to a terminus of the oligomer, as shown, for example, in FIG. 1C. The peptide transport moiety preferably comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid $-C(O)-(CHR)_n-NH-$, where n is 2 to 7 and each R is independently H or methyl; and (c) each Z' subunit independently represents an α-amino acid having a neutral aralkyl side chain;

wherein the peptide comprises a sequence represented by one of $(X'Y'X')_p$, $(X'Y')_m$, $(X')_m$, and $(X'Z'Z')_p$, where p is 2 to 5 and m is 2 to 9. Certain embodiments include various combinations selected independently from (X'Y'X')$_p$, (X'Y')$_m$, (X')$_m$, and/or (X'Z'Z')$_p$, including, for example, peptides having the sequence (X'Y'X')(X'Z'Z')(X'Y'X')(X'Z'Z') (SEQ ID NO:129).

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B. Certain embodiments relate to carrier peptides having a combination of different neutral amino acids, including, for example, peptides comprising the sequence -RAhxRRBRRAhxRRBRAhxB- (SEQ ID NO:124), which contains both β-alanine and 6-aminohexanoic acid.

Preferred peptides of this type include those comprising arginine dimers alternating with single Y' subunits, where Y' is preferably Ahx. Examples include peptides having the formula (RY'R)$_p$ or the formula (RRY')$_p$, where Y' is preferably Ahx. In one embodiment, Y' is a 6-aminohexanoic acid subunit, R is arginine and p is 4.

Certain embodiments include various linear combinations of at least two of (RY'R)$_p$ and (RRY')$_p$, including, for example, illustrative peptides having the sequence (RY'R)(RRY')(RY'R)(RRY') (SEQ ID NO:130), or (RRY')(RY'R)(RRY') (SEQ ID NO:131). Other combinations are contemplated. In a further illustrative embodiment, each Z' is phenylalanine, and m is 3 or 4.

The conjugated peptide is preferably linked to a terminus of the oligomer via a linker Ahx-B, where Ahx is a 6-aminohexanoic acid subunit and B is a β-alanine subunit, as shown, for example, in FIG. 1C. Alternative linkers between the peptide and oligomer include glycine and cysteine. These and related linkers may be conjugated through an amide or disulfide bond.

In selected embodiments, for each X', the side chain moiety is independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In certain embodiments, the Y' subunits may be either contiguous, in that no X' subunits intervene between Y' subunits, or interspersed singly between X' subunits. In certain embodiments, the linking subunit may be between Y' subunits. In one embodiment, the Y' subunits are at a terminus of the transporter; in other embodiments, they are flanked by X' subunits. In further preferred embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx.

In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula (RY'R)$_4$ (SEQ ID NO:132) or the formula (RRY')$_4$ (SEQ ID NO:133), where Y' is preferably Ahx. In the latter case, the nucleic acid analog is preferably linked to a terminal Y' subunit, preferably at the C-terminus, as shown, for example, in FIG. 1C. One exemplary linker is of the structure AhxB, where Ahx is a 6-aminohexanoic acid subunit and B is a β-alanine subunit. Alternative linkers include cysteine and glycine.

The transport moieties as described herein have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11.

The use of arginine-rich peptide transporters (i.e., cell-penetrating peptides) are particularly useful in practicing certain embodiments of the present invention. Certain peptide transporters have been shown to be highly effective at delivery of antisense compounds into primary cells including hematopoietic and muscle cells (Marshall, Oda et al. 2007; Jearawiriyapaisarn, Moulton et al. 2008; Wu, Moulton et al. 2008). Furthermore, compared to other known peptide transporters such as Penetratin and the Tat peptide, the peptide transporters described herein, when conjugated to an antisense PMO, demonstrate an enhanced ability to alter splicing of several gene transcripts (Marshall, Oda et al. 2007). Exemplary peptides in these studies include P007 (SEQ ID NO:118), CP04057 (SEQ ID NO:123), and CP06062 (SEQ ID NO:124).

Exemplary peptide transporters, including linkers (B, AhxB, C, or G) are given below in Table 5. In certain embodiments, the exemplary peptide transporters listed in Table 5 can be conjugated to PMO through disulfide or amide linkages.

TABLE 5

Exemplary Peptide Transporters

| Peptide | Sequence (N-terminal to C-terminal) | SEQ ID NO: |
|---|---|---|
| rTAT | RRRQRRKKRC | 115 |
| R$_9$F$_2$C | RRRRRRRRRFFC | 116 |
| R$_5$F$_2$R$_4$C | RRRRRFFRRRRC | 117 |
| (RAhxR)$_4$AhxB; (P007) | RAhxRRAhxRRAhxR RAhxRAhxB | 118 |
| R$_8$C | RRRRRRRRC | 119 |
| R$_9$C | RRRRRRRRRC | 120 |
| R$_8$G | RRRRRRRRG | 121 |
| R$_9$G | RRRRRRRRRG | 122 |
| (RAhxR)$_5$AhxB (CP04057) | RAhxRRAhxRRAhxR RAhxRRAhxRAhxB | 123 |
| (RAhxRRBR)$_2$AhxB; (CP06062) | RAhxRRBRRAhxRRBRAhxB | 124 |

TABLE 5-continued

Exemplary Peptide Transporters

| Peptide | Sequence (N-terminal to C-terminal) | SEQ ID NO: |
|---|---|---|
| (RAR)$_4$F$_2$C | RARRARRARRARFFC | 125 |
| (RGR)$_4$F$_2$C | RGRRGRRGRRGRFFC | 126 |
| R$_9$F$_2$G | RRRRRRRRRFFG | 127 |
| R$_9$F$_2$XB | RRRRRRRRRFFAhxB | 128 |

RNA Interference Agents

The influenza target regions described herein (e.g., M1, M2; SEQ ID NOS:1-11) may also be targeted by a variety of RNA interference-based methods. RNA interference (RNAi) is an evolutionarily conserved gene-silencing mechanism, originally discovered in studies of the nematode *Caenorhabditis elegans* (Lee et al., Cell 75:843, 1993; Reinhart et al., Nature 403:901, 2000). It may be triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, for example, by Ruvkun, Science 2294:797, 2001).

In certain embodiments, the methods provided herein may utilize double-stranded ribonucleic acid (dsRNA) molecules as modulating agents, for reducing influenza virus replication, such as by interfering with M1 or M2 protein expression. dsRNAs generally comprise two single strands. One strand of the dsRNA comprises a nucleotide sequence that is substantially identical to a portion of the target gene or target region (the "sense" strand), and the other strand (the "complementary" or "antisense" strand) comprises a sequence that is substantially complementary to a portion of the target region. The strands are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, the dsRNA may further comprise at least one chemically modified nucleotide. In certain aspects, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In other aspects, the last complementary nucleotide pairs on both ends of a dsRNA are a G-C pair, or, at least two of the last four terminal nucleotide pairs are G-C pairs.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003). Micro-RNAs are not translated into proteins, but instead bind to specific messenger RNAs, thereby blocking translation. It is thought that micro-RNAs base-pair imprecisely with their targets to inhibit translation. Certain micro-RNAs may be transcribed as hairpin RNA precursors, which are then processed to their mature forms by Dicer enzyme.

In certain embodiments, the modulating agent, or RNAi oligonucleotide, is single stranded. In other embodiments, the modulating agent, or RNAi oligonucleotide, is double stranded. Certain embodiments may also employ short-interfering RNAs (siRNA). In certain embodiments, the first strand of the double-stranded oligonucleotide contains two more nucleoside residues than the second strand. In other embodiments, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In instances when the modulating agent comprises siRNA, the agent should include a region of sufficient homology to the target region, and be of sufficient length in terms of nucleotides, such that the siRNA agent, or a fragment thereof, can mediate down regulation of the target RNA. It will be understood that the term "ribonucleotide" or "nucleotide" can, in the case of a modified RNA or nucleotide surrogate, also refer to a modified nucleotide, or surrogate replacement moiety at one or more positions. Thus, an siRNA agent is or includes a region which is at least partially complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments include one or more but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In addition, an siRNA modulating agent may be modified or include nucleoside surrogates. Single stranded regions of an siRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents may include, for example, molecules that are long enough to trigger the interferon response (which can be cleaved by Dicer (Bernstein et al., Nature, 409:363-366, 2001) and enter a RISC(RNAi-induced silencing complex)), in addition to molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter RNAi agents herein. "siRNA agent or shorter RNAi agent" as used refers to an siRNA agent that is sufficiently short that it does not induce a deleterious interferon response in a human cell, e.g., it has a duplexed region of less than 60 but preferably less than 50, 40, or 30 nucleotide pairs. An siRNA modulating agent, or a cleavage product thereof, can down regulate a target gene, e.g., by inducing RNAi with respect to a target RNA, preferably an influenza target RNA such as M1 or M2.

Each strand of an siRNA modulating agent can be equal to or less than 35, 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA modulating agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_3'$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013, 830, 5,149,797, 5,220,007, 5,256,775, 5,366,878, 5,403,711, 5,491,133, 5,565,350, 5,623,065, 5,652,355, 5,652,356, 5,700,922, and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In one aspect of the invention, modulating agents, such as RNAi agents, relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In other embodiments, the RNAi agent is an oligonucleotide tethered to a ligand for the purposes of improving cellular targeting and uptake. For example, an RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In other embodiments, the modulating agent comprises a non-natural nucleobase. In certain embodiments, the non-natural nucleobase is difluorotolyl, nitroimidazolyl, nitroindolyl, or nitropyrrolyl. In certain embodiments, the modulating agents provided herein relate to a double-stranded oligonucleotide sequence, wherein only one of the two strands contains a non-natural nucleobase. In certain embodiments, the modulating agents as used herein relate to a double-stranded oligonucleotide sequence, wherein both of the strands independently comprise at least one non-natural nucleobase.

In certain instances, the ribose sugar moiety that naturally occurs in nucleosides is replaced with a hexose sugar. In certain aspects, the hexose sugar is an allose, altrose, glucose, mannose, gulose, idose, galactose, talose, or a derivative thereof. In a preferred embodiment, the hexose is a D-hexose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1] octane, or a bicyclo[3.3.1]nonane. In certain embodiments, the backbone of the oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands are complementary, partially complementary, or chimeric oligonucleotides.

Examples of modified RNAi agents envisioned for use in the methods of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. Modified oligonucleotides that do not have a phosphorus atom in their intersugar backbone can also be considered to be oligonucleotides. Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents that teach the preparation of the above phosphorus atom-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,625,050, and 5,697,248, each of which is herein incorporated by reference.

Examples of modified internucleoside linkages or backbones that do not include a phosphorus atom therein (i.e., oligonucleotides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, and 5,677,439, each of which is herein incorporated by reference.

In other examples of oligonucleotide mimetics, both the sugar and the internucleoside linkage, i.e., the backbone, of the nucleoside units may be replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082, 5,714,331, and 5,719,262, each of which is herein incorporated by reference. Further teaching of PNA compounds can be found in Nielsen et al., Science, 1991, 254, 1497.

The present invention further encompasses oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.). The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.* 83:8859-62, 1986; Forster et al., *Cell.* 50:9-16, 1987). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness.

In certain instances, the RNAi agents for use with the methods provided herein may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA*, 86:6553-56, 1989), cholic acid (Manoharan et al., *Bioorg. Med. Chem. Lett.* 4:1053, 1994), a thioether, e.g., hexyl-5-tritylthiol (Manoharan et al., Ann. N.Y. Acad. Sci., 660:306, 1992; Manoharan et al., *Bioorg. Med. Chem. Let.,* 3:2765, 1993), a thiocholesterol (Oberhauser et al., *Nucl. Acids Res.,* 20:533, 1992), an aliphatic chain, e.g., dodecandiol or undecyl residues (Saison-Behmoaras et al., *EMBO J.* 10:111, 1991; Kabanov et al., *FEBS Lett.* 259:327, 1990; Svinarchuk et al., *Biochimie.* 75:49, 1993), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 36:3651, 1995; Shea et al., *Nucl. Acids Res.* 18:3777, 1990), a polyamine or a polyethylene glycol chain (Manoharan et al., *Nucleosides & Nucleotides.* 14:969, 1995), or adamantane acetic acid (Manoharan et al., *Tetrahedron Lett.* 36:3651, 1995), a palmityl moiety (Mishra et al., *Biochim. Biophys. Acta.* 1264:229, 1995), or an octadecylamine or hexylamino-carbonyl-oxycholesterol moiety (Crooke et al., *J. Pharmacol. Exp. Ther.* 277:923, 1996). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Additional examples of modulating agents, such as RNAi oligonucleotides, may be found in U.S. Application Publication Nos. 2007/0275465, 2007/0054279, 2006/0287260, 2006/0035254, 2006/0008822, which are incorporated by reference.

Inhibition of Influenza Viral Replication

The antisense compounds detailed above are useful in inhibiting replication of single-stranded, negative-sense, segmented RNA viruses of the Orthomyxoviridae family. In one embodiment, such inhibition is effective in treating infection of a host animal by these viruses. Accordingly, the method comprises, in one embodiment, contacting a cell infected with the virus with a antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In the present invention as described in the Examples, Phosphorodiamidate Morpholino Oligomers (PMOs), designed to hybridize to the M1/M2 gene segment of influenza A virus (i.e., segment 7), were evaluated for their ability to inhibit influenza virus production in two animal models. The PMOs were either conjugated to a short arginine-rich peptide to facilitate entry into cells or made as PMOplus™ compounds containing cationic linkages. The compounds targeted the AUG translation start-site of the M1 matrix protein (M1) and the ion channel protein (M2) both of which are expressed from the same AUG start codon using alternative splice forms of the M1/M2 mRNA.

The M1/M2-AUG targeted antisense compounds of the invention led to the inhibition of viral titer in a mouse model of H3N2 as described in Example 1. The M1/M2-AUG targeted compounds of the invention also demonstrated reduced clinical signs of flu infection and reduced viral titers in nasal washes in the ferret model of 2009H1N1 (S-OIV) pandemic swine flu as described in Example 2. Accordingly, the antisense oligonucleotides and RNAi agents exemplified herein may be used in the treatment of viral infections, mainly those attributable to single-stranded, negative-sense, segmented RNA viruses of the Orthomyxoviridae family.

Embodiments of the present invention also include combination therapies and related compositions. For instance, the antiviral (i.e., virally-targeted) antisense oligonucleotides and RNAi agents provided herein may be used in combination with host molecule-targeted antisense oligonucleotides or RNAi agents. In this regard, antisense or RNAi targeting of a host immune response gene and/or its receptor can be used to improve the immune response and thereby prevent or reduce subsequent infections, whether viral or bacterial (e.g., secondary bacterial infections). As one example, it has been shown that CD200/R−/− mice do not develop sepsis following influenza infection. CD200 is a negative regulator of innate immune responses resulting in down-regulating the innate immune response in general. Hence, certain methods of treatment may include the administration of antisense and/or RNAi agents targeted against a host RNA molecule encoding CD200 and/or the CD200 receptor (see, e.g., Hatherly et al., *Eur J Immunol.* 34:1688-94, 2004) in combination with the administration (concurrently or separately) of any one or more of the influenza-targeted antisense agents described herein. Also included are compositions that comprise an antisense or RNAi agent targeted against CD200 and/or the CD200 receptor (e.g., targeting its AUG start codon, translation initiation region, or a splice acceptor or splice donor site) in combination with an antisense or RNAi agent targeted against influenza virus, as described herein. These methods and compositions can be used to treat stand-alone influenza virus infections, and/or secondary bacterial infections (e.g., Streptococcal pneumonia) associated with influenza virus infections.

Embodiments of the present invention also include combination therapies for the treatment of viral infections (e.g., influenza infections) accompanied by secondary bacterial infections. The majority of deaths in the 1918-1919 influenza pandemic likely resulted from secondary bacterial pneumonia caused by common upper respiratory-tract bacteria, such as *Streptococcus pneumoniae*, and recent evidence from the H1N1 pandemic of 2009 indicates secondary bacterial infections remain an important cause of death (see, e.g., Louie et al., *Clin Infect Disease.* 50:e59-62, 2010; Jain et al., *N Engl J Med.* 361:1935-44, 2009; Jamieson et al., *Cell Host Microbe.* 7:103-14, 2010). The standard of care for Streptococcal pneumonia includes antibiotics. Primary antibiotics include bactericidal beta-lactam agents such as penicillin and amoxicillin, second line agents include cephalosporins, and third line agents include chloramphenicol or clindamycin. Accordingly, embodiments of the present invention include methods and compositions related to the administration (concurrently or separately) of one or more bacteristatic or bactericidal antibiotics (e.g., penicillin, amoxicillin, cephalosporins, chloramphenicol, clindamycin) in combination with one or more influenza-targeted antisense or RNAi agents provided herein, mainly to treat or manage secondary bacterial infections associated with influenza virus infection.

As another example, the antisense oligonucleotides and RNAi agents of the present invention may be administered (concurrently or separately) in combination with other influenza virus-targeted therapies, such as oseltamivir phosphate (TAMIFLU®). In certain aspects, the combination of one or more antisense oligonucleotides (e.g., AVI-7100) and oseltamivir can achieve synergistic effects in the reduction of influenza viral titer and/or other symptoms of influenza virus infection (e.g., alveolitis, infiltrating immune cells), relative to the use of oseltamivir alone or antiviral antisense oligonucleotides alone. Also included are compositions that comprise oseltamivir in combination with an antiviral antisense oligonucleotide or RNAi agent targeted against influenza virus, as described herein. In specific embodiments, these compositions and methods can be used in the treatment of otherwise oseltamivir-resistant influenza virus infections.

Identification of an Infective Agent

The specific virus causing the infection can be determined by methods known in the art, e.g., serological or cultural methods.

Serological identification employs a viral sample or culture isolated from a biological specimen, e.g., saliva, stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs isolating RNA from a biological specimen followed by nucleic acid amplification using specific PCR primers that target suspected viral agents, e.g., seasonal H1N1 influenza, pandemic H1N1 S-OIV, H5N1 avian influenza or H3N2 swine influenza.

Formulations and Administration

In certain embodiments, the present invention provides formulations or compositions suitable for the therapeutic delivery of antisense oligomers, as described herein. Hence, in certain embodiments, the present invention provides pharmaceutically acceptable compositions that comprise a therapeutically-effective amount of one or more of the oligomers described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, *Trends Cell Bio.*, 2:139; and Delivery Strategies for Antisense Oligonucleotide Therapeutics, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., *Cell Transplant.* 8:47-58, 1999) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999).

The invention also features the use of the composition comprising surface-modified liposomes containing poly (ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science.* 267:1275-1276, 1995; Oku et al., *Biochim. Biophys. Acta.* 1238:86-90, 1995). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 42:24864-24870, 1995; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) as described in U.S. Pat. Nos. 7,163,695, 7,070,807, and 6,692,911 either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

Certain embodiments of the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al., *J. Pharm. Sci.* 66:1-19, 1977).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the oligomers of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An oligomer of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations of the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to reduce influenza virus replication.

Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., *Drug Development and Industrial Pharmacy*, 17:1685-1713, 1991) and REV 5901 (Sheen, P. C., et al., *J Pharm Sci.* 80:712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β. or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol. The complexation takes place by Van der Waals interactions and by hydrogen bond formation. For a general review of the chemistry of cyclodextrins, see, Wenz, Agnew, Chem. Int. Ed. Engl., 33:803-822, 1994.

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I) et al. (U.S. Pat. No. 3,453,259) and Gramera et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention.

Liposomes according to the present invention may be prepared by any of a variety of techniques that are known in the art. See, e.g., U.S. Pat. No. 4,235,871; Published PCT applications WO 96/14057; New RRC, Liposomes: A Practical Approach, IRL Press, Oxford (1990), pages 33-104; Lasic DD, Liposomes from physics to applications, Elsevier Science Publishers BV, Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323. In certain embodiments, reagents such as DharmaFECT® and Lipofectamine® may be utilized to introduce polynucleotides or proteins into cells.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of influenza virus infection (e.g., Oseltamivir, which is marketed under the trade name TAMIFLU®).

In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal, pulmonary and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection (e.g., influenza A) is by inhalation, intranasal or pulmonary delivery. The oligomer may also be delivered directly to the site of viral infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, as noted above, liposomes may be employed to facilitate uptake of the antisense oligonucleotide into cells. (See, e.g., Williams, S. A., *Leukemia.* 10(12):1980-1989, 1996; Lappalainen et al., *Antiviral Res.* 23:119, 1994; Uhlmann et al., Antisense Oligonucleotides: A New Therapeutic Principle, *Chemical Reviews*, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286 or PCT Application No. US1992/005305. Alternatively, the oligonucleotides may be administered in microspheres or microparticles. (See, e.g., Wu, G. Y. and Wu, C. H., *J. Biol. Chem.* 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g., in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

The antisense compounds may be administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 1 mg to 500 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine, etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g., by the method of Spearman-Karber. (See, for example, Pari, G. S. et al., *Antimicrob. Agents and Chemotherapy.* 39(5):1157-1161, 1995; Anderson, K. P. et al., *Antimicrob. Agents and Chemotherapy.* 40:2004-2011, 1996; Cottral, G. E. (ed) in: Manual of Standard Methods for Veterinary Microbiology, pp. 60-93, 1978).

REFERENCES

Abes, R., H. M. Moulton, et al. (2008). "Delivery of steric block morpholino oligomers by (R—X—R)$_4$ peptides: structure-activity studies." *Nucleic Acids Res.*

Cox, N. J. and K. Subbarao (1999). "Influenza." *Lancet* 354 (9186): 1277-82.

Cox, N. J. and K. Subbarao (2000). "Global epidemiology of influenza: past and present." *Annu Rev Med* 51: 407-21.

Egholm, M., O. Buchardt, et al. (1993). "PNA hybridizes to complementary oligonucleotides obeying the Watson-Crick hydrogen-bonding rules." *Nature* 365(6446): 566-8.

Jearawiriyapaisarn, N., H. M. Moulton, et al. (2008). "Sustained Dystrophin Expression Induced by Peptide-conjugated Morpholino Oligomers in the Muscles of mdx Mice." *Mol Ther.*

Marshall, N. B., S. K. Oda, et al. (2007). "Arginine-rich cell-penetrating peptides facilitate delivery of antisense oligomers into murine leukocytes and alter pre-mRNA splicing." *Journal of Immunological Methods* 325(1-2): 114-126.

Moulton, H. M., M. H. Nelson, et al. (2004). "Cellular uptake of antisense morpholino oligomers conjugated to arginine-rich peptides." *Bioconjug Chem* 15(2): 290-9.

Munster, V. J., E. de Wit, et al. (2009). "Pathogenesis and Transmission of Swine-Origin 2009 A(H1N1) Influenza Virus in Ferrets." *Science.*

Stein, C. A., J. B. Hansen, et al. (2010). "Efficient gene silencing by delivery of locked nucleic acid antisense oligonucleotides, unassisted by transfection reagents." *Nucleic Acids Res* 38(1): e3.

Strauss, J. H. and E. G. Strauss (2002). *Viruses and Human Disease*. San Diego, Academic Press.

Summerton, J. and D. Weller (1997). "Morpholino antisense oligomers: design, preparation, and properties." *Antisense Nucleic Acid Drug Dev* 7(3): 187-95.

Wu, B., H. M. Moulton, et al. (2008). "Effective rescue of dystrophin improves cardiac function in dystrophin-deficient mice by a modified morpholino oligomer." *Proc Natl Acad Sci USA* 105(39): 14814-9.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

A. Materials and Methods

All peptides were custom synthesized by Global Peptide Services (Ft. Collins, Colo.) or at AVI BioPharma (Corvallis, Oreg.) and purified to >90% purity (see Example 2 below). PMOs were synthesized at AVI BioPharma in accordance with known methods, as described, for example, in ((Summerton and Weller 1997) and U.S. Pat. No. 5,185,444 and further described in PCT application No. US08/012,804. Exemplary structures of the PMO are as shown in FIGS. 1A-C. 2'-OMe oligomers were synthesized by Integrated DNA Technologies Inc., Skokie, Ill. LNA oligomers were produced by Biosynthesis, Inc., Lewisville, Tex.

Some of the PMO oligomers were conjugated at the 3' end with an arginine-rich peptide ((RAhxRRBR)$_2$AhxB or (RAhxR)$_4$AhxB; SEQ ID NOs: 124 and 118, respectively) to form peptide-conjugated PMOs (PPMOs) to enhance cellular uptake as described (U.S. Pat. No. 7,468,418, PCT application No. US08/008,168 and (Marshall, Oda et al. 2007; Abes, Moulton et al. 2008)).

A synthetic pathway that can be used to make morpholino subunits containing a (1-piperazino) phosphinylideneoxy linkage is described in PCT application No. US07/011,435 and further experimental detail for a representative synthesis is provided below. Reaction of piperazine and trityl chloride gave trityl piperazine, which was isolated as the succinate salt. Reaction with ethyl trifluoroacetate in the presence of a weak base (such as diisopropylethylamine or DIEA) provided 1-trifluoroacetyl-4-trityl piperazine, which was immediately reacted with HCl to provide the salt in good yield. Introduction of the dichlorophosphoryl moiety was performed with phosphorus oxychloride in toluene.

The acid chloride is reacted with morpholino subunits (moN), which may be prepared as described in U.S. Pat. No. 5,185,444 or in Summerton and Weller, 1997 (cited above) and further described in PCT application No. US08/012,804, to provide the activated subunits. Suitable protecting groups are used for the nucleoside bases, where necessary; for example, benzoyl for adenine and cytosine, phenylacetyl for guanine, and pivaloylmethyl for inosine. The subunits containing the (1-piperazino) phosphinylideneoxy linkage can be incorporated into the existing PMO synthesis protocol, as described, for example in Summerton and Weller (1997), without modification.

Example 1

Inhibition of Influenza A Virus in a Murine Model System

A murine model of influenza A virus infection was used to determine the in vivo efficacy of representative antisense oligomers of the infection. Influenza A subtype H2N3 (Port Chalmers/1/73) was used to infect Balb/c female mice via intranasal administration of approximately $4 \times 10^4$ plaque-forming units in a 50 microliter volume. The studies used 12 mice per group with six removed on day two for determination of viral titer and six removed on day six for determination of viral titer. Secondary endpoints included prevention of weight loss and survival.

Three test antisense oligomer compounds, PB1-AUG+15, M1/M2-AUG and NP-v3' (SEQ ID NOs:12, 13 and 30-33) as listed in Table 1 and below in Table 6 were evaluated as both peptide conjugated (PPMO) and positive charge linkage chemistry (PMOplus™). The PPMOs were synthesized using the CP06062 peptide (SEQ ID NO:124) conjugated to the 3' terminus of the PMO. Each test agent was evaluated at three dose levels (10, 30 and 100 micrograms) to establish dose-dependent relationships. Dosing was via the intranasal route beginning 4 hours prior to infection on Day 0 and then daily through Day 4 for a total of 5 doses. The primary endpoint of the study was viral titer reduction in the lung measured as plaque-forming units per gram of lung tissue.

TABLE 6

Antisense Oligomers Used in the H3N2 Murine Model

| Name | Sequence | 3'End | SEQ ID NO |
|---|---|---|---|
| NP-v3' | AGC AAA AGC AGI GTA GAT AAT C | CP06062 | 30 |
| NP-v3'plus | AGC AAA AGC AGI G+TA GA+T AA+T C | H | 31 |
| M1/M2-AUG | CGG TTA GAA GAC TCA TCT TT | CP06062 | 12 |
| M1/M2-AUGplus (AVI-7100) | CGG T+TA GAA GAC +TCA TC+T TT | H | 13 |
| PB1-AUG+15 | CGG ATT GAC ATC CAT TCA AAT G | CP06062 | 32 |
| PB1-AUG+15 plus | CGG AT+T GAC A+TC CAT +TCA AAT G | H | 33 |

FIG. 6 shows the effect on viral titer at Day 6 post-infection. Each viral titer is the average of the six PPMO and six PMOplus™ treated animals. The M1/M2-AUG targeted compounds (SEQ ID NOs: 12 and 13) showed substantially greater activity compared to the other compounds tested. The viral titer from the negative control Dengue treatment shown in FIG. 6 was obtained using an irrelevant PPMO and PMOplus™ sequence that targets the Dengue virus.

Example 2

Inhibition of Influenza A Virus in a Ferret Model System

One observation in support of the present invention was the demonstration of antiviral efficacy of the compounds of the invention in the domestic ferret (*Mustela putorius furo*) animal model system using the novel H1N12009 (S-OIV) virus. Advantages of the ferret model include the ability to use natural human isolate of influenza virus, as opposed to mouse-adapted strains, and the development of most clinical signs observed in humans such as fever and nasal discharge (Munster, de Wit et al. 2009).

Six ferrets were infected with a Tamiflu-resistant H1N1 strain from 2009 obtained from the Centers for Disease Control (pandemic swine flu). The route of viral infection was intranasal ($4 \times 10^4$ plaque-forming units) on Day 1 and dosing was either by intraperitoneal (ip) injection for the PMOplus™ compounds or intranasal (in) for the PPMO compounds. The Dengue-targeted negative control PMOplus™ (30 mg/kg ip dose) and PPMO (1.5 mg/kg in dose) compounds were administered as described above in Example 1. The dosing for PMOplus™ compounds was 10 and 30 mg/kg for the M1/M2-AUGplus (SEQ ID NO: 13; AVI-7100) and 0.5 and 1.5 mg/kg for the M1/M2-AUG PPMO (SEQ ID NO: 12) conjugated on the 3' end to SEQ ID NO:124). Dosing was performed four hours prior to infection and on Days 1, 3 and 5. Tamiflu (Oseltamivir) was administered (10 mg/kg dose) as a positive antiviral control in parallel with the antisense compounds. Saline was also included as a negative control.

Figure 7A:
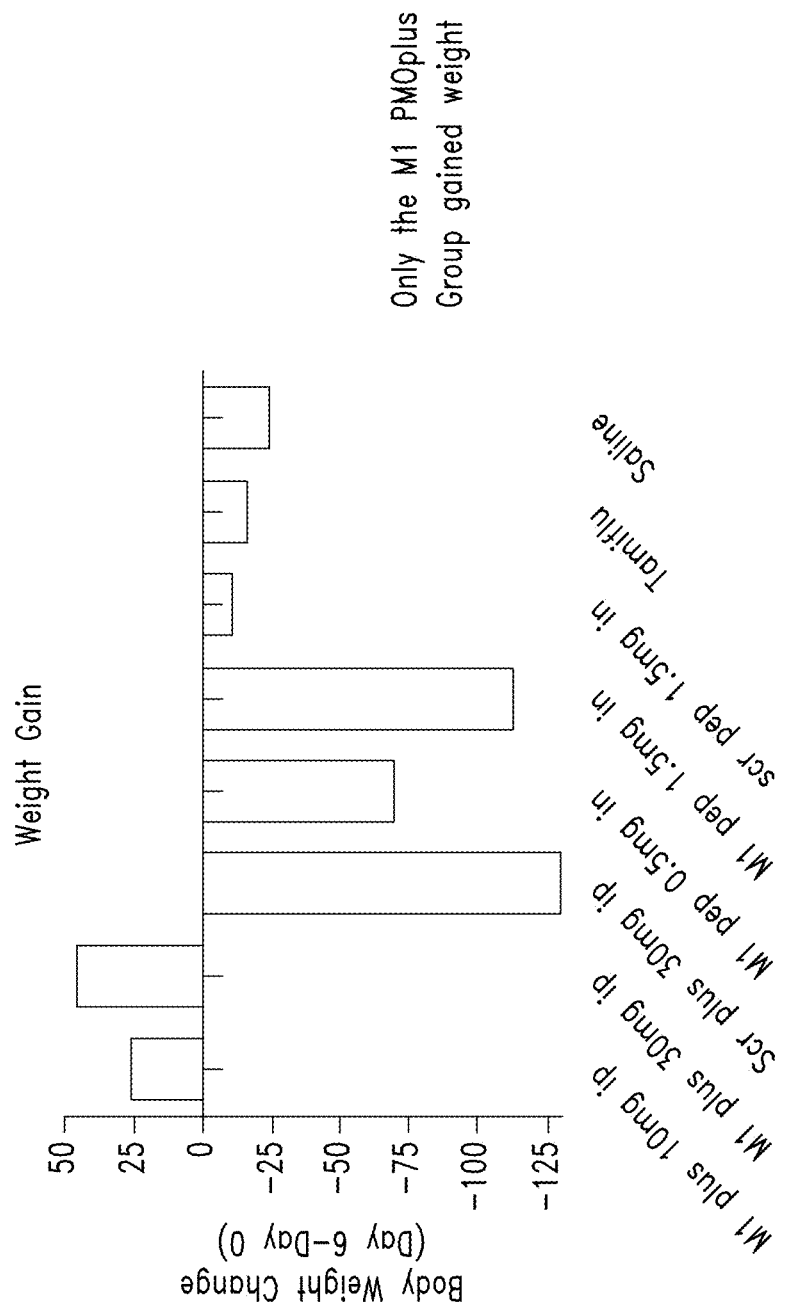
FIGS. 7A-7D show M1/M2-AUG-treated ferrets (SEQ ID NOs: 12 and 13) have reduced in-life clinical signs of flu after infection with a 2009H1N1 (S-OIV) pandemic swine flu isolate.
Figure 7B:
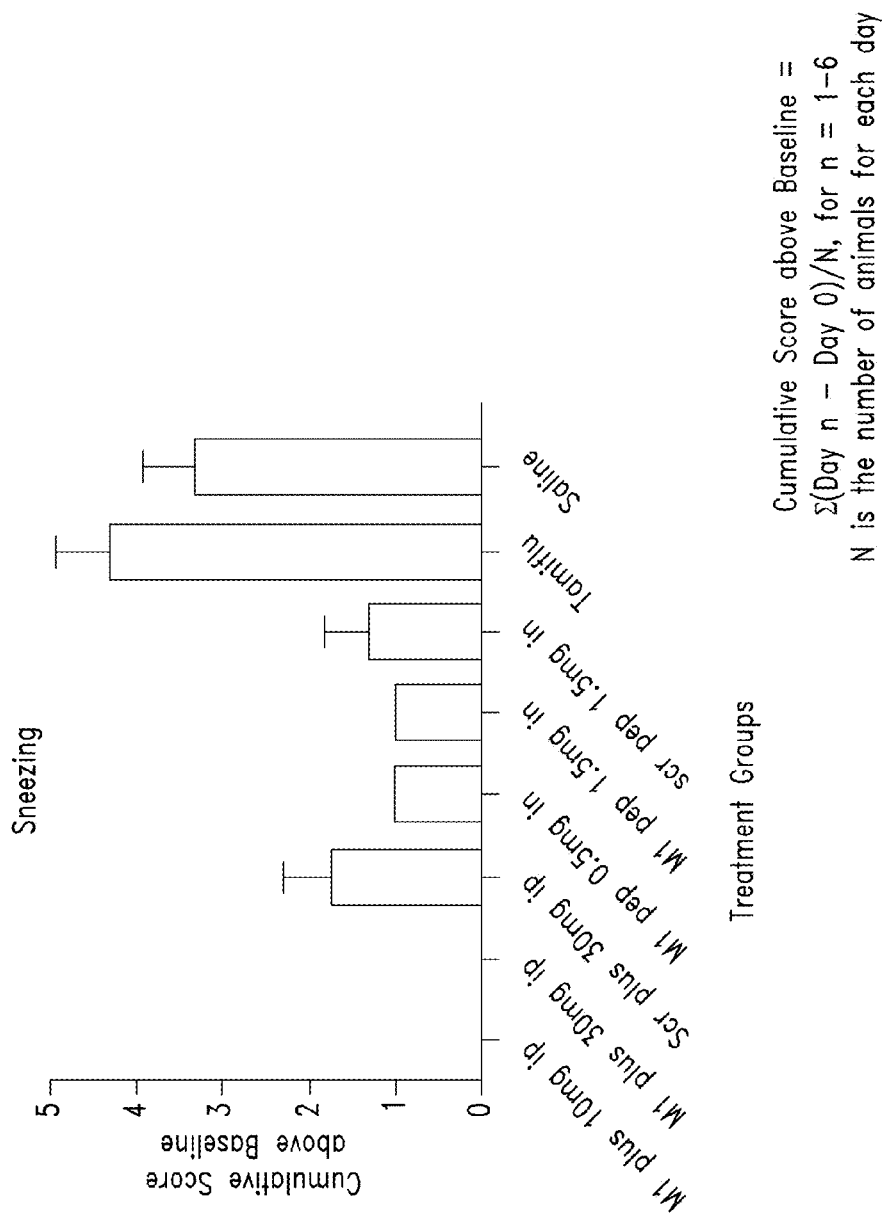
Figure 7C:
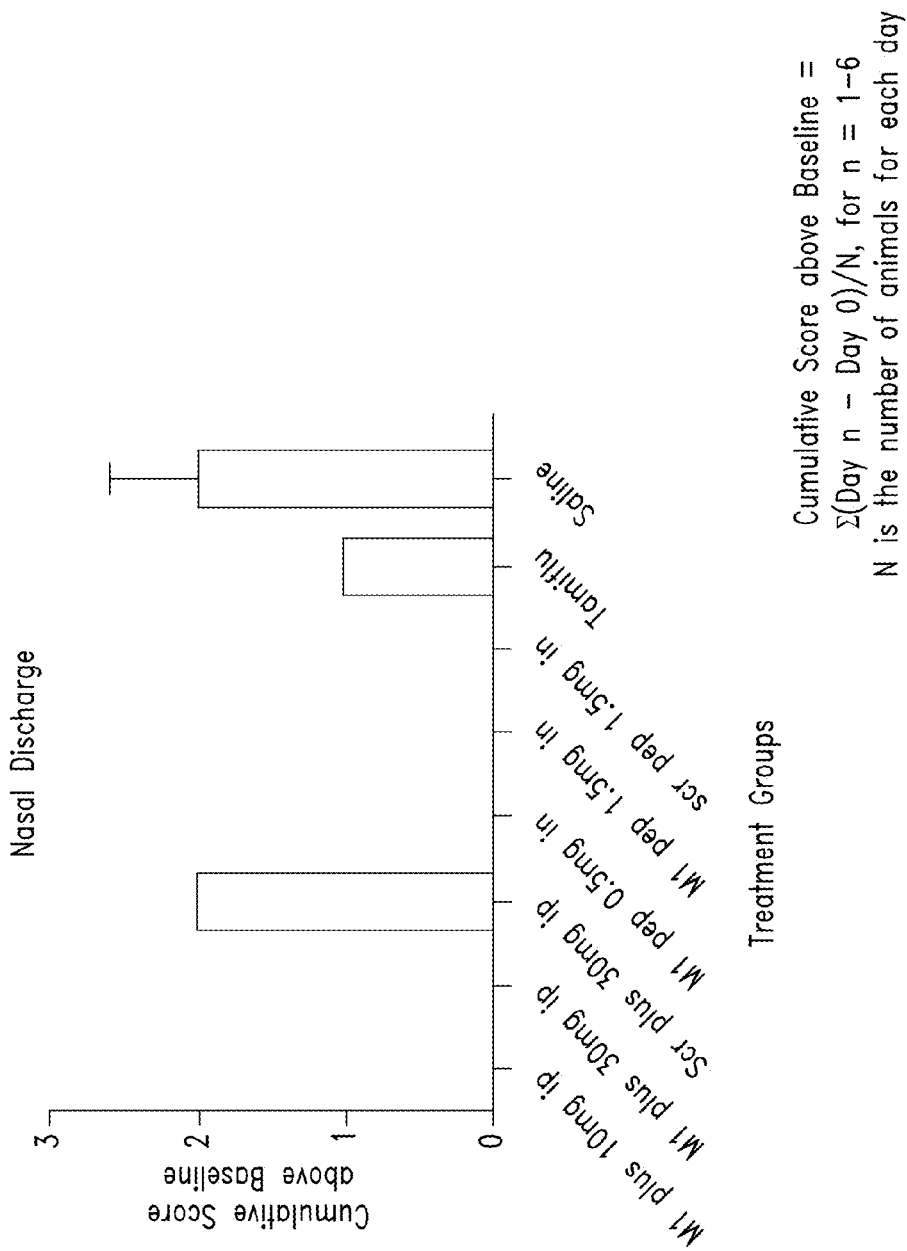
Figure 7D:
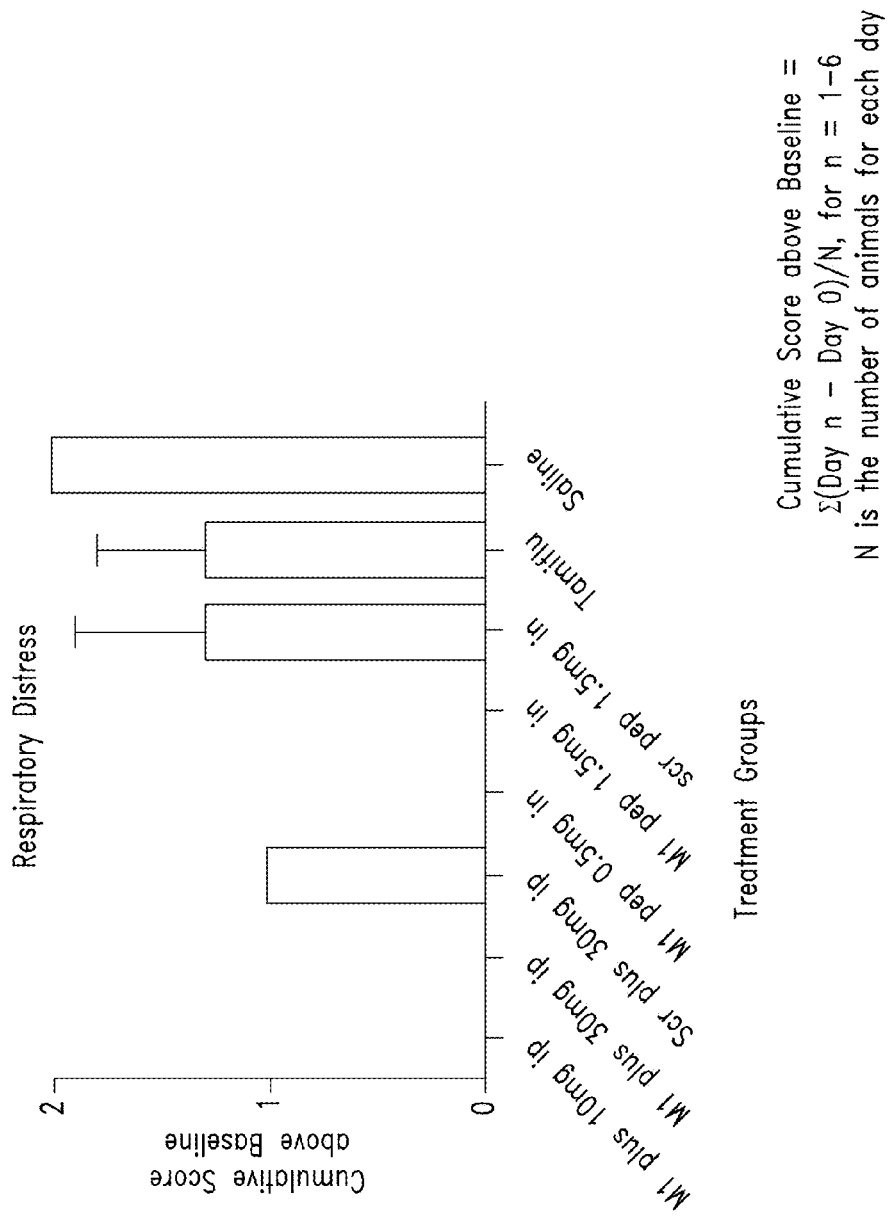
Figure 7E:
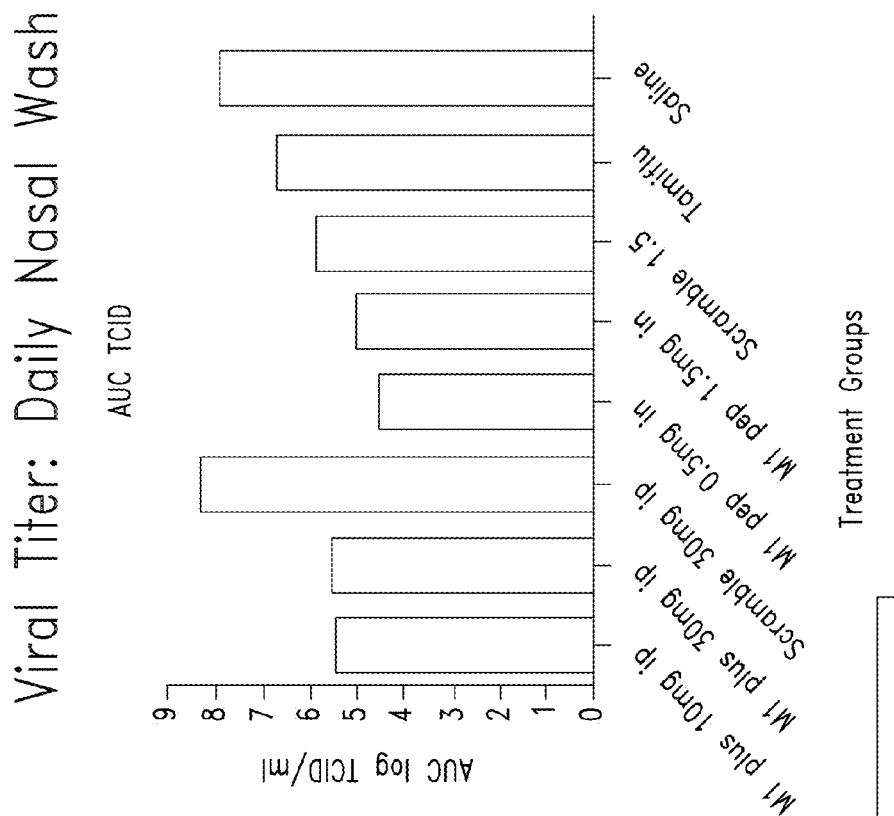
FIG. 7E shows ferrets infected with S-OIV and treated with the M1/M2-AUG compounds of the invention (SEQ ID NOs: 12 and 13) led to a 2.3 log inhibition of viral titer.

In-life observations included weight gain (FIG. 7A), sneezing (FIG. 7B), nasal discharge (FIG. 7C) and respiratory distress (FIG. 7D). The M1/M2-AUG targeted compounds prevented weight loss and reduced sneezing, nasal discharge and respiratory distress. Viral titers from nasal washes for Day 1 through Day 5 post-infection are shown in FIG. 7E as area under the curve (AUC) tissue culture infectious dose (TCID). The M1/M2-AUG PPMO agent showed a 2.3 log reduction relative to saline (99.6% reduction) and a 1.1 log reduction greater than Tamiflu (94.4% greater).

To further evaluate the efficacy of AVI-7100 (SEQ ID NO:13), a PMOplus targeted to the influenza M1/M2 segment translation start site was tested in ferrets infected with a non-adapted oseltamivir-resistant H1N1 (SOIV) pandemic influenza virus. A total of 36 male ferrets were utilized in this study. Male ferrets with matched body weight of about 700 g at study initiation were randomized to one of 5 treatment groups (shown in Table 7 below), and housed in Hepa filtered cages (four per cage) to minimize cage to cage transmission of virus. The cages were maintained within the Tulane University Medical Center BSL-2 laboratory.

TABLE 7

Ferret Study Design

| Group | Agent | Chemistry | Dose (mg/kg) | Route | Schedule | Sacrifice Day 7 |
|---|---|---|---|---|---|---|
| 1 | Tamiflu | — | 5 | p.o. | −4H, 12, 24, 36, 48, 60, 72, 84, 96, 108, 120H | 8 |
| 2 | M1/M2 | PMOplus | 30 | i.p. | −4H, 1, 2, 3, 4, 5D | 8 |
| 3 | M1/M2 | PMOplus | 10 | i.p. | −4H, 1, 2, 3, 4, 5D | 8 |
| 4 | Saline | — | 0.5 | i.n. | −4H, 1, 2, 3, 4, 5D | 6 |
| 5 | M1/M2 and Tamiflu | PMOplus — | 10 5 | i.p. p.o. | −4H, 1, 2, 3, 4, 5D −4H, 12, 24, 36, 48, 60, 72, 84, 96, 108, 120H | 6 |
| | TOTALS | | | | | 36 |

The ferrets were treated with AVI-7100 1 to 4 hours prior to viral challenge. The route of administration was intraperitoneal for groups 2, 3 and 5; and oral for group 1. The dose interval was at −4 hours, 24, 48, 72, 96 and 120 hours post viral challenge. The 5 groups were treated as follows: Group 1 received oseltamivir at 5 mg/kg every 12 hours by the oral route, Group 2 received AVI-7100 (a PMOplus compound; 5'-CGG T+TA GAA GAC+TCA TC+T TT-3') at 10 mg/kg dose by the i.p. route, Group 3 received AVI-7100 (a PMOplus compound) at 30 mg/kg dose by the i.p. route, Group 4 received a sterile saline control by the i.p. route, Group 5 received AVI-7100 at 10 mg/kg once a day by the i.p. route and oseltamivir at 5 mg/kg twice a day. The reason for the differences in group sizes between groups 1-2 (8 ferrets each) and groups 4-5 (6 ferrets each) was due to the limited availability of influenza A seronegative ferrets at the time of the study initiation.

All of the ferrets involved in this study survived to the end of the study, day eight post infection, suggesting either that these animals were very healthy, or that this particular virus was not very pathogenic in this model. Nonetheless, as shown below, these results not only show that treatment with AVI-7100 significantly reduces symptoms of influenza virus infection relative to untreated or oseltamivir-treated controls, but also illustrate the synergistic effects that can be achieved with the combination of AVI-7100 and oseltamivir. A summary of the clinical observations is shown in Table 8 below.

TABLE 8

Clinical Observations

| Group | Clinical Scores | Body Weight Change (g/day) | | | Max Body Temperatures (° F.) | | |
|---|---|---|---|---|---|---|---|
| | | Pre | Post | Difference | Pre | Post | Difference |
| Tamiflu | 1.17 ± 0.25 | 15.1 ± 0.4 | 8.5 ± 3.2 | −6.1 | 104.4 | 105.7 | +1.3 |
| M1-30 | 1.00 ± 0.00 | 11.8 ± 0.8 | 12.6 ± 2.0 | +0.8 | 104.7 | 104.2 | −0.5 |
| M1-10 | 1.11 ± 0.21 | 16.6 ± 0.8 | 10.9 ± 1.5 | −5.7 | 105.4 | 106.1 | +0.7 |
| Saline | 1.19 ± 0.25 | 14.3 ± 0.6 | 11.4 ± 2.1 | −2.9 | 105.9 | 106.2 | +0.3 |
| M1 + Tamiflu | 1.06 ± 0.06 | 14.4 ± 0.6 | 14.9 ± 1.0 | +0.5 | 105.0 | 104.9 | −0.1 |

As a further indicator, observations of cells that infiltrate into the upper respiratory tract are a measure of the severity of the infection. The summary of macrophage cellularity in nasal wash is included in Table 9 below. In addition, untreated and oseltamivir-only treated ferrets showed significant congestion in the lung with marked alveolitis (inflammation of the lung), abundant infiltrating cells including lymphocytes and neutrophils, and moderate alveolar wall thickening of the lung. In contrast, AVI-7100 treated ferrets (with or without oseltamivir) showed no congestion in the lung, only mild alveolitis, and few infiltrating cells.

TABLE 9

Macrophage Cellularity in Upper Respiratory Tract

| Group | Average ± Std Deviation | Day 3 Peak |
|---|---|---|
| Tamiflu | 2.98 ± 2.71 | 7.91 ± 7.28 |
| M1-30 | 2.78 ± 2.97 | 1.59 ± 1.28 |
| M1-10 | 4.34 ± 3.82 | 3.88 ± 4.73 |
| Saline | 5.02 ± 3.77 | 2.41 ± 3.24 |
| M1 + Tamiflu | 4.27 ± 3.10 | 0.91 ± 1.25 |

As shown in Table 10 below, peak viremia in nasal wash was observed on day 1. No nasal wash was collected on day 2, 4, 6 and 7 in order to minimize the untoward influence of collecting the nasal wash on the progression of the viral infection. Significant benefit was observed in the AVI-7100 treated group relative to either saline or oseltamivir. Synergistic effects were also observed with the combination of AVI-7100 (10 mg/kg) and oseltamivir, relative to AVI-7100-only (10 mg/kg) and oseltamivir-only treatments. Here, the AUC for viral titer in nasal wash for the combination (AVI-7100 and oseltamivir) shows a greater than 4 log reduction relative to the tamiflu-only group and a greater than 3 log reduction relative to the saline group. The combination also shows a much greater reduction in viral titer relative to the equivalent amount of AVI-7100 alone (from AUC of 5.515 to AUC of 2.999), suggesting that AVI-7100 may enhance the anti-viral effects of oseltamivir. This result is surprising because the virus used in this study is otherwise resistant to oseltamivir.

TABLE 10

Viral Titer

| Day | Oseltamivir (n = 8) | AVI-7100 30 mg/kg (n = 8) | AVI-7100 10 mg/kg (n = 8) | Saline (n = 6) | Oseltamivir + AVI-7100 10 mg/kg (n = 6) |
|---|---|---|---|---|---|
| 1 | 2.42 ± 0.58 | 0.57 ± 0.49 | 1.10 ± 1.11 | 2.42 ± 0.49 | 0.82 ± 0.79 |
| 3 | 0.77 ± 0.73 | 0.81 ± 0.25 | 1.19 ± 0.80 | 0.75 ± 0.27 | 0.69 ± 0.65 |
| 5 | 0.67 ± 0.67 | 1.13 ± 0.58 | 0.25 ± 0.38 | 0.67 ± 0.41 | 0.13 ± 0.25 |
| 8 | 0.92 ± 0.37 | 0.44 ± 0.42 | 0.94 ± 0.82 | 0.33 ± 0.61 | 0.31 ± 0.37 |
| AUC | 7.015 | 5.675 | 5.515 | 6.090 | 2.990 |

Example 3

Inhibition of Influenza A Virus in Tissue Culture Using Splice Site-Targeted Antisense Oligomers An aspect of the present invention is the inhibition of influenza A virus replication by antisense targeting of multiple sites within the M1/M2 segment. In addition to inhibition of translation by targeting the common M1/M2 AUG start site, splice donor and splice acceptor sites can also be targeted using compounds of the invention. Two PMO that target the splice acceptor site at position 740 were synthesized as peptide conjugated PPMOs, SA740 and SA746 (SEQ ID NOs: 26 and 29, respectively) and placed into an in vitro tissue culture replication system for H1N1 strain PR8. The P007 cell penetrating peptide (SEQ ID NO: 118) was conjugated to the 3' terminus of the PMO.

An alveolar murine macrophage cell line (ATCC; AMJ2-C11) was infected at 0.1 MOI with H1N1 (strain PR8) and 1 hour post-infection PPMOs were added. Cells were incubated at 35 degrees C. overnight. Viral supernatant was then taken and incubated with VNAR protease to release viral RNA. HA RNA was quantified by quantitative real-time PCR (qRT-PCR). Cells were washed, fixed, and permeabilized. M1 and M2 proteins were then probed with monoclonal antibodies for 30 min at 37 degrees C. Cells were washed and anti-mouse IgG conjugated with Alexa 646 was added for 15 min at room temperature. M1 and M2 were then assayed by flow cytometry. To determine M1 and M2 protein levels, the percent of M1 or M2 positive cells was multiplied by the mean flourescent intensity of M1 or M2. Each sample was then divided by the untreated control to generate the percent of M1 or M2 compared to untreated scramble controls.

Figure 8A:
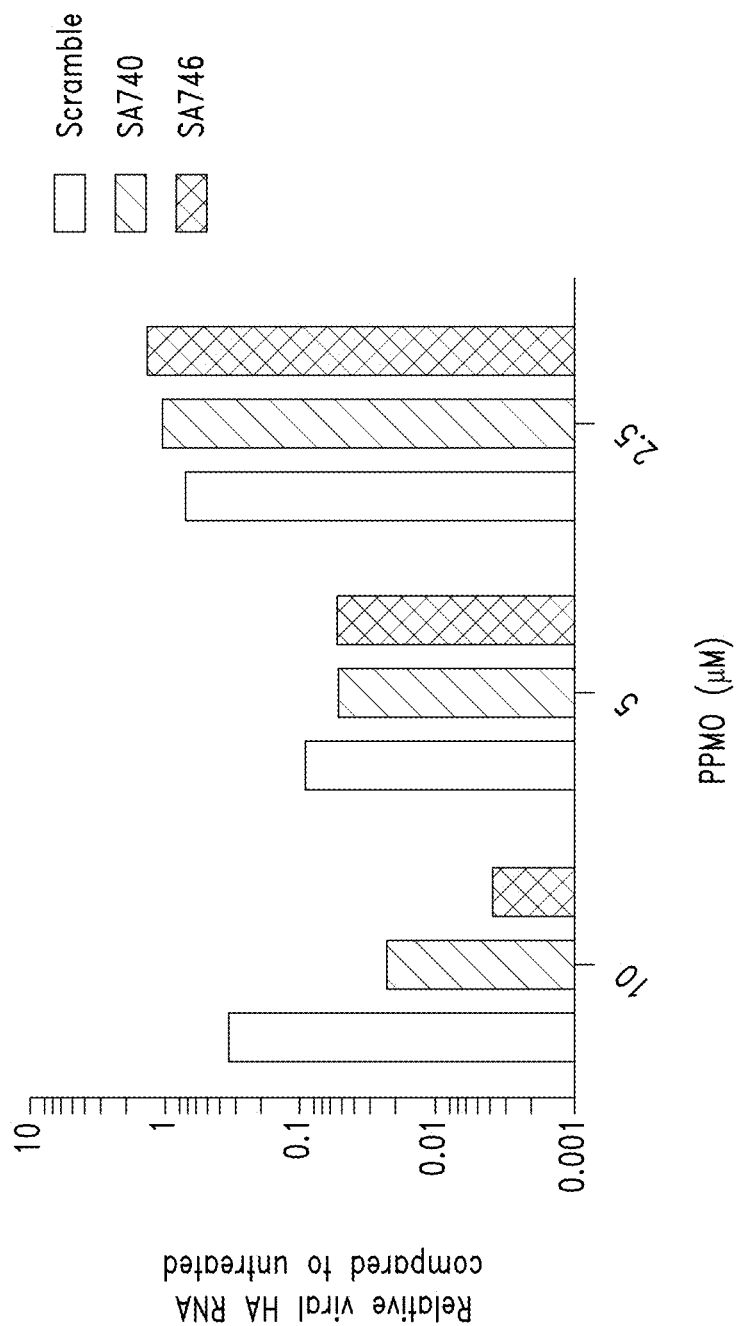
FIGS. 8A-C show the effect of PPMO targeted to the splice acceptor site on viral HA RNA, M1 protein and M2 protein expression, respectively.
Figure 8B:
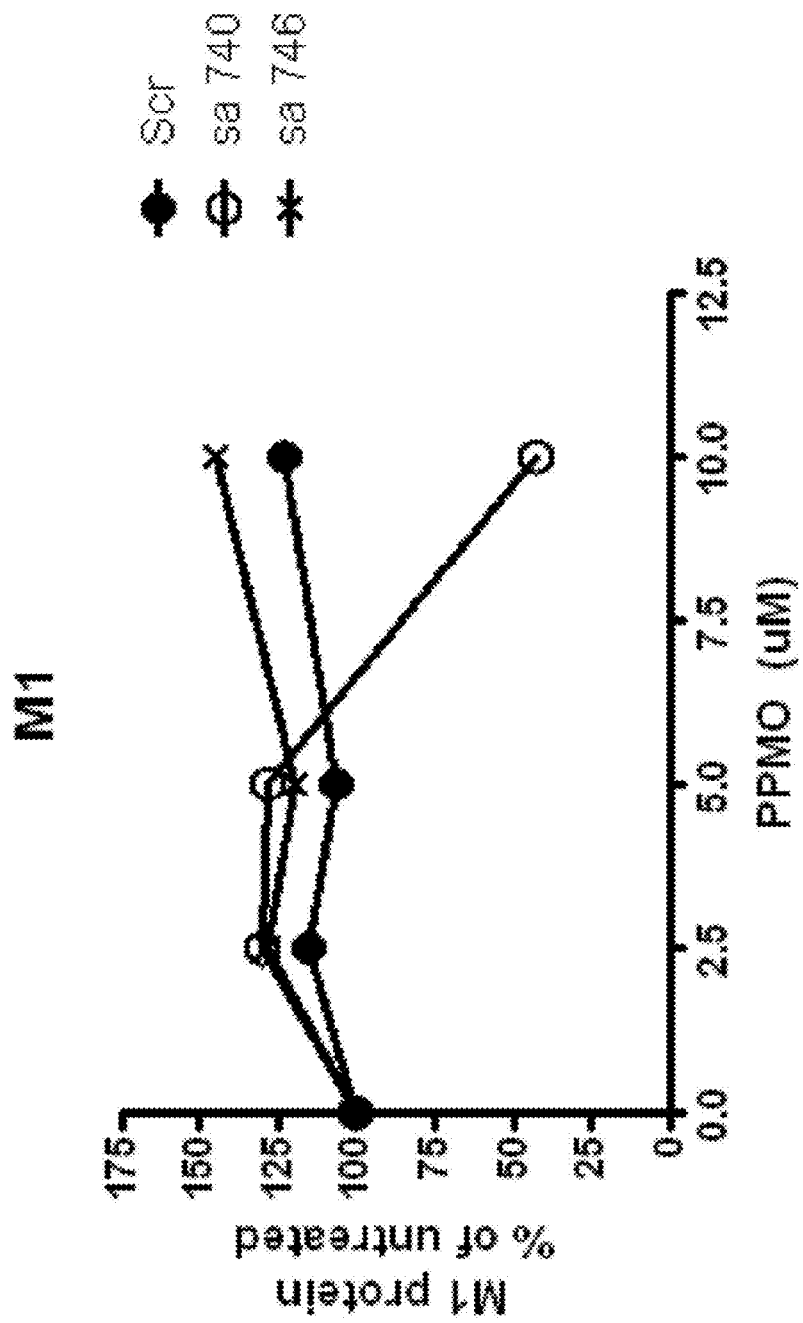
Figure 8C:
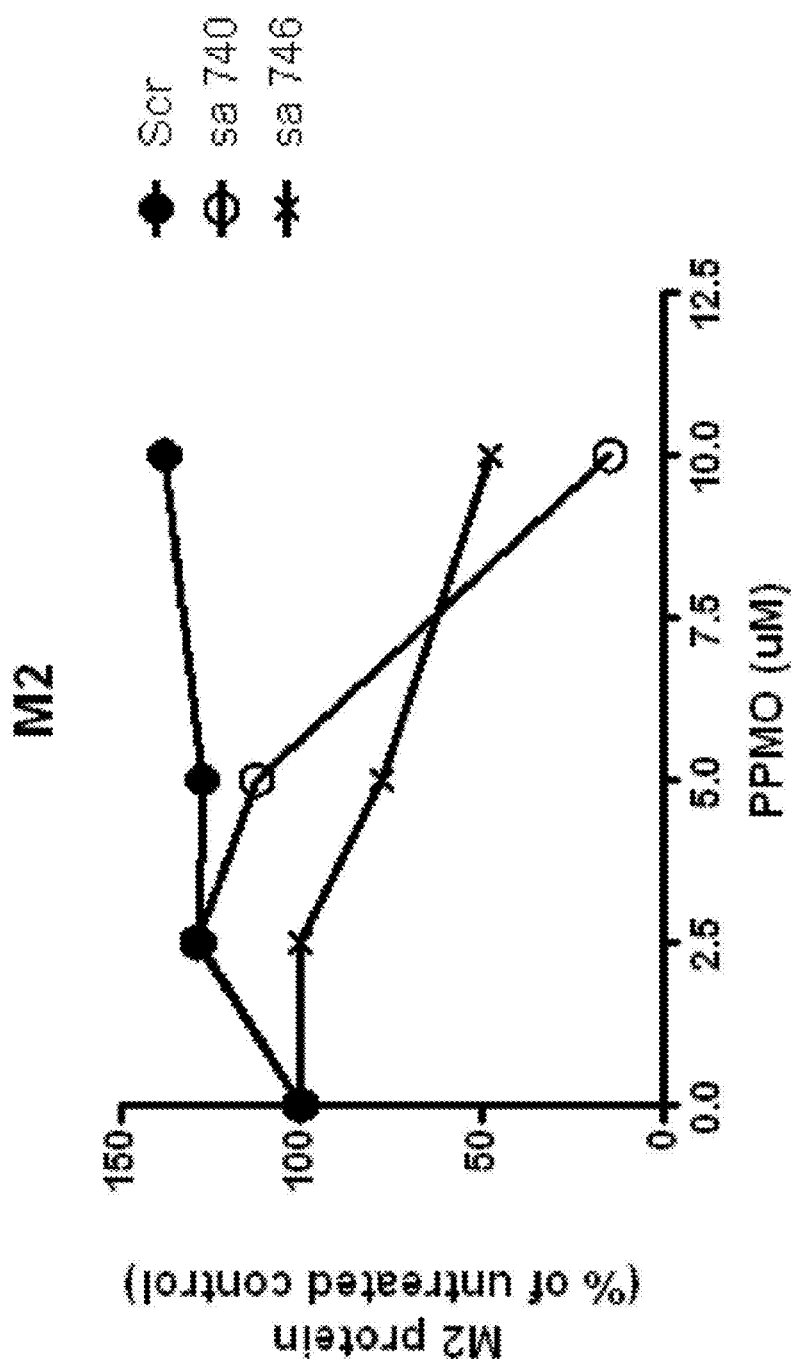

FIG. 8A shows the reduction in viral HA RNA levels (measured using qRT-PCR). Both SA740 and SA746 inhibited HA RNA production indicating an inhibition of viral replication compared to the scramble control. The most profound effect was observed at 10 micromolar with an approximate two-log reduction using SA746 and one-log reduction with SA740. FIGS. 8B and 8C show the effect of SA740 and SA746 on M1 and M2 protein levels, respectively. The flow cytometry method described above was used to determine relative protein levels. Both oligomers inhibited the production of the M2 protein whereas M1 protein levels were reduced by SA740.

Example 4

Figure 9A:
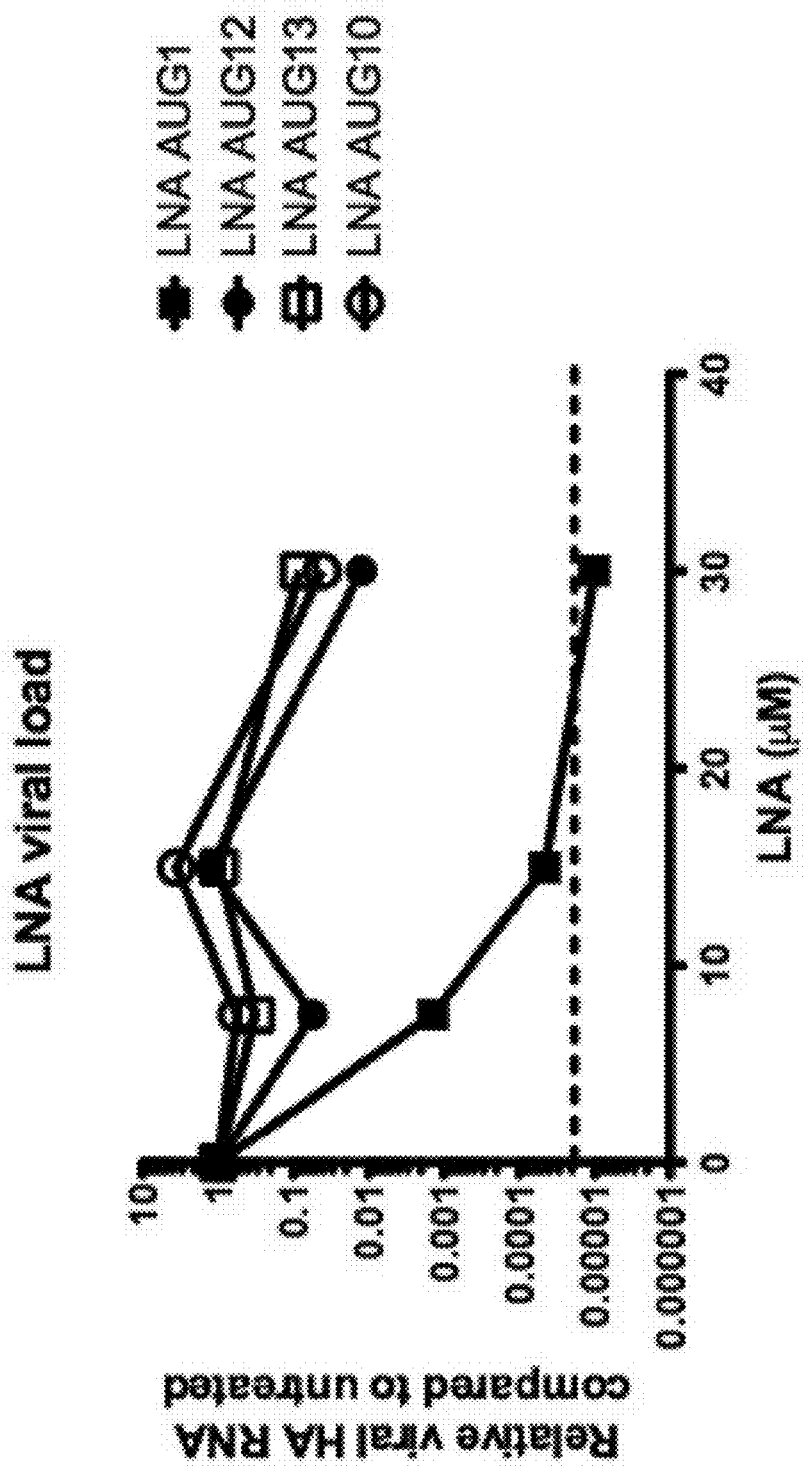
FIGS. 9A-B show the effect of antisense LNA oligomers targeted to the M1/M2 AUG start codon on viral HA RNA and M2 protein expression.
Figure 9B:
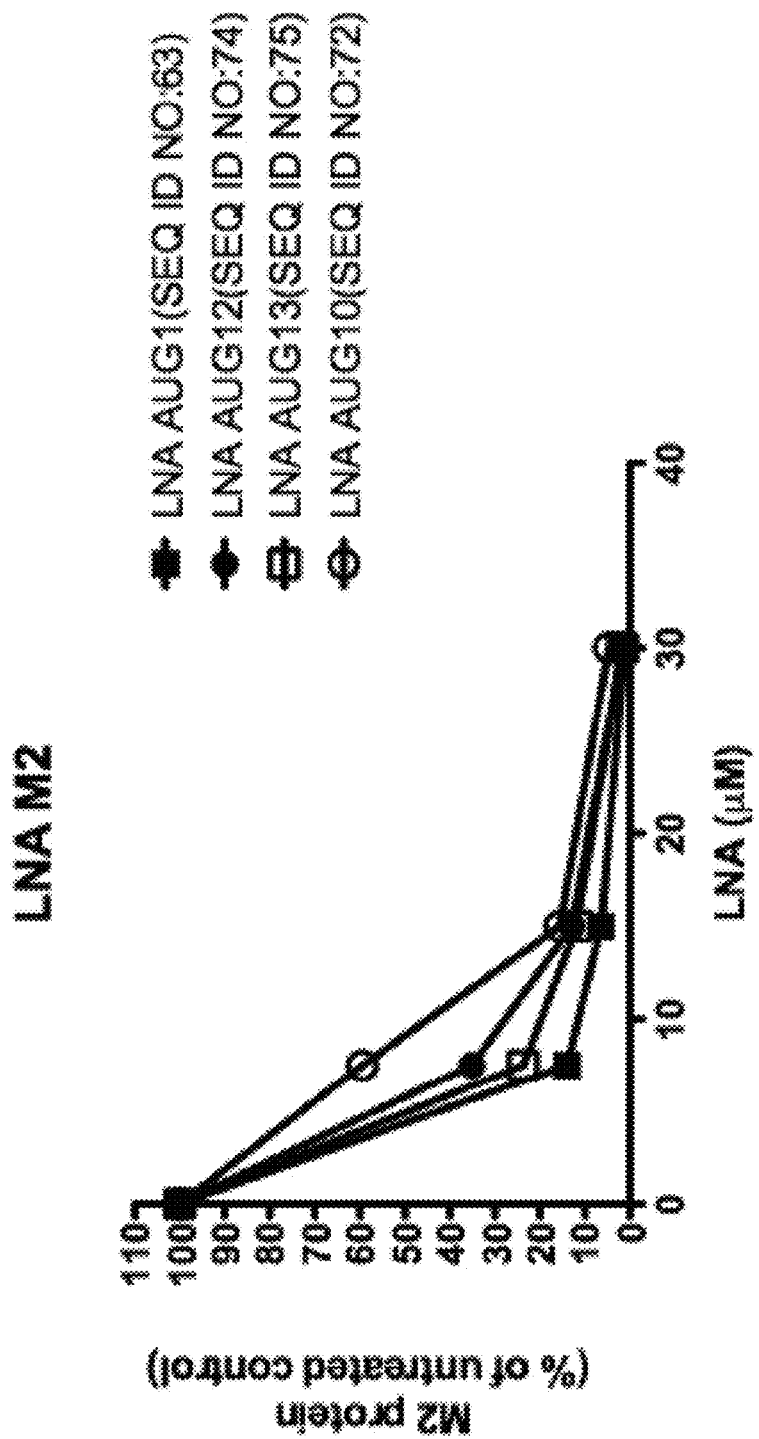

Inhibition of Influenza A Virus in Tissue Culture Using Locked Nucleic Acid Oligomers The compounds of the present invention include oligonucleotide analogs comprised of different chemical entities than PMO. A series of locked nucleic acids that target the M1/M2 segment AUG start site region were synthesized (LNA-AUG1, LNA-AUG12, LNA-AUG13 and LNA-AUG10; SEQ ID NOs: 63, 74, 75 and 72, respectively) and tested in the same assay for viral RNA and M2 protein expression as described above in Example 3. Intracellular delivery of the LNA oligomers was by way of gymnotic delivery (Stein, Hansen et al. 2010). AMJ2-C11 cells were infected with PR8 for 1 h and then washed. The cells were then plated in a 96 well plate with LNA or 2'OMe compounds and allowed to incubate overnight at 35 degrees C. Viral RNA levels and M2 protein expression were assessed at that time (approximately 18 hours total incubation time). FIG. 9A shows the effect of the four different LNAs on viral RNA levels (the HA segment). At 7.5 micromolar there was an approximately 3-log reduction in viral HA RNA levels for the LNA-AUG1 oligomer compared to an approximately 1.5 log reduction for the LNA-AUG12 compound (SEQ ID NOs: 63 and 74, respectively). LNA-AUG1 is a 20mer whereas LNA-AUG12 is a 16mer. There is a rank order of effectiveness according to length for all four LNA oligomers indicating the longer LNAs are preferred embodiments of the invention. This relationship is also observed in the measurement of M2 protein expression shown in FIG. 9B with the LNA-AUG1 oligo being most effective at compared to the LNA-AUG10 compound at 7.5 micromolar (SEQ ID NOs: 63 and 72, respectively). The relatively short LNA-AUG10 compound consisting of a 10 base targeting sequence was the least effective in both the viral HA RNA and M2 protein expression assays.

Example 5

Inhibition of Influenza A Virus in Tissue Culture Using 2'Ome Oligomers

The compounds of the present invention also include antisense analog oligomers consisting of 2'OMe residues linked by phosphorothioate linkages. Three 2'OMe oligos were produced by IDT, 2'OMe-AUG1, 2'OMe-AUG2 and 2'OMe-SA1; SEQ ID NOs: 12, 20 and 26, respectively. These oligomers were designed to target either the AUG start codon of the M1/M2 segment or the splice acceptor site located at nucleotide 740. The 2'OMe-SA1 sequence (SEQ ID NO: 26) matches that of the PPMO compound described in Example 3 above as SA740. The 2'OMe compounds were tested in the same assay for their ability to inhibit viral HA RNA levels and M2 protein expression as described above in Examples 3 and 4. Intracellular delivery was attained through gymnosis as described above for LNAs in Example 4.

Figure 10A:
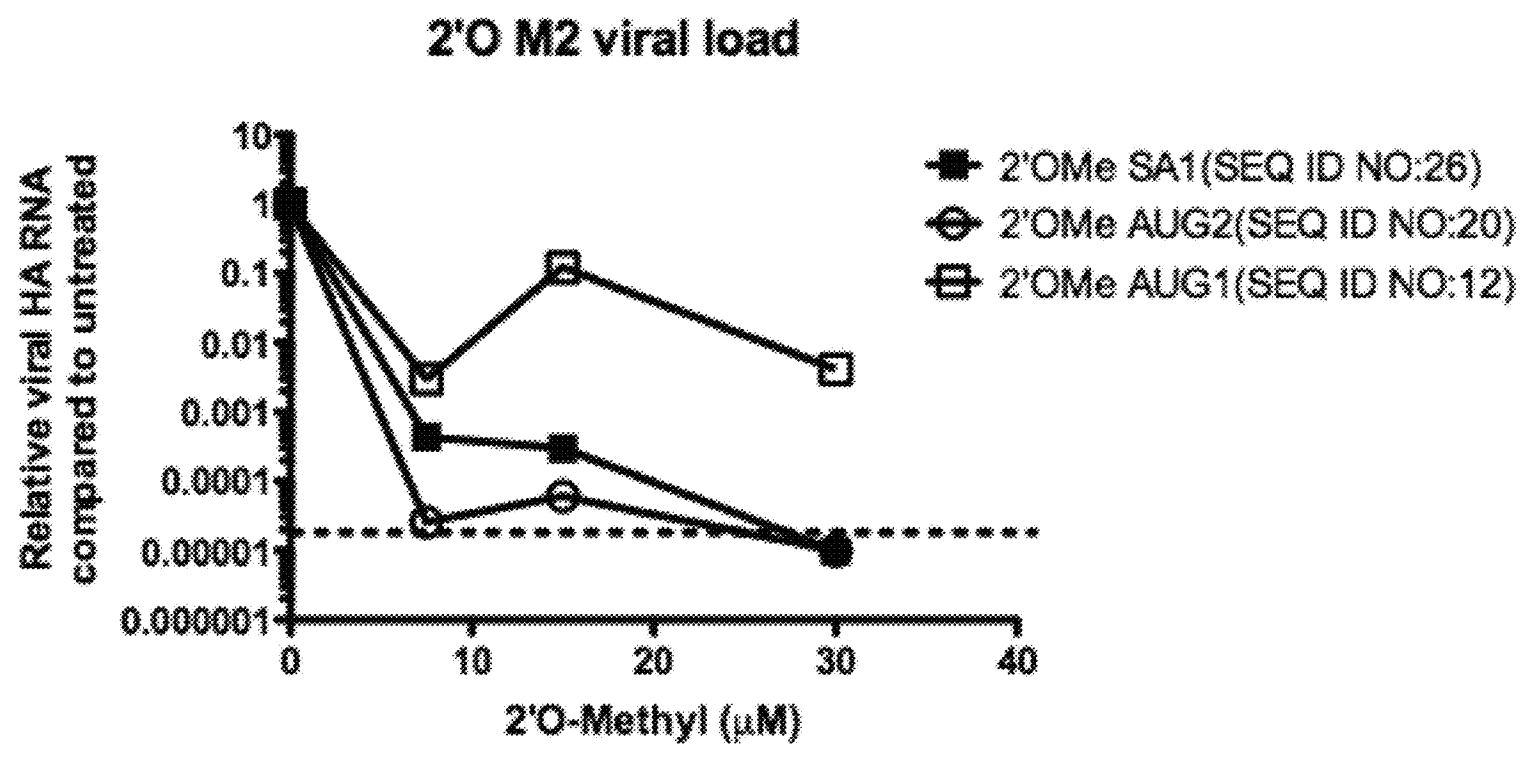
Figure 10B:
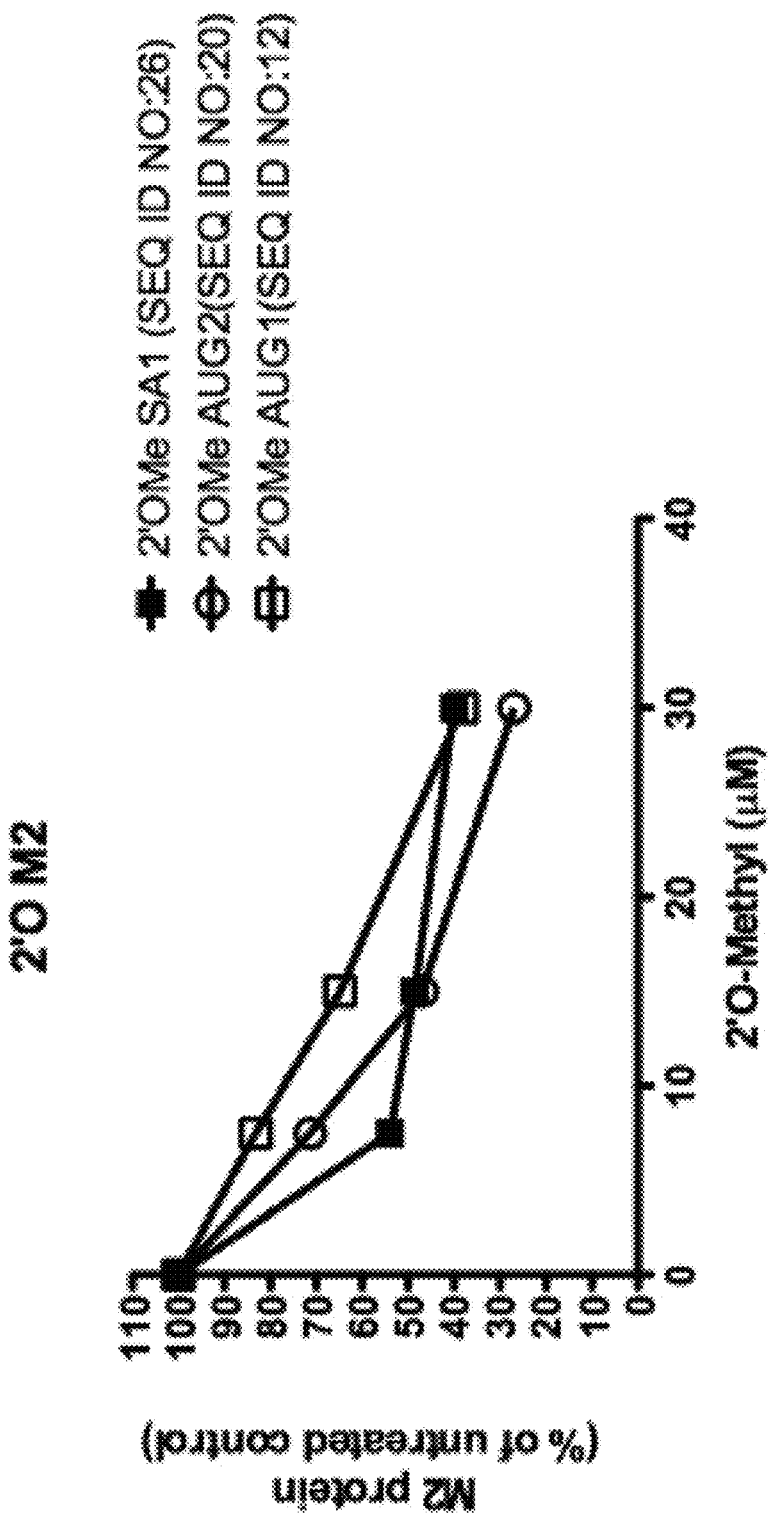

All three 2'OMe compounds were effective at reducing viral HA RNA levels from between 2.5 and 4.5 logs at 7.5 micromolar as shown in FIG. 10A. The relative effectiveness of the three compounds was also observed in the M2 protein measurement assays as shown in FIG. 10B. The most effective compound was the 2'OMe-AUG2 24mer that targets the AUG start site region (SEQ ID NO:20). Similarly effective was the 2'OMe-SA1 oligomer (SEQ ID NO:26) that targets the downstream M1/M2 splice acceptor site.

Example 6

Inhibition of M1 and M2 Protein Expression In Vitro

Figure 11:
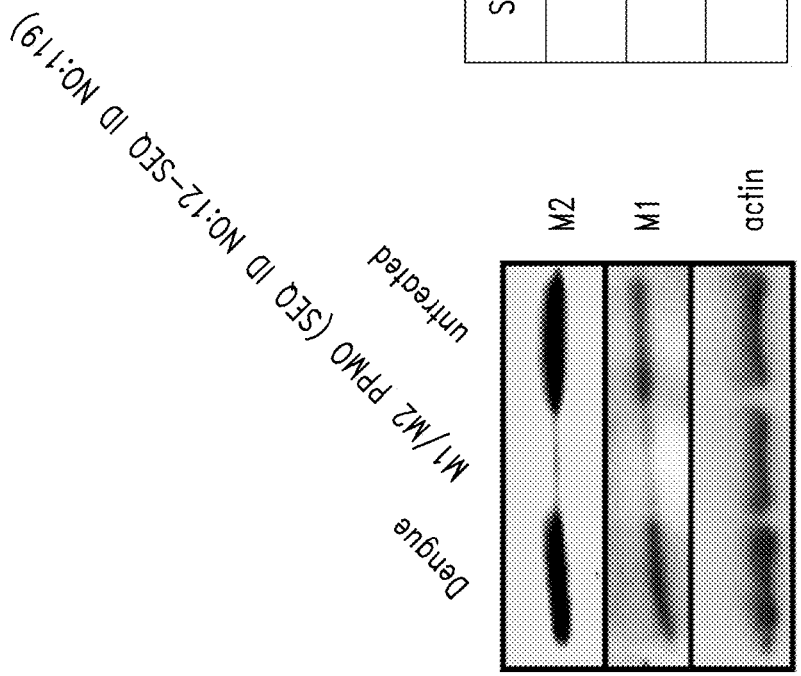
FIG. 11 shows the inhibition of M1 and M2 protein expression in H1N1 PR8-infected MDCK cells treated with a PPMO targeted to the M1/M2 AUG start codon.

The effect of an exemplary compound of the invention on M1 and M2 protein expression was evaluated using a western blot analysis of treated and infected AMJ2-C11 cells. An exemplary PPMO compound of the invention (M1/M2 PPMO; P007-M1/M2-AUG; SEQ ID NO: 12 conjugated at the 3' end to SEQ ID NO: 118) was used to treat MDCK cells overnight at 3 micromolar. The cells were then subsequently infected with H1N1-PR8 at 0.01 MOI for 1 hour and washed. 18 hours post-infection the cells were lysed and protein extracted. Equal amounts of protein were loaded onto gels for subsequent analysis by a standard immunoblot (western) assay using monoclonal antibodies that react with the M1, M2 and actin proteins. As shown in FIG. 11, the expression of both M1 and M2 proteins was reduced compared to an untreated control and an irrelevant control PPMO (Dengue). Analysis of the signal intensity indicated that M2 protein expression was inhibited by the M1/M2 PPMO to a greater extent than M1 protein expression as shown in FIG. 11 (i.e., 9% for M2 versus 27% for M1). The signal comparison for M1 and M2 were normalized to the actin control.

The invention claimed is:

1. An antiviral antisense oligonucleotide consisting of the following structure:

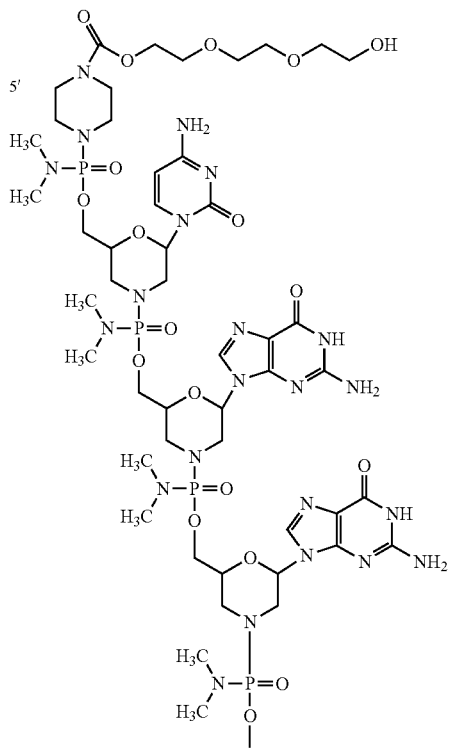

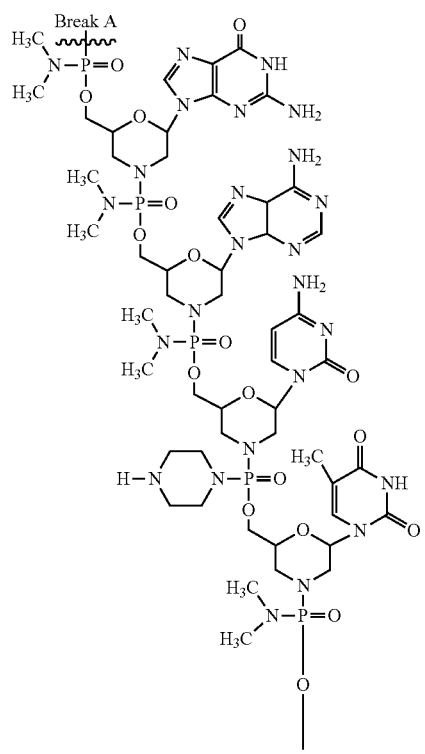

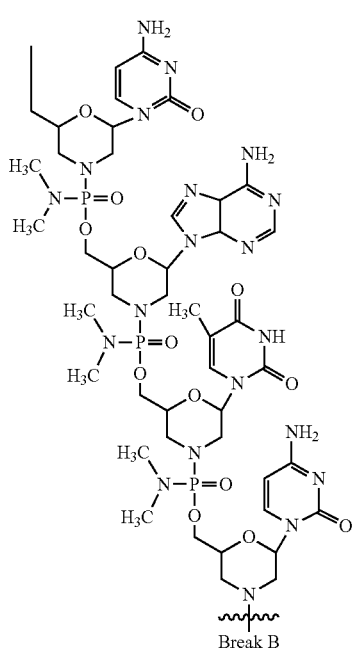

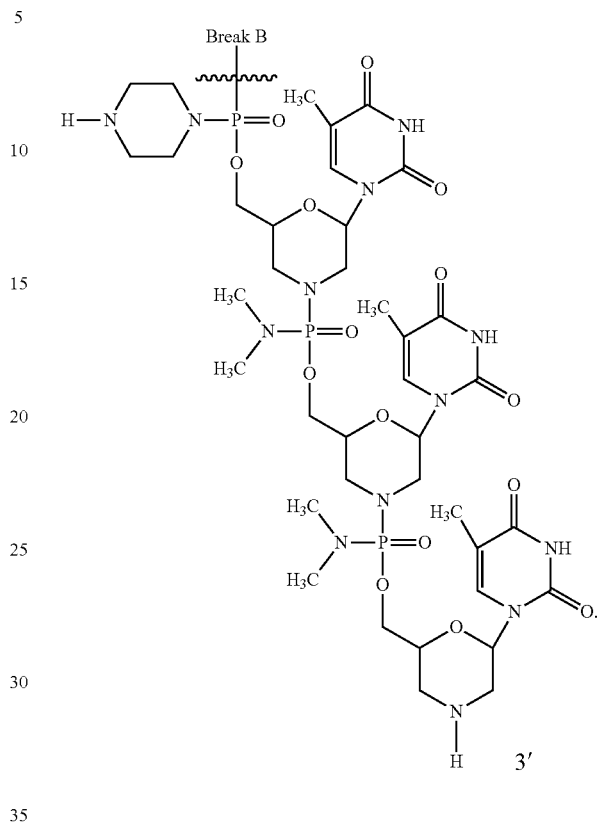

2. The antiviral antisense oligonucleotide of claim 1, wherein the antiviral antisense oligonucleotide is conjugated to an arginine-rich polypeptide that enhances the uptake of the compound into host cells.

3. The antiviral antisense oligonucleotide of claim 2, wherein the arginine-rich polypeptide is any one of SEQ ID NOS:115-128.

4. A pharmaceutical composition, comprising a pharmaceutically acceptable carrier, and an antiviral antisense oligonucleotide consisting of the following structure:

121
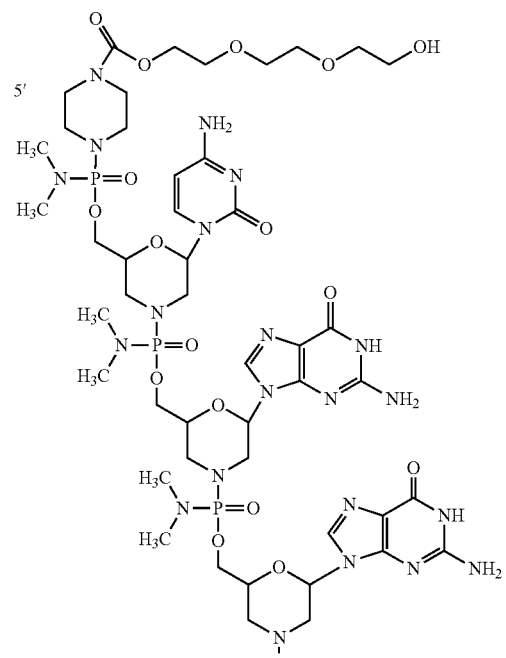
122
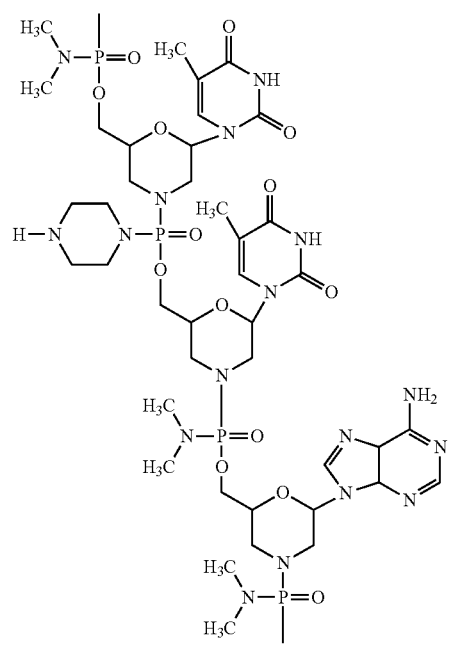

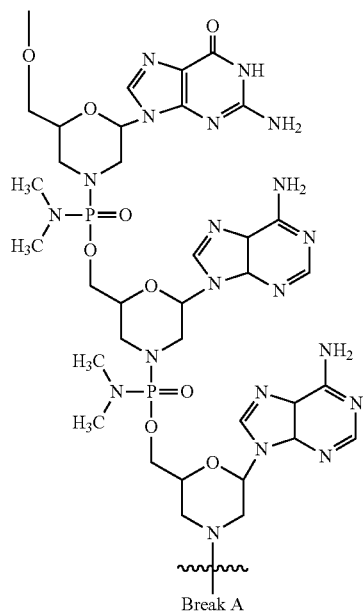
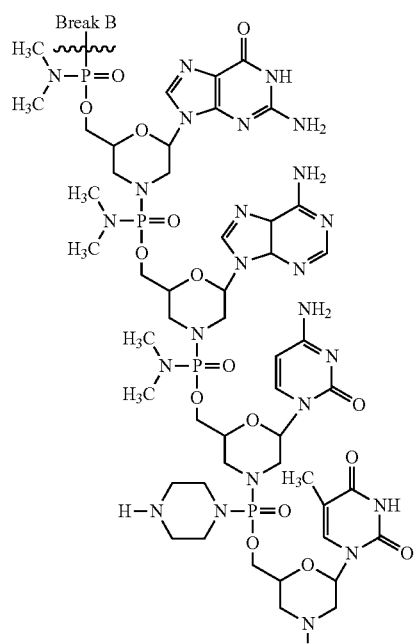
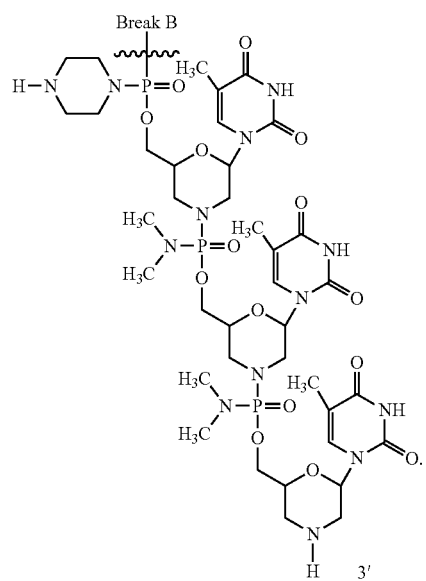

-continued

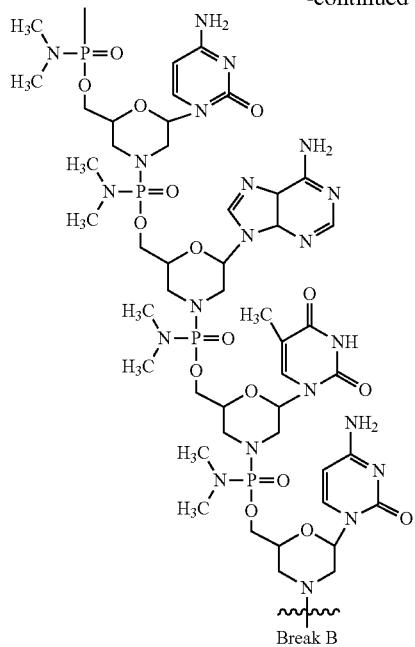

Break B

5. The pharmaceutical composition of claim 4, wherein the antiviral antisense oligonucleotide is conjugated to an arginine-rich polypeptide that enhances the uptake of the compound into host cells.

6. The pharmaceutical composition of claim 5, wherein the arginine-rich polypeptide is any one of SEQ ID NOS:115-128.

7. The pharmaceutical composition of any one of claims 4-6, further comprising an antibiotic.

8. The pharmaceutical composition of claim 7, wherein the antibiotic is bacteriostatic or bactericidal.

9. The pharmaceutical composition of claim 7, wherein the antibiotic is a beta-lactam.

10. The pharmaceutical composition of claim 7, wherein the antibiotic is selected from penicillin, amoxicillin, cephalosporin, chloramphenicol, or clindamycin.

11. The pharmaceutical composition of any one of claims 4-6, further comprising a second oligonucleotide targeted against an RNA molecule encoding CD200 or the CD200 receptor.

12. A method of reducing replication of an Influenza A virus, comprising contacting an Influenza A virus infected cell with an antiviral antisense oligonucleotide consisting of the following structure:

-continued
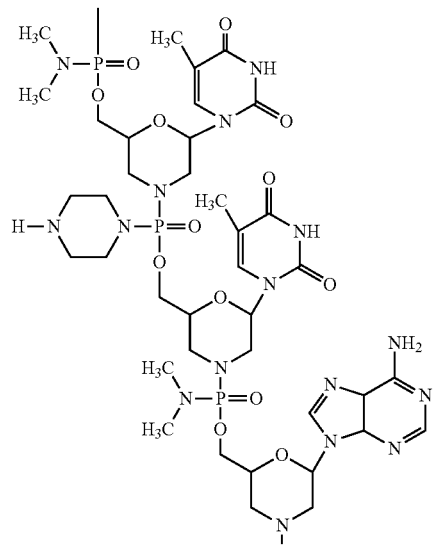
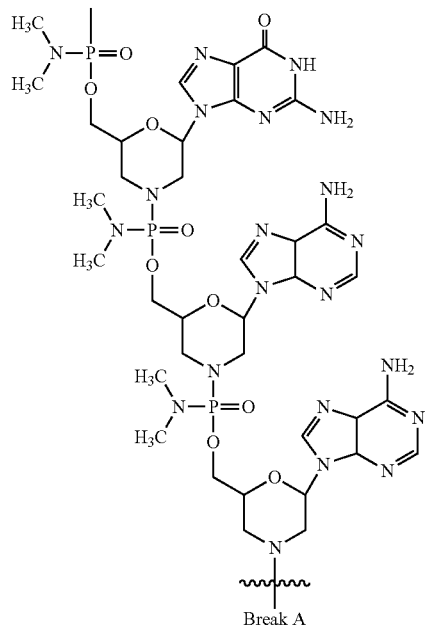
Break A

-continued

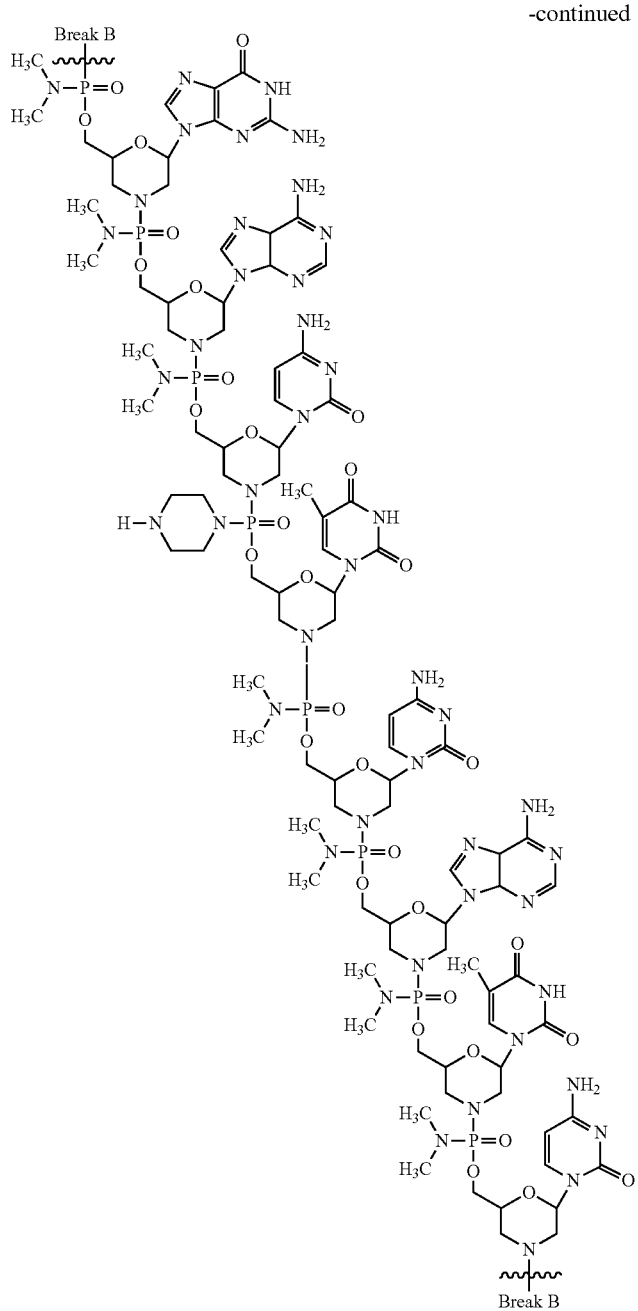
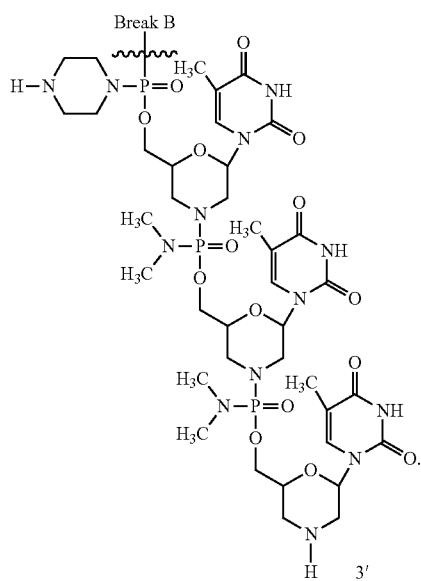

13. The method of claim 12, wherein the method comprises administering the antiviral antisense oligonucleotide to a subject having an Influenza A virus infected cell.

14. The method of claim 13, further comprising administering an antibiotic in combination with the antiviral antisense oligonucleotide when the subject has a secondary bacterial infection.

15. The method of claim 14, wherein the antibiotic is administered separately from the antiviral antisense oligonucleotide.

16. The method of claim 14, wherein the antibiotic is administered concurrently with the antiviral antisense oligonucleotide.

17. The method of claim 14, wherein the antibiotic is bacteriostatic or bactericidal.

18. The method of claim 14, wherein the antibiotic is a beta-lactam.

19. The method of claim 14, wherein the antibiotic is selected from penicillin, amoxicillin, cephalosporin, chloramphenicol, or clindamycin.

20. The method of claim 14, wherein the secondary bacterial infection is a Streptococcal infection.

21. The method of claim 20, wherein the Streptococcal infection is a *Streptococcus pneuomoniae* infection.

22. The method of claim 12, further comprising administering a second antisense oligonucleotide targeted against an RNA molecule encoding CD200 or the CD200 receptor separately or concurrently in combination with the antiviral antisense oligonucleotide.

23. The method of claim 22, wherein the second antisense oligonucleotide targeted against an RNA molecule encoding CD200 or the CD200 receptor is administered separately from the antiviral antisense oligonucleotide.

24. The method of claim 22, wherein the second antisense oligonucleotide targeted against an RNA molecule encoding CD200 or the CD200 receptor is administered concurrently with the antiviral antisense oligonucleotide.

25. The method of claim 14, further comprising administering an antisense oligonucleotide targeted against an RNA molecule encoding CD200 or the CD200 receptor, separately or concurrently in combination with the antiviral antisense oligonucleotide.

26. The method of claim 25, wherein the second antisense oligonucleotide targeted against an RNA molecule encoding CD200 or the CD200 receptor is administered separately from the antiviral antisense oligonucleotide.

27. The method of claim 25, wherein the second antisense oligonucleotide targeted against an RNA molecule encoding CD200 or the CD200 receptor is administered concurrently with the antiviral antisense oligonucleotide.

28. The antiviral antisense oligonucleotide of claim 1, wherein the antiviral antisense oligonucleotide is linked to a polyethylene glycol moiety.

29. The pharmaceutical composition of claim 4, wherein the antiviral antisense oligonucleotide is linked to a polyethylene glycol moiety.

30. The method of claim 12, wherein the antiviral antisense oligonucleotide is linked to a polyethylene glycol moiety.

31. The pharmaceutical composition of claim 4, further comprising an additional influenza virus-targeted therapy.

32. The pharmaceutical composition of claim 31, wherein the additional influenza virus-targeted therapy is oseltamivir phosphate.

33. The method of claim 12, further comprising administering an additional influenza virus-targeted therapy separately or concurrently in combination with the antiviral antisense oligonucleotide.

34. The method of claim 33, wherein the additional influenza virus-targeted therapy is administered concurrently with the antiviral antisense oligonucleotide.

35. The method of claim 33, wherein the additional influenza virus-targeted therapy is administered separately from the antiviral antisense oligonucleotide.

36. The method of claim 33, wherein the additional influenza virus-targeted therapy is oseltamivir phosphate.

\* \* \* \* \*

SEQUENCE LISTING

```
<160> NUMBER OF SEQ ID NOS: 133

<210> SEQ ID NO 1
<211> LENGTH: 60
<212> TYPE: RNA
<213> ORGANISM: Influenza A virus

<400> SEQUENCE: 1
agcaaaagca gguagauauu uaaagaugag ucuucuaacc gaggucgaaa cguacguucu    60

<210> SEQ ID NO 2
<211> LENGTH: 45
<212> TYPE: RNA
<213> ORGANISM: Influenza A virus

<400> SEQUENCE: 2
aagcagguag auauuuaaag augagucuuc uaaccgaggu cgaaa                    45

<210> SEQ ID NO 3
<211> LENGTH: 25
<212> TYPE: RNA
<213> ORGANISM: Influenza A virus

<400> SEQUENCE: 3
agcaaaagca gguagauauu uaaag                                          25

<210> SEQ ID NO 4
```

-continued

<211> LENGTH: 25
<212> TYPE: RNA
<213> ORGANISM: Influenza A virus

<400> SEQUENCE: 4
cuuuaaauau cuaccugcuu uugcu 25

<210> SEQ ID NO 5
<211> LENGTH: 60
<212> TYPE: RNA
<213> ORGANISM: Influenza A virus

<400> SEQUENCE: 5
agcgaaagca gguagauauu gaaagaugag ucuucuaacc gaggucgaaa cguacguucu 60

<210> SEQ ID NO 6
<211> LENGTH: 60
<212> TYPE: RNA
<213> ORGANISM: Influenza A virus

<400> SEQUENCE: 6
agcaaaagca gguagauauu gaaagaugag ucuucuaacc gaggucgaaa cguacguucu 60

<210> SEQ ID NO 7
<211> LENGTH: 60
<212> TYPE: RNA
<213> ORGANISM: Influenza A virus

<400> SEQUENCE: 7
agcaaaagca gguagauauu gaaagaugag ccuucuaacc gaggucgaaa cguauguucu 60

<210> SEQ ID NO 8
<211> LENGTH: 60
<212> TYPE: RNA
<213> ORGANISM: Influenza A virus

<400> SEQUENCE: 8
agcaaaagca gguagauauu gaaagaugag ucuucuaacc gaggucgaaa cguacguucu 60

<210> SEQ ID NO 9
<211> LENGTH: 51
<212> TYPE: RNA
<213> ORGANISM: Influenza A virus

<400> SEQUENCE: 9
aaauuugcag gccuaccaga aacgaauggg agugcagaug cagcgauuca a 51

<210> SEQ ID NO 10
<211> LENGTH: 51
<212> TYPE: RNA
<213> ORGANISM: Influeza A virus

<400> SEQUENCE: 10
aaauuugcag gccuaccaga agcgaauggg agugcagaug cagcgauuca a 51

<210> SEQ ID NO 11
<211> LENGTH: 1027
<212> TYPE: DNA
<213> ORGANISM: Influenza A virus

<400> SEQUENCE: 11
agcgaaagca ggtagatatt gaaagatgag tcttctaacc gaggtcgaaa cgtacgttct 60
ctctatcatc ccgtcaggcc ccctcaaagc cgagatcgca cagagacttg aagatgtctt 120

```
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg gggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct ttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                             1027
```

<210> SEQ ID NO 12
<211> LENGTH: 20
<212> TYPE: DNA
<213> ORGANISM: Artificial Sequence
<220> FEATURE:
<223> OTHER INFORMATION: PMO antisense targeting sequence

<400> SEQUENCE: 12
cggttagaag actcatcttt                                                 20

<210> SEQ ID NO 13
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (4)...(5)
<223> OTHER INFORMATION: Cationic linkage between bases
<220> FEATURE:
<221> NAME/KEY: misc_feature
<222> LOCATION: (12)...(13)
<223> OTHER INFORMATION: Cationic linkage between bases
<220> FEATURE:
<221> NAME/KEY: misc_feature
<222> LOCATION: (17)...(18)
<223> OTHER INFORMATION: Cationic linkage between bases

<400> SEQUENCE: 13
cggttagaag actcatcttt                                                 20

<210> SEQ ID NO 14
<211> LENGTH: 20
<212> TYPE: DNA
<213> ORGANISM: Artificial Sequence
<220> FEATURE:
<223> OTHER INFORMATION: PMO antisense targeting sequence

<400> SEQUENCE: 14
agaagactca tctttcaata         20

<210> SEQ ID NO 15
<211> LENGTH: 20
<212> TYPE: DNA
<213> ORGANISM: Artificial Sequence
<220> FEATURE:
<223> OTHER INFORMATION: PMO antisense targeting sequence

<400> SEQUENCE: 15
ttagaagact catctttcaa         20

<210> SEQ ID NO 16
<211> LENGTH: 20
<212> TYPE: DNA
<213> ORGANISM: Artificial Sequence
<220> FEATURE:
<223> OTHER INFORMATION: PMO antisense targeting sequence

<400> SEQUENCE: 16
ctcggttaga agactcatct         20

<210> SEQ ID NO 17
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 17
atctttcaat atctacctgc ttttg         25

<210> SEQ ID NO 18
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 18
ctcatctttc aatatctacc tgctt         25

<210> SEQ ID NO 19
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 19
ctcggttaga agactcatct ttcaa         25

<210> SEQ ID NO 20
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 20
acctcggtta gaagactcat ctttc         25

<210> SEQ ID NO 21
<211> LENGTH: 25
<212> TYPE: DNA
<213> ORGANISM: Artificial Sequence

```
<220> FEATURE:
<223> OTHER INFORMATION: PMO antisense targeting sequence

<400> SEQUENCE: 21
tcgacctcgg ttagaagact catct                                              25

<210> SEQ ID NO 22
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 22
tttcgacctc ggttagaaga ctcat                                              25

<210> SEQ ID NO 23
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 23
agcaaaagca ggtagatatt gaaaa                                              25

<210> SEQ ID NO 24
<211> LENGTH: 25
<212> TYPE: DNA
<213> ORGANISM: Artificial Sequence
<220> FEATURE:
<223> OTHER INFORMATION: PMO antisense targeting sequence

<400> SEQUENCE: 24
agcaggtaga tattgaaaaa tgagt                                              25

<210> SEQ ID NO 25
<211> LENGTH: 24
<212> TYPE: DNA
<213> ORGANISM: Artificial Sequence
<220> FEATURE:
<223> OTHER INFORMATION: PMO antisense targeting sequence

<400> SEQUENCE: 25
ctcccattcg cttctggtag gcct                                               24

<210> SEQ ID NO 26
<211> LENGTH: 24
<212> TYPE: DNA
<213> ORGANISM: Artificial Sequence
<220> FEATURE:
<223> OTHER INFORMATION: PMO antisense targeting sequence

<400> SEQUENCE: 26
cactcccatt cgcttctggt aggc                                               24

<210> SEQ ID NO 27
<211> LENGTH: 24
<212> TYPE: DNA
<213> ORGANISM: Artificial Sequence
<220> FEATURE:
<223> OTHER INFORMATION: PMO antisense targeting sequence

<400> SEQUENCE: 27
tgcactccca ttcgcttctg gtag                                               24
```

-continued

<210> SEQ ID NO 28
<211> LENGTH: 24
<212> TYPE: DNA
<213> ORGANISM: Artificial Sequence
<220> FEATURE:
<223> OTHER INFORMATION: PMO antisense targeting sequence

<400> SEQUENCE: 28
tctgcactcc cattcgcttc tggt                                          24

<210> SEQ ID NO 29
<211> LENGTH: 24
<212> TYPE: DNA
<213> ORGANISM: Artificial Sequence
<220> FEATURE:
<223> OTHER INFORMATION: PMO antisense targeting sequence

<400> SEQUENCE: 29
catctgcact cccattcgct tctg                                          24

<210> SEQ ID NO 30
<211> LENGTH: 22
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: modified_base
<222> LOCATION: 12
<223> OTHER INFORMATION: I

<400> SEQUENCE: 30
agcaaaagca gngtagataa tc                                            22

<210> SEQ ID NO 31
<211> LENGTH: 22
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: modified_base
<222> LOCATION: 12
<223> OTHER INFORMATION: I
<220> FEATURE:
<221> NAME/KEY: misc_feature
<222> LOCATION: (13)...(4)
<223> OTHER INFORMATION: Cationic linkage between bases
<220> FEATURE:
<221> NAME/KEY: misc_feature
<222> LOCATION: (17)...(18)
<223> OTHER INFORMATION: Cationic linkage between bases
<220> FEATURE:
<221> NAME/KEY: misc_feature
<222> LOCATION: (20)...(21)
<223> OTHER INFORMATION: Cationic linkage between bases

<400> SEQUENCE: 31
agcaaaagca gngtagataa tc                                            22

<210> SEQ ID NO 32
<211> LENGTH: 22
<212> TYPE: DNA
<213> ORGANISM: Artificial Sequence
<220> FEATURE:
<223> OTHER INFORMATION: PMO antisense targeting sequence

<400> SEQUENCE: 32
cggattgaca tccattcaaa tg                                            22

```
<210> SEQ ID NO 33
<211> LENGTH: 22
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (5)...(6)
<223> OTHER INFORMATION: Cationic linkage between bases
<220> FEATURE:
<221> NAME/KEY: misc_feature
<222> LOCATION: (10)...(11)
<223> OTHER INFORMATION: Cationic linkage between bases
<220> FEATURE:
<221> NAME/KEY: misc_feature
<222> LOCATION: (15)...(16)
<223> OTHER INFORMATION: Cationic linkage between bases

<400> SEQUENCE: 33
cggattgaca tccattcaaa tg                                             22

<210> SEQ ID NO 34
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (3)...(4)
<223> OTHER INFORMATION: Cationic linkage between bases
<220> FEATURE:
<221> NAME/KEY: misc_feature
<222> LOCATION: (7)...(8)
<223> OTHER INFORMATION: Cationic linkage between bases
<220> FEATURE:
<221> NAME/KEY: misc_feature
<222> LOCATION: (15)...(16)
<223> OTHER INFORMATION: Cationic linkage between bases

<400> SEQUENCE: 34
ctttcaatat ctacctgctt                                                20

<210> SEQ ID NO 35
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (1)...(2)
<223> OTHER INFORMATION: Cationic linkage between bases
<220> FEATURE:
<221> NAME/KEY: misc_feature
<222> LOCATION: (4)...(5)
<223> OTHER INFORMATION: Cationic linkage between bases
<220> FEATURE:
<221> NAME/KEY: misc_feature
<222> LOCATION: (12)...(13)
<223> OTHER INFORMATION: Cationic linkage between bases

<400> SEQUENCE: 35
ctcatctttc aatatctacc                                                20

<210> SEQ ID NO 36
<211> LENGTH: 20
<212> TYPE: DNA
<213> ORGANISM: Artificial Sequence
<220> FEATURE:
```

```
<223> OTHER INFORMATION: PMO antisense targeting sequence
<220> FEATURE:
<221> NAME/KEY: misc_feature
<222> LOCATION: (2)...(3)
<223> OTHER INFORMATION: Cationic linkage between bases
<220> FEATURE:
<221> NAME/KEY: misc_feature
<222> LOCATION: (5)...(6)
<223> OTHER INFORMATION: Cationic linkage between bases
<220> FEATURE:
<221> NAME/KEY: misc_feature
<222> LOCATION: (13)...(14)
<223> OTHER INFORMATION: Cationic linkage between bases

<400> SEQUENCE: 36
actcatcttt caatatctac                                              20

<210> SEQ ID NO 37
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (3)...(4)
<223> OTHER INFORMATION: Cationic linkage between bases
<220> FEATURE:
<221> NAME/KEY: misc_feature
<222> LOCATION: (6)...(7)
<223> OTHER INFORMATION: Cationic linkage between bases
<220> FEATURE:
<221> NAME/KEY: misc_feature
<222> LOCATION: (14)...(15)
<223> OTHER INFORMATION: Cationic linkage between bases

<400> SEQUENCE: 37
gactcatctt tcaatatcta                                              20

<210> SEQ ID NO 38
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (4)...(5)
<223> OTHER INFORMATION: Cationic linkage between bases
<220> FEATURE:
<221> NAME/KEY: misc_feature
<222> LOCATION: (7)...(8)
<223> OTHER INFORMATION: Cationic linkage between bases
<220> FEATURE:
<221> NAME/KEY: misc_feature
<222> LOCATION: (15)...(16)
<223> OTHER INFORMATION: Cationic linkage between bases

<400> SEQUENCE: 38
agactcatct ttcaatatct                                              20

<210> SEQ ID NO 39
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (5)...(6)
<223> OTHER INFORMATION: Cationic linkage between bases
<220> FEATURE:
<221> NAME/KEY: misc_feature
```

```
<222> LOCATION: (7)...(8)
<223> OTHER INFORMATION: Cationic linkage between bases
<220> FEATURE:
<221> NAME/KEY: misc_feature
<222> LOCATION: (16)...(17)
<223> OTHER INFORMATION: Cationic linkage between bases

<400> SEQUENCE: 39
aagactcatc tttcaatatc                                                   20

<210> SEQ ID NO 40
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (6)...(7)
<223> OTHER INFORMATION: Cationic linkage between bases
<220> FEATURE:
<221> NAME/KEY: misc_feature
<222> LOCATION: (9)...(10)
<223> OTHER INFORMATION: Cationic linkage between bases
<220> FEATURE:
<221> NAME/KEY: misc_feature
<222> LOCATION: (17)...(18)
<223> OTHER INFORMATION: Cationic linkage between bases

<400> SEQUENCE: 40
gaagactcat ctttcaatat                                                   20

<210> SEQ ID NO 41
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (7)...(8)
<223> OTHER INFORMATION: Cationic linkage between bases
<220> FEATURE:
<221> NAME/KEY: misc_feature
<222> LOCATION: (10)...(11)
<223> OTHER INFORMATION: Cationic linkage between bases
<220> FEATURE:
<221> NAME/KEY: misc_feature
<222> LOCATION: (18)...(19)
<223> OTHER INFORMATION: Cationic linkage between bases

<400> SEQUENCE: 41
agaagactca tctttcaata                                                   20

<210> SEQ ID NO 42
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (8)...(9)
<223> OTHER INFORMATION: Cationic linkage between bases
<220> FEATURE:
<221> NAME/KEY: misc_feature
<222> LOCATION: (11)...(12)
<223> OTHER INFORMATION: Cationic linkage between bases
<220> FEATURE:
<221> NAME/KEY: misc_feature
<222> LOCATION: (19)...(20)
<223> OTHER INFORMATION: Cationic linkage between bases
```

```
<400> SEQUENCE: 42
tagaagactc atctttcaat                                               20

<210> SEQ ID NO 43
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (1)...(2)
<223> OTHER INFORMATION: Cationic linkage between bases
<220> FEATURE:
<221> NAME/KEY: misc_feature
<222> LOCATION: (9)...(10)
<223> OTHER INFORMATION: Cationic linkage between bases
<220> FEATURE:
<221> NAME/KEY: misc_feature
<222> LOCATION: (12)...(13)
<223> OTHER INFORMATION: Cationic linkage between bases

<400> SEQUENCE: 43
ttagaagact catctttcaa                                               20

<210> SEQ ID NO 44
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (2)...(3)
<223> OTHER INFORMATION: Cationic linkage between bases
<220> FEATURE:
<221> NAME/KEY: misc_feature
<222> LOCATION: (10)...(11)
<223> OTHER INFORMATION: Cationic linkage between bases
<220> FEATURE:
<221> NAME/KEY: misc_feature
<222> LOCATION: (13)...(14)
<223> OTHER INFORMATION: Cationic linkage between bases

<400> SEQUENCE: 44
gttagaagac tcatctttca                                               20

<210> SEQ ID NO 45
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (5)...(6)
<223> OTHER INFORMATION: Cationic linkage between bases
<220> FEATURE:
<221> NAME/KEY: misc_feature
<222> LOCATION: (13)...(14)
<223> OTHER INFORMATION: Cationic linkage between bases
<220> FEATURE:
<221> NAME/KEY: misc_feature
<222> LOCATION: (16)...(17)
<223> OTHER INFORMATION: Cationic linkage between bases

<400> SEQUENCE: 45
tcggttagaa gactcatctt                                               20

<210> SEQ ID NO 46
<211> LENGTH: 20
```

```
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (7)...(8)
<223> OTHER INFORMATION: Cationic linkage between bases
<220> FEATURE:
<221> NAME/KEY: misc_feature
<222> LOCATION: (15)...(16)
<223> OTHER INFORMATION: Cationic linkage between bases
<220> FEATURE:
<221> NAME/KEY: misc_feature
<222> LOCATION: (18)...(19)
<223> OTHER INFORMATION: Cationic linkage between bases

<400> SEQUENCE: 46
cctcggttag aagactcatc                                               20

<210> SEQ ID NO 47
<211> LENGTH: 20
<212> TYPE: DNA
<213> ORGANISM: Artificial Sequence
<220> FEATURE:
<223> OTHER INFORMATION: PMO antisense targeting sequence
<220> FEATURE:
<221> NAME/KEY: misc_feature
<222> LOCATION: (4)...(5)
<223> OTHER INFORMATION: Cationic linkage between bases
<220> FEATURE:
<221> NAME/KEY: misc_feature
<222> LOCATION: (9)...(10)
<223> OTHER INFORMATION: Cationic linkage between bases
<220> FEATURE:
<221> NAME/KEY: misc_feature
<222> LOCATION: (17)...(18)
<223> OTHER INFORMATION: Cationic linkage between bases

<400> SEQUENCE: 47
gacctcggtt agaagactca                                               20

<210> SEQ ID NO 48
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 48
cggttagaag actcatcttt                                               20

<210> SEQ ID NO 49
<211> LENGTH: 18
<212> TYPE: DNA
<213> ORGANISM: Artificial Sequence
<220> FEATURE:
<223> OTHER INFORMATION: PNA antisense targeting sequence

<400> SEQUENCE: 49
cggttagaag actcatct                                                 18

<210> SEQ ID NO 50
<211> LENGTH: 16
<212> TYPE: DNA
<213> ORGANISM: Artificial Sequence
<220> FEATURE:
<223> OTHER INFORMATION: PNA antisense targeting sequence

<400> SEQUENCE: 50
```
cggttagaag actcat                                             16

<210> SEQ ID NO 51
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 51
agaagactca tctttcaata                                         20

<210> SEQ ID NO 52
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 52
ttagaagact catctttcaa                                         20

<210> SEQ ID NO 53
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 53
ctcggttaga agactcatct                                         20

<210> SEQ ID NO 54
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 54
tcaatatcta cctgcttttg                                         20

<210> SEQ ID NO 55
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 55
ctttcaatat ctacctgctt                                         20

<210> SEQ ID NO 56
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 56
agcaaaagca ggtagatatt                                         20

<210> SEQ ID NO 57
<211> LENGTH: 20
<212> TYPE: DNA
<213> ORGANISM: Artificial Sequence

```
<220> FEATURE:
<223> OTHER INFORMATION: PNA antisense targeting sequence

<400> SEQUENCE: 57
agcaggtaga tattgaaaaa                                                   20

<210> SEQ ID NO 58
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 58
cattcgcttc tggtaggcct                                                   20

<210> SEQ ID NO 59
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 59
cccattcgct tctggtaggc                                                   20

<210> SEQ ID NO 60
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 60
ctcccattcg cttctggtag                                                   20

<210> SEQ ID NO 61
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 61
cactcccatt cgcttctggt                                                   20

<210> SEQ ID NO 62
<211> LENGTH: 20
<212> TYPE: DNA
<213> ORGANISM: Artificial Sequence
<220> FEATURE:
<223> OTHER INFORMATION: PNA antisense targeting sequence

<400> SEQUENCE: 62
tgcactccca ttcgcttctg                                                   20

<210> SEQ ID NO 63
<211> LENGTH: 20
<212> TYPE: DNA
<213> ORGANISM: Artificial Sequence
<220> FEATURE:
<223> OTHER INFORMATION: LNA antisense targeting sequence

<400> SEQUENCE: 63
cggttagaag actcatcttt                                                   20
```

```
<210> SEQ ID NO 64
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 64
gaagactcat                                                          10

<210> SEQ ID NO 65
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 65
gaagactcat                                                          10

<210> SEQ ID NO 66
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 66
gaagactcat                                                          10

<210> SEQ ID NO 67
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 67
agaagactca                                                          10

<210> SEQ ID NO 68
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 68
tagaagactc                                                          10

<210> SEQ ID NO 69
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 69
ttagaagact                                                          10

<210> SEQ ID NO 70
<211> LENGTH: 10
<212> TYPE: DNA
<213> ORGANISM: Artificial Sequence
<220> FEATURE:
<223> OTHER INFORMATION: LNA antisense targeting sequence
```

```
<400> SEQUENCE: 70
aagactcatc                                                          10

<210> SEQ ID NO 71
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 71
agactcatct                                                          10

<210> SEQ ID NO 72
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 72
gactcatctt                                                          10

<210> SEQ ID NO 73
<211> LENGTH: 10
<212> TYPE: DNA
<213> ORGANISM: Artificial Sequence
<220> FEATURE:
<223> OTHER INFORMATION: LNA antisense targeting sequence

<400> SEQUENCE: 73
actcatcttt                                                          10

<210> SEQ ID NO 74
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 74
cggttagaag actcat                                                   16

<210> SEQ ID NO 75
<211> LENGTH: 14
<212> TYPE: DNA
<213> ORGANISM: Artificial Sequence
<220> FEATURE:
<223> OTHER INFORMATION: LNA antisense targeting sequence

<400> SEQUENCE: 75
gttagaagac tcat                                                     14

<210> SEQ ID NO 76
<211> LENGTH: 11
<212> TYPE: DNA
<213> ORGANISM: Artificial Sequence
<220> FEATURE:
<223> OTHER INFORMATION: LNA antisense targeting sequence

<400> SEQUENCE: 76
gttagaagac t                                                        11

<210> SEQ ID NO 77
```

```
<211> LENGTH: 11
<212> TYPE: DNA
<213> ORGANISM: Artificial Sequence
<220> FEATURE:
<223> OTHER INFORMATION: LNA antisense targeting sequence

<400> SEQUENCE: 77
catctttaaa t                                                        11

<210> SEQ ID NO 78
<211> LENGTH: 17
<212> TYPE: DNA
<213> ORGANISM: Artificial Sequence
<220> FEATURE:
<223> OTHER INFORMATION: LNA antisense targeting sequence

<400> SEQUENCE: 78
catctttaaa tatctac                                                  17

<210> SEQ ID NO 79
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 79
cggttagaag actcat                                                   16

<210> SEQ ID NO 80
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 80
ggttagaaga ctcatc                                                   16

<210> SEQ ID NO 81
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 81
gttagaagac tcatct                                                   16

<210> SEQ ID NO 82
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 82
ttagaagact catctt                                                   16

<210> SEQ ID NO 83
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 83
```
tagaagactc atcttt                                          16

<210> SEQ ID NO 84
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 84
agaagactca tcttta                                          16

<210> SEQ ID NO 85
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 85
gaagactcat ctttaa                                          16

<210> SEQ ID NO 86
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 86
aagactcatc tttaaa                                          16

<210> SEQ ID NO 87
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 87
agactcatct ttaaat                                          16

<210> SEQ ID NO 88
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 88
gactcatctt taaata                                          16

<210> SEQ ID NO 89
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 89
actcatcttt aaatat                                          16

<210> SEQ ID NO 90
<211> LENGTH: 16
<212> TYPE: DNA

```
<213> ORGANISM: Artificial Sequence
<220> FEATURE:
<223> OTHER INFORMATION: LNA antisense targeting sequence

<400> SEQUENCE: 90
ctcatcttta aatatc                                                   16

<210> SEQ ID NO 91
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 91
tcatctttaa atatct                                                   16

<210> SEQ ID NO 92
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 92
catctttaaa tatcta                                                   16

<210> SEQ ID NO 93
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 93
atctttaaat atctac                                                   16

<210> SEQ ID NO 94
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 94
tctttaaata tctacc                                                   16

<210> SEQ ID NO 95
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 95
ctttaaatat ctacca                                                   16

<210> SEQ ID NO 96
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 96
tttaaatatc taccag                                                   16
```

<210> SEQ ID NO 97
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 97
cgggtagaag actcat                                                  16

<210> SEQ ID NO 98
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 98
ggttagaaga ctcatc                                                  16

<210> SEQ ID NO 99
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 99
gttagaagac tcatct                                                  16

<210> SEQ ID NO 100
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 100
ttagaagact catctt                                                  16

<210> SEQ ID NO 101
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 101
tagaagactc atcttt                                                  16

<210> SEQ ID NO 102
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 102
agaagactca tcttta                                                  16

<210> SEQ ID NO 103
<211> LENGTH: 16
<212> TYPE: DNA
<213> ORGANISM: Artificial Sequence
<220> FEATURE:

```
<223> OTHER INFORMATION: LNA antisense targeting sequence

<400> SEQUENCE: 103
gaagactcat ctttaa                                                   16

<210> SEQ ID NO 104
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 104
aagactcatc tttaaa                                                   16

<210> SEQ ID NO 105
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 105
agactcatct ttaaat                                                   16

<210> SEQ ID NO 106
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 106
gactcatctt taaata                                                   16

<210> SEQ ID NO 107
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 107
actcatcttt aaatat                                                   16

<210> SEQ ID NO 108
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 108
ctcatctata aatatc                                                   16

<210> SEQ ID NO 109
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 109
tcatctttaa atatct                                                   16
```

```
<210> SEQ ID NO 110
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 110
catctttaaa tatcta                                                         16

<210> SEQ ID NO 111
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 111
atctttaaat atctac                                                         16

<210> SEQ ID NO 112
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 112
tctttaaata tctacc                                                         16

<210> SEQ ID NO 113
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 113
ctttaaatat ctacca                                                         16

<210> SEQ ID NO 114
<211> LENGTH: 16
<212> TYPE: DNA
<213> ORGANISM: Artificial Sequence
<220> FEATURE:
<223> OTHER INFORMATION: LNA antisense targeting sequence

<400> SEQUENCE: 114
tttaaatatc taccag                                                         16

<210> SEQ ID NO 115
<211> LENGTH: 10
<212> TYPE: PRT
<213> ORGANISM: Artificial Sequence
<220> FEATURE:
<223> OTHER INFORMATION: Arginine-rich cell penetrating peptide
```

<400> SEQUENCE: 115

Arg Arg Arg Gln Arg Arg Lys Lys Arg Cys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Arginine-rich cell penetrating peptide

<400> SEQUENCE: 116

Arg Arg Arg Arg Arg Arg Arg Arg Arg Phe Phe Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Arginine-rich cell penetrating peptide

<400> SEQUENCE: 117

Arg Arg Arg Arg Arg Phe Phe Arg Arg Arg Arg Cys
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Arginine-rich cell penetrating peptide
<220> FEATURE:
<221> NAME/KEY: MOD_RES
<222> LOCATION: 2, 5, 8, 11, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 118

Arg Xaa Arg Arg Xaa Arg Arg Xaa Arg Arg Xaa Arg Xaa Xaa
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Arginine-rich cell penetrating peptide

<400> SEQUENCE: 119

Arg Arg Arg Arg Arg Arg Arg Arg Cys
1               5

<210> SEQ ID NO 120
<211> LENGTH: 10
<212> TYPE: PRT
<213> ORGANISM: Artificial Sequence

```
<220> FEATURE:
<223> OTHER INFORMATION: Arginine-rich cell penetrating peptide

<400> SEQUENCE: 120

Arg Arg Arg Arg Arg Arg Arg Arg Arg Cys
 1               5                  10

<210> SEQ ID NO 121
<211> LENGTH: 9
<212> TYPE: PRT
<213> ORGANISM: Artificial Sequence
<220> FEATURE:
<223> OTHER INFORMATION: Arginine-rich cell penetrating peptide

<400> SEQUENCE: 121

Arg Arg Arg Arg Arg Arg Arg Arg Gly
 1               5

<210> SEQ ID NO 122
<211> LENGTH: 10
<212> TYPE: PRT
<213> ORGANISM: Artificial Sequence
<220> FEATURE:
<223> OTHER INFORMATION: Arginine-rich cell penetrating peptide

<400> SEQUENCE: 122

Arg Arg Arg Arg Arg Arg Arg Arg Arg Gly
 1               5                  10

<210> SEQ ID NO 123
<211> LENGTH: 17
<212> TYPE: PRT
<213> ORGANISM: Artificial Sequence
<220> FEATURE:
<223> OTHER INFORMATION: Arginine-rich cell penetrating peptide
<220> FEATURE:
<221> NAME/KEY: MOD_RES
<222> LOCATION: 2, 5, 8, 11, 14, 16
<223> OTHER INFORMATION: Acp
<220> FEATURE:
<221> NAME/KEY: MOD_RES
<222> LOCATION: 17
<223> OTHER INFORMATION: bAla

<400> SEQUENCE: 123

Arg Xaa Arg Arg Xaa Arg Arg Xaa Arg Arg Xaa Arg Arg Xaa Arg Xaa
 1               5                  10                  15

Xaa

<210> SEQ ID NO 124
<211> LENGTH: 14
<212> TYPE: PRT
<213> ORGANISM: Artificial Sequence
<220> FEATURE:
<223> OTHER INFORMATION: Arginine-rich cell penetrating peptide
<220> FEATURE:
<221> NAME/KEY: MOD_RES
<222> LOCATION: 2, 8, 13
<223> OTHER INFORMATION: Acp
<220> FEATURE:
<221> NAME/KEY: MOD_RES
<222> LOCATION: 5, 11, 14
```

```
<223> OTHER INFORMATION: bAla

<400> SEQUENCE: 124

Arg Xaa Arg Arg Xaa Arg Arg Xaa Arg Arg Xaa Arg Xaa Xaa
1               5                   10

<210> SEQ ID NO 125
<211> LENGTH: 15
<212> TYPE: PRT
<213> ORGANISM: Artificial Sequence
<220> FEATURE:
<223> OTHER INFORMATION: Arginine-rich cell penetrating peptide

<400> SEQUENCE: 125

Arg Ala Arg Arg Ala Arg Arg Ala Arg Arg Ala Arg Phe Phe Cys
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Arginine-rich cell penetrating peptide

<400> SEQUENCE: 126

Arg Gly Arg Arg Gly Arg Arg Gly Arg Arg Gly Arg Phe Phe Cys
1               5                   10                  15

<210> SEQ ID NO 127
<211> LENGTH: 12
<212> TYPE: PRT
<213> ORGANISM: Artificial Sequence
<220> FEATURE:
<223> OTHER INFORMATION: Arginine-rich cell penetrating peptide

<400> SEQUENCE: 127

Arg Arg Arg Arg Arg Arg Arg Arg Arg Phe Phe Gly
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Arginine-rich cell penetrating peptide
<220> FEATURE:
<221> NAME/KEY: MOD_RES
<222> LOCATION: 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 128

Arg Arg Arg Arg Arg Arg Arg Arg Phe Phe Xaa Xaa
1               5                   10

<210> SEQ ID NO 129
```

```
<211> LENGTH: 12
<212> TYPE: PRT
<213> ORGANISM: Artificial Sequence
<220> FEATURE:
<223> OTHER INFORMATION: Cell penetrating peptide motif
<220> FEATURE:
<221> NAME/KEY: VARIANT
<222> LOCATION: 1, 3, 4, 7, 9, 10
<223> OTHER INFORMATION: Xaa = Lysine, Arginine or Arginine analog
<220> FEATURE:
<221> NAME/KEY: VARIANT
<222> LOCATION: 2, 8
<223> OTHER INFORMATION: Xaa = a neutral amino acid, -C(O)-(CHR)n-NH-,
      where n is 2 to 7 and R is H or methyl.
<220> FEATURE:
<221> NAME/KEY: VARIANT
<222> LOCATION: 5, 6, 11, 12
<223> OTHER INFORMATION: Xaa = alpha-amino acid having a neutral aralkyl
      side chain

<400> SEQUENCE: 129

Xaa Xaa Xaa Xaa Xaa Xaa Xaa Xaa Xaa Xaa Xaa Xaa
 1               5                  10

<210> SEQ ID NO 130
<211> LENGTH: 12
<212> TYPE: PRT
<213> ORGANISM: Artificial Sequence
<220> FEATURE:
<223> OTHER INFORMATION: Cell penetrating peptide motif
<220> FEATURE:
<221> NAME/KEY: VARIANT
<222> LOCATION: 2, 6, 8,12
<223> OTHER INFORMATION: Xaa = a neutral amino acid, -C(O)-(CHR)n-NH-,
      where n is 2 to 7 and R is H or methyl.
      Preferabley Acp

<400> SEQUENCE: 130

Arg Xaa Arg Arg Arg Xaa Arg Xaa Arg Arg Arg Xaa
 1               5                  10

<210> SEQ ID NO 131
<211> LENGTH: 9
<212> TYPE: PRT
<213> ORGANISM: Artificial Sequence
<220> FEATURE:
<223> OTHER INFORMATION: Cell penetrating peptide motif
<220> FEATURE:
<221> NAME/KEY: VARIANT
<222> LOCATION: 3, 5, 9
<223> OTHER INFORMATION: Xaa = a neutral amino acid, -C(O)-(CHR)n-NH-,
      where n is 2 to 7 and R is H or methyl.
      Preferabley Acp

<400> SEQUENCE: 131

Arg Arg Xaa Arg Xaa Arg Arg Arg Xaa
 1               5

<210> SEQ ID NO 132
<211> LENGTH: 12
<212> TYPE: PRT
<213> ORGANISM: Artificial Sequence
<220> FEATURE:
<223> OTHER INFORMATION: Arginine-rich cell penetrating peptide motif
<220> FEATURE:
```

```
<221> NAME/KEY: MOD_RES
<222> LOCATION: 2, 5, 8, 11
<223> OTHER INFORMATION: Acp

<400> SEQUENCE: 132

Arg Xaa Arg Arg Xaa Arg Arg Xaa Arg Arg Xaa Arg
 1               5                  10

<210> SEQ ID NO 133
<211> LENGTH: 12
<212> TYPE: PRT
<213> ORGANISM: Artificial Sequence
<220> FEATURE:
<223> OTHER INFORMATION: Arginine-rich cell penetrating peptide motif
<220> FEATURE:
<221> NAME/KEY: MOD_RES
<222> LOCATION: 3, 6, 9, 12
<223> OTHER INFORMATION: Acp

<400> SEQUENCE: 133

Arg Arg Xaa Arg Arg Xaa Arg Arg Xaa Arg Arg Xaa
 1               5                  10
```